US 7,960,531 B2

(12) United States Patent  
Ferrara et al.

(10) Patent No.: US 7,960,531 B2  
(45) Date of Patent: Jun. 14, 2011

(54) EG-VEGF NUCLEIC ACIDS AND POLYPEPTIDES AND METHODS OF USE

(75) Inventors: Napoleone Ferrara, San Francisco, CA (US); Colin Watanabe, Moraga, CA (US); William I. Wood, Hillsborough, CA (US)

(73) Assignee: Genetech, Inc., South San Francisco, CA (US)

(*) Notice: Subject to any disclaimer, the term of this patent is extended or adjusted under 35 U.S.C. 154(b) by 0 days.

(21) Appl. No.: 12/760,354

(22) Filed: Apr. 14, 2010

(65) Prior Publication Data

US 2010/0256226 A1    Oct. 7, 2010

Related U.S. Application Data

(60) Division of application No. 11/537,472, filed on Sep. 29, 2006, now Pat. No. 7,736,645, which is a continuation of application No. 10/027,603, filed on Dec. 19, 2001, now Pat. No. 7,264,801, which is a continuation-in-part of application No. 09/886,242, filed on Jun. 20, 2001, now abandoned, and a continuation-in-part of application No. PCT/US00/32678, filed on Dec. 1, 2000, and a continuation-in-part of application No. PCT/US00/08439, filed on Mar. 30, 2000, and a continuation-in-part of application No. PCT/US00/04914, filed on Feb. 24, 2000, and a continuation-in-part of application No. PCT/US00/00219, filed on Jan. 5, 2000, said application No. 09/886,242 is a continuation-in-part of application No. 09/709,238, filed on Nov. 8, 2000, now abandoned, which is a continuation of application No. 09/380,137, filed as application No. PCT/US99/12252 on Jun. 2, 1999, now abandoned.

(60) Provisional application No. 60/230,978, filed on Sep. 7, 2000, provisional application No. 60/213,637, filed on Jun. 23, 2000, provisional application No. 60/145,698, filed on Jul. 26, 1999, provisional application No. 60/096,146, filed on Aug. 11, 1998.

(51) Int. Cl.
  *C07H 21/02* (2006.01)
  *C07H 21/04* (2006.01)
  *C12P 21/06* (2006.01)
  *C12N 15/63* (2006.01)

(52) U.S. Cl. ................ 536/23.5; 435/69.1; 435/455

(58) Field of Classification Search .................. None
See application file for complete search history.

(56) References Cited

U.S. PATENT DOCUMENTS

| | | | |
|---|---|---|---|
| 4,946,778 A | 8/1990 | Ladner et al. | |
| 5,858,682 A | 1/1999 | Gruenwald et al. | |
| 6,132,729 A | 10/2000 | Thorpe et al. | |
| 6,180,370 B1 | 1/2001 | Queen et al. | |
| 6,485,938 B1 | 11/2002 | Sheppard et al. | |
| 7,119,177 B2 | 10/2006 | Goddard et al. | |
| 7,189,814 B2 | 3/2007 | Goddard et al. | |
| 7,264,801 B2 | 9/2007 | Ferrara et al. | |
| 7,446,168 B2 | 11/2008 | Ferrara et al. | |
| 7,727,536 B2 | 6/2010 | Ferrara et al. | |
| 7,736,645 B2 | 6/2010 | Ferrara et al. | |
| 2002/0172678 A1 | 11/2002 | Ferrara et al. | |
| 2010/0254999 A1 | 10/2010 | Ferrara et al. | |
| 2010/0256226 A1 | 10/2010 | Ferrara et al. | |

FOREIGN PATENT DOCUMENTS

| | | |
|---|---|---|
| EP | 0 843 563 | 4/1998 |
| EP | 1 033 401 | 9/2000 |
| EP | 0 607 054 | 11/2002 |
| WO | WO 97/07198 | 2/1997 |
| WO | WO 98/39448 | 9/1998 |
| WO | WO 98/42741 | 10/1998 |
| WO | WO 99/06550 | 2/1999 |
| WO | WO 00/53753 | 9/1999 |
| WO | WO 99/46375 | 9/1999 |
| WO | WO 99/53040 | 10/1999 |
| WO | WO 99/63083 | 12/1999 |
| WO | WO 99/63088 | 12/1999 |
| WO | WO 00/08145 | 2/2000 |
| WO | WO 00/52022 | 9/2000 |
| WO | WO 00/70049 | 11/2000 |
| WO | WO 00/73454 | 12/2000 |
| WO | WO 00/75327 | 12/2000 |
| WO | WO 01/36465 | 5/2001 |
| WO | WO 01/40466 | 6/2001 |
| WO | WO 01/57190 | 8/2001 |

OTHER PUBLICATIONS

Abaza et al., 1992, "Effects of amino acid substitutions outside an antigenic site on protein binding to monoclonal antibodies of predetermined specificity obtained by peptide immunization: demonstration with region 94-100 (antigenic site 3) of myoglobin." J Protein Chem. 11(5):433-444.

Aird et al., 1997, "Vascular bed-specific expression of an endothelial cell gene is programmed by the tissue microenvironment". Cell Bio. 138:1117-1124.

Aravind & Koonen., 1998, "A colipase fold in the carboxy-terminal domain of the Wnt antagonists—the Dickkopfs" Curr Biol., 8:477-478.

Arbiser et al., 1997, "Oncogenic H-ras stimulates tumor angiogenesis by two distinct pathways" Proc. Natl. Acad. Sci. USA, 94:861-866.

Attwood et al., 2000, "The babel of bioinformatics." Science 290(5491):417-473.

(Continued)

*Primary Examiner* — Michail A Belyavskyi  
(74) *Attorney, Agent, or Firm* — Jones Day

(57) ABSTRACT

The present invention is directed to novel polypeptides designated herein as EG-VEGF and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention. Also provided herein are methods of screening for modulators of EG-VEGF. Furthermore, methods and related methods of treatment are described herein which pertain to regulating cellular proliferation and chemotaxis.

17 Claims, 61 Drawing Sheets

OTHER PUBLICATIONS

Barrios et al., 2004, "Length of the antibody heavy chain complementarity determining region 3 as a specificity-determining factor." J Molec. Recognition 17:332-338.

Basset, D.L., 1943, "The changes in the vascular pattern of the ovary of the albino rat during the estrous cycle" Am. J. Anat., 73:251-278.

Boisbouvier et al., 1998, "A structural homologue of colipase in black mamba venom revealed by NMR floating disulphide bridge analysis" J. Mol. Biol. 283: 205-219.

Bowie et al., 1999, "Deciphering the Message in Protein Sequences: Tolerance to Amino Acid Substitutions" Science, 247(247): 1306-1310.

Brandon, 1985, "Improved Immunocytochemical Straining Through the Use of Fab Fragments of Primary Antibody, Fab-specific Second Antibody, and Fab-Horseradish Peroxidase." J. of Histochem. & Cytochem. 33(7): 715-719715-719.

Brekken et al., 1998, "Vascular endothelial growth factor as a marker of tumor endothelium." Cancer Res 58(9):1952-59.

Bullock et al., 2004, "Structural determinants required for the bioactivities of prokineticins and identification of prokineticin receptor antagonists" Mol. Pharmacol. 65:582-588.

Carmeliet et al., 2001, "Cardiovascular biology. Creating unique blood vessels." Nature 412:868-869.

Carmeliet, P., 2000, "Mechanisms of angiogenesis and arteriogenesis" Nature Medicine. 6:389-395.

Collin, O. & Bergh, A. 1996,"Leydig cells secrete factors which increase vascular permeability and endothelial cell proliferation" Int. J. Androl., 19:221-228.

Dellian, M. et al., 1996, "Quantitation and physiological characterization of angiogenic vessels in mice: effect of basic fibroblast growth factor, vascular endothelial growth factor/vascular permeability factor, and host microenvironment" Am. J. Pathology, 149:59-71.

Dermer, Gerald B. 1994, "Another anniversary for the war on cancer," Bio/Technology, 12:320.

Esser, S. et al., 1998. "Vascular endothelial growth factor induces endothelial fenestrations in vitro" J. Cell. Biol., 140:947-959.

Ferrara et al., 2004, "EG-VEGF and Bv8: a novel family of tissue-restricted angiogenic factors." Biochim Biophys acta 1654(1):69-78.

Ferrara, N. & Alitalo, 1999, "K. Clinical applications of angiogenic growth factors and their inhibitors" Nature Medicine, 5:1359-1364.

Ferrara, N. et al.. 1998, "Vascular endothelial growth factor is essential for corpus luteum angiogenesis" Nature Medicine, 4:336-340.

Ferrara, N., 2000, "VEGF: an update on biological and therapeutic aspects" Curr. Opin. Biotech 11: 617-624.

Fogarty, M et al 2002, "Information overload," The Scientist, 2002, 16(16):16.

Fraser et al., 2000, "Suppression of Luteal Angiogenesis in the Primate after Neutralization of Vascular Endothelial Growth Factor" Endocrinology, 141(3):995-1000.

GENBANK Blast results A1-A42: Sequence Identity comparison of: P_AAC84469, P_AAF44237, P_AAC97496, P_AAS21478, P_AAZ65091, AX056658, P_AAC84303, AX048197, P_AAF85370, AX146968, P_AAA75155, P_AAA75177, P_AAA75176, P_AAA75175, and AF333024, dated Nov. 21, 2001.

GENBANK Blast results B1-B5 Sequence Identity comparison of P_AAB53096, P_AAB48067, P_AAB65268, P_AAB48175, P_AAB70148, P_AAB68427, P_AAU12406, P_AAY66745, P_AAB18453, CAC41157.1, NP_115790.1. PRK1_HUMAN, P_AAB70147, P_AAM79066, P_AAB18475, P_AAB18474, P_AAB18473, P_AAB70146, P_AAB70145, dated Nov. 21, 2001.

Gille, H, et al., 2001, "Analysis of biological effects and signaling properties of Flt-1(VEGFR-1) and KDR (VEGFR-2). A reassessment using novel receptor-specific vascular endothelial growth factor mutants" J. Biol. Chem., 276:3222-3230.

Glinka, A. et al., 1998, "Dickkopf-1 is a member of a new family of secreted proteins and functions in head induction" Nature, 391:357-362.

Goldziher, J.W. & Green, J.A.., 1962, "The polycystic ovary. I. Clinical and histologic features" J. Clin. Endocrinol. Meta. 22:325-332.

Gospodarowitcz et al., 1984 "Comparison of the Ability of Basement Membranes Produced by Corneal Endothelial and Mouse-derived Endodermal PF-HR-9 Cells to Support the Proliferation and Differentiation of Bovine Kidney Tubule Epithelial Cells in Vitro", J. Cell. Biol., 99:947-961.

Gura et al., 1997, "Systems for identifying new drugs are often faulty." Science 278:1041-1042.

Harlow et al., 1988, Antibodies—A Laboratory manual, Cold Spring Harbor laboratory production, Cold Spring Harbor, NY pp. 626-629.

Herberman et al., 2006, "Cancer chemoprevention and cancer preventive vaccines—a call to action: leaders of diverse stakeholder groups present strategies for overcoming multiple barriers to meet an urgent need." Cancer Res. 66:11540-11549.

Joubert, F.J. & Strydom, D.J., 1980, "Snake venom. The amino acid sequence of protein A from Dendroaspis polylepis polytepis (black mamba) veno" Hoppe-Seylers Zeitschrijt fur Physiologische Chemie, 361:1787-1794.

Klagsburn, M.. 1992, "Mediators of angiogenesis: the biological significance of basic fibroblast growth factor (bFGF)-heparin and heparan sulfate interactions" Semin. Cancer Biol., 3:81-87.

Klein, R. et al., 1996, "Selection for Genes Encoding Secreted Proteins and Receptors," Proc. Natl. Acad. Sci. USA, 93: 7108-7113.

Kobrin et al., 1991, "A V region mutation in a phosphocholine-binding monoclonal antibody results in loss of antigen binding." J Immunol. 146:2017-2020.

Krupnik, V.E. et al., 1999, "Functional and structural diversity of the human Dickkopf gene family" Gene, 238:301-313.

Kuby et al., 1994, Immunol. $2^{nd}$ edition pp. 85-96.

Lecouter et al., 2001 "Identification of an angiogenic mitogen selective for endocrine gland endothelium." Nature 412(6850) : 887-884.

Leung et al.. 1989, "Vascular endothelial growth factor is a secreted angiogenic mitogen" Science, 246: 1306-1309.

Lind et al., 1995, "Chemotaxis of bumna osteoblasts" APMIS, 103:140-146.

Melton, D. A. et al., 1984, "Efficient in vitro synthesis of biologically active RNA and RNA hybridization probes from plasmids containing a bacteriophage SP6 promoter" Nucleic Acids Res., 12:7035-7056.

Mesiano, S., 1993, "Mitogenic Action, Regulation, and Localization of insulin-Like Growth Factors in the Human Fetal Adrenal Gland" J. Clin. Endocrinol. Metab. 76:968-976.

Mikayama, 1993, "Molecular cloning and functional expression of a cDNA encoding gycosylation-inhibiting factor." Proc. Natl. Acad. Sci 90:10056-10060.

Mueller et al., 1995, "Cloning of ATAC, an activation-induced chemokine-related molecule exclusively expressed in CD7+ T lunphocytes" Eur. J. Immunol., 25:1744-1746.

NCBI, Accession No. AA150370: Genome Research, Nov. 15, 1996, Hillier, L. et al.

NCBI, Accession No. AA843667, National Cancer Institute, Mar. 4, 1998, Strausberg, Robert.

NCBI, Accession No. AA865629: National Cancer Institute, Apr. 21, 1998, Strausberg, Robert.

NCBI, Accession No. AF131820: Direct Submission, Submitted: Feb. 26, 1999, Mei, G. et al.

Negri et al., 2005, "Biological activities of Bv8 analogues." Brit. J Pharm. 146:625-632.

Ngo et al., 1994, The protein Folding Problem and tertiary Structure Prediction, Merz et al. eds Birkhauser, Boston, MA 443 and 492-495.

Palade, G.E. et al., 1979, "Structural aspects of the permeability of the microvascular endothelium" Acta Physiol. Scand. Suppl., 463:11-32.

Petterson, A. et al., 2000, "Heterogeneity of the angiogenic response induced in different normal tissues by vascular permeability factor/ vascular endothelial growth factor" Lab. Invest. 80:99-115.

Phillips et al., 1990, "Vascular endothelial growth factor is expressed in rat corpus luteum" Endocrinology, 127:965-967.

Phillips, H.S. et al., 1990, "Widespread expression of BDNF but not NT3 by target areas of basal forebrain cholinergic neurons" Science 250:290-294.

Ravindranath et al., 1992, "Vascular Endothelial Growth Factor Messenger Ribonucleic Acid Expression in the Primate Ovary" Endocrinology, 131 (1):254-260.

Rieger R et al, Glossary of Genetics: Classical and Molecular, p. 16, 5th Edition, 1991, Berlin, New York: Springer-Verlag.

Roberts and Palade, 1997, "Host Microvascularture Influence on Tumor Vascular Morphology and Endothelial Gene Expression" Cancer Res., 57:765-772.

Ryan A.M. et al., 1999, "Preclinical safety evaluation of rhuMAbVEGF, an Antiangiogenic humanized monoclonal antibody" Toxicol. Pathol. 27:78-86.

Schnabel, M. et al., "Dedifferentiation-associated changes in morphology and gene expression in primary human articular chondrocytes in cell culture," Osteoarthritis and Cartilage, vol. 10, pp, 62-70 (2002).

Schweitz et al., 1999, "MIT(I), a black mamba toxin with a new and highly potent activity on intestinal contraction" FEBS Lett. 461:183-188.

Semenza, G.L., 2000, "HIF-I: mediator of physiological and pathophysiological response to hypoxia" J. Appl. Physiol. 88:1474-1480.

Simionescu et al., 1988, "The Cardiovascular System" ed. Weiss, L., Urban & Schwarzensberg, Baltimore 355-398.

Skolnick et al., 2000, "From genes to protein structure and function: novel applications of computational approaches in the genomic era," Trends in Biotech 19(1):34-39.

Soker et al., 1998, "Neuropilin-I is expressed by endothelial and tumor cells as an isoform-specific receptor for vascular endothelial growth factor" Cell 92:735-745.

Stewart and Wiley, 1981, "Developing Nervous Tissue Induces Formation of Blood-Brain Barrier Characteristics in invading Endothelial Cells: A Study Using Quail-Chick Transplantation Chimeras" Dev. Biol. 84: 183-192.

Strausberg, Robert, National Cancer Institute, Cancer Genome Anatomy Project (CGAP), Tumor Gene Index, GenBank Database Accession No. AA883760, National Center for Biotechnology Information, Bethesda, MD Mar. 27, 1998.

Stryer et al., 1998, Biochemistry. $3^{rd}$ edition, WH Freeman Company, New York. pp. 31-33.

Tashiro, K. et al., "Signal Sequence Trap: A Cloning Strategy for Secreted Proteins and Type I Membrane Proteins," Science, 261. pp, 600-603 (Jul. 30, 1993).

Taub et al., 1995 "T Lymphocyte Recruitment by Interleukin-8 (IL-8)" J. Clin. Invest. 95:1370-137.

Van Tilbeurgh et al., 1992, "Structure of the pancreatic lipase-procolipase complex" Nature, 359: 159-162.

Wallin, E. et al, 1995, "Properties of N-terminal tails in G-protein coupled receptors: a statistical study," Protein Engineering, vol. 8, No. 7. pp. 693-698.

Wechselberger, C. et al., 1999, "The mammalian homologues of frog Bv8 are mainly expressed in spermatocytes" FEBS Lett. 462:177-181.

Yokoyama-Kobayashi, M. et al., "A signal sequence detection system using secreted protease activity as an indicator." Gene, vol. 163, pp. 193-196 (1995).

Zetter, B.R., 1980, "Migration of capillary endothelial cells is stimulated by tumour-derived factors" Nature, 285:41-43.

Zhang, Y. et al., "Versiean Modulates Embryonic Chondrocyte Morphology via the Epidermal Growth Factor-like Motifs in G3," Exper. Cell Research, vol. 263, pp. 33-42 (2001).

FIGURE 1

TGGCCTCCCCAGCTTGCCAGGCACAAGGCTGAGCGGGAGGAAGCGAGAGGCATCTA
AGCAGGCAGTGTTTTGCCTTCACCCCAAGTGACCATGAGAGGTGCCACGCGAGTCTC
AATCATGCTCCTCCTAGTAACTGTGTCTGACTGTGCTGTGATCACAGGGGCCTGTGA
GCGGGATGTCCAGTGTGGGGCAGGCACCTGCTGTGCCATCAGCCTGTGGCTTCGAGG
GCTGCGGATGTGCACCCCGCTGGGGCGGGAAGGCGAGGAGTGCCACCCCGGCAGCC
ACAAGGTCCCCTTCTTCAGGAAACGCAAGCACCACACCTGTCCTTGCTTGCCCAACC
TGCTGTGCTCCAGGTTCCCGGACGGCAGGTACCGCTGCTCCATGGACTTGAAGAACA
TCAATTTTTAGGCGTTGCCTGGTCTCAGGATACCCACCATCCTTTTCCTGAGCACAG
CCTGGATTTTTATTTCTGCCATGAAACCCAGCTCCCATGACTCTCCCAGTCCCTACAC
TGACTACCCTGATCTCTCTTGTCTAGTACGCACATATGCACACAGGCAGACATACCT
CCCATCATGACATGGTCCCCAGGCTGGCCTGAGGATGTCACAGCTTGAGGCTGTGGT
GTGAAAGGTGGCCAGCCTGGTTCTCTTCCCTGCTCAGGCTGCCAGAGAGGTGGTAAA
TGGCAGAAAGGACATTCCCCCTCCCCTCCCCAGGTGACCTGCTCTCTTTCCTGGGCCC
TGCCCCTCTCCCCACATGTATCCCTCGGTCTGAATTAGACATTCCTGGGCACAGGCTC
TTGGGTGCATTGCTCAGAGTCCCAGGTCCTGGCCTGACCCTCAGGCCCTTCACGTGA
GGTCTGTGAGGACCAATTTGTGGGTAGTTCATCTTCCCTCGATTGGTTAACTCCTTAG
TTTCAGACCACAGACTCAAGATTGGCTCTTCCCAGAGGGCAGCAGACAGTCACCCCA
AGGCAGGTGTAGGGAGCCCAGGGAGGCCAATCAGCCCCCTGAAGACTCTGGTCCCA
GTCAGCCTGTGGCTTGTGGCCTGTGACCTGTGACCTTCTGCCAGAATTGTCATGCCTC
TGAGGCCCCCTCTTACCACACTTTACCAGTTAACCACTGAAGCCCCCAATTCCCACA
GCTTTTCCATTAAAATGCAAATGGTGGTGGTTCAATCTAATCTGATATTGACATATTA
GAAGGCAATTAGGGTGTTTCCTTAAACAACTCCTTTCCAAGGATCAGCCCTGAGAGC
AGGTTGGTGACTTTGAGGAGGGCAGTCCTCTGTCCAGATTGGGGTGGGAGCAAGGG
ACAGGGAGCAGGGCAGGGGCTGAAAGGGGCACTGATTCAGACCAGGGAGGCAACT
ACACACCAACATGCTGGCTTTAGAATAAAAGCACCAACTGAAAAAA

FIGURE 2

MRGATRVSIMLLLVTVSDCAVITGACERDVQCGAGTCCAISLWLRGLRMCTPLGREGEEC
HPGSHKVPFFRKRKHHTCPCLPNLLCSRFPDGRYRCSMDLKNINF

Important features:

Signal peptide:
1-19

N-myristoylation sites:
   33
   35
   46

FIGURE 3A

PRO                    XXXXXXXXXXXXXXX    (Length = 15 amino acids)

Comparison Protein     XXXXXYYYYYYY       (Length = 12 amino acids)

% amino acid sequence identity =

(the number of identically matching amino acid residues between the two polypeptide sequences as determined by ALIGN-2) divided by (the total number of amino acid residues of the PRO polypeptide) =

5 divided by 15 = 33.3%

FIGURE 3B

PRO                XXXXXXXXXX         (Length = 10 amino acids)

Comparison Protein XXXXXYYYYYZZYZ     (Length = 15 amino acids)

% amino acid sequence identity =

(the number of identically matching amino acid residues between the two polypeptide sequences as determined by ALIGN-2) divided by (the total number of amino acid residues of the PRO polypeptide) =

5 divided by 10 = 50%

FIGURE 3C

PRO-DNA        NNNNNNNNNNNNNN        (Length = 14 nucleotides)

Comparison DNA NNNNNNLLLLLLLLLL      (Length = 16 nucleotides)

% nucleic acid sequence identity =

(the number of identically matching nucleotides between the two nucleic acid sequences as determined by ALIGN-2) divided by (the total number of nucleotides of the PRO-DNA nucleic acid sequence) =

6 divided by 14 = 42.9%

FIGURE 3D

PRO-DNA              NNNNNNNNNNNN        (Length = 12 nucleotides)

Comparison DNA       NNNNLLLVV           (Length = 9 nucleotides)

% nucleic acid sequence identity =

(the number of identically matching nucleotides between the two nucleic acid sequences as determined by ALIGN-2) divided by (the total number of nucleotides of the PRO-DNA nucleic acid sequence) =

4 divided by 12 = 33.3%

FIGURE 4

TGGCTCCCCAGCTTGCCAGGCACAAGGCTGAGCTGGAGGAAGCGAGANGCATCTAAGCAG
GCAGTGTTTTGCCTTCACCCCAAGTGACCATGAGAGGTGCCACGCGAGTCTCAATCATGC
TCCTCCTAGTAACTGTGTCTGACTGTGCTGTGATCACAGGGGCCTGTGAGCGGGATGTCC
AGTGTGGGGCAGGCACCTGCTGTGCCATCAGCCTGTGGCTTCGAGGGCTGCGGATGTGCA
CCCCGCTGGGGCGGGAAGGCGAGGAGTGCCACCCCGGCAGCCACAAGGTCCCCTTCTTCA
GGAAACGCAAGCACCACACCTGTCTTGTTGCCCAACCTGCTGTGCTCCAGTTCCGGACGG
CAGTACGCTGCTCA $Kd = 1.43 +/- 0.4$ nM $Kd = 0.95 +/- 0.6$ nM

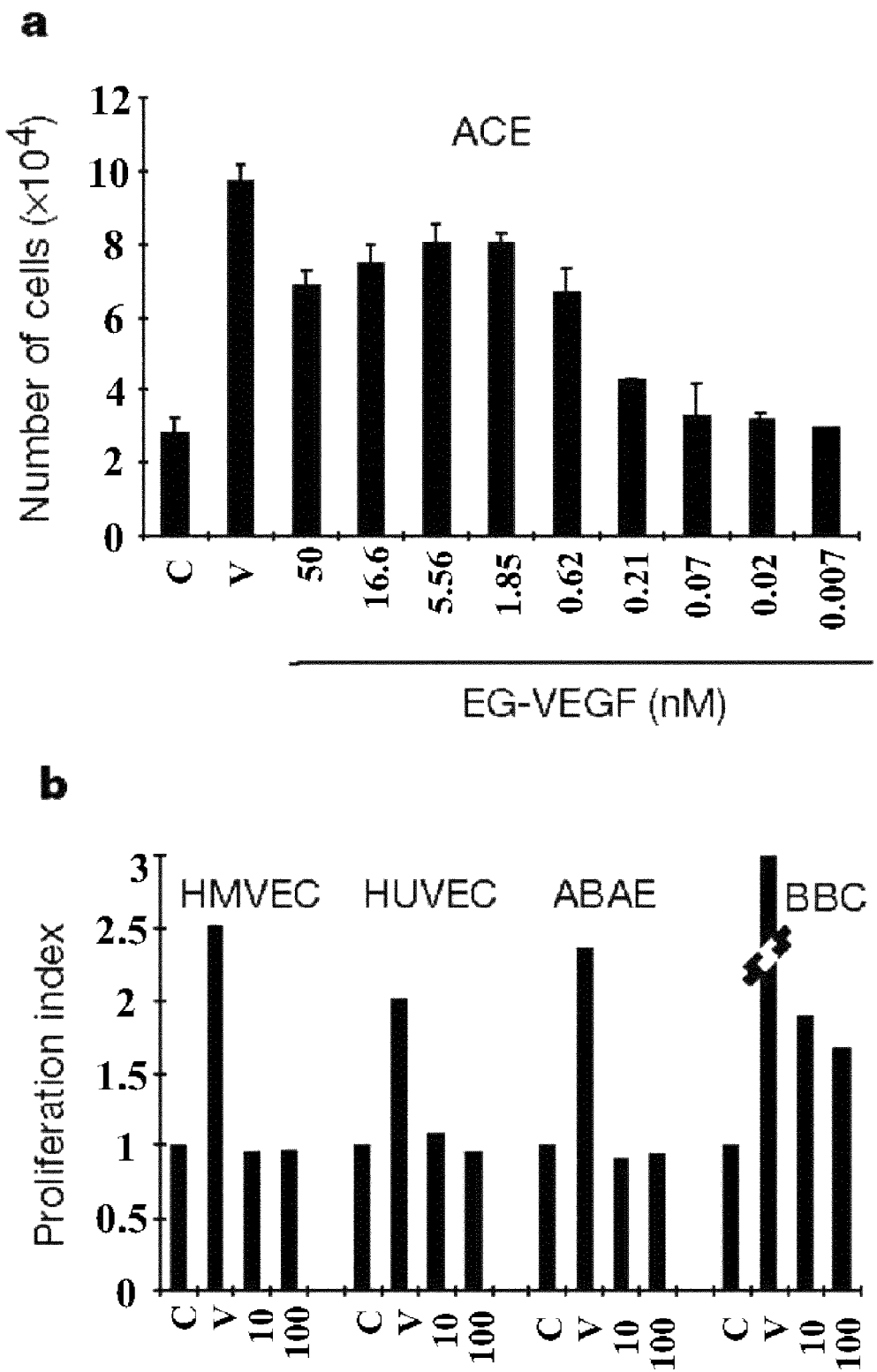
Figure 13A-B

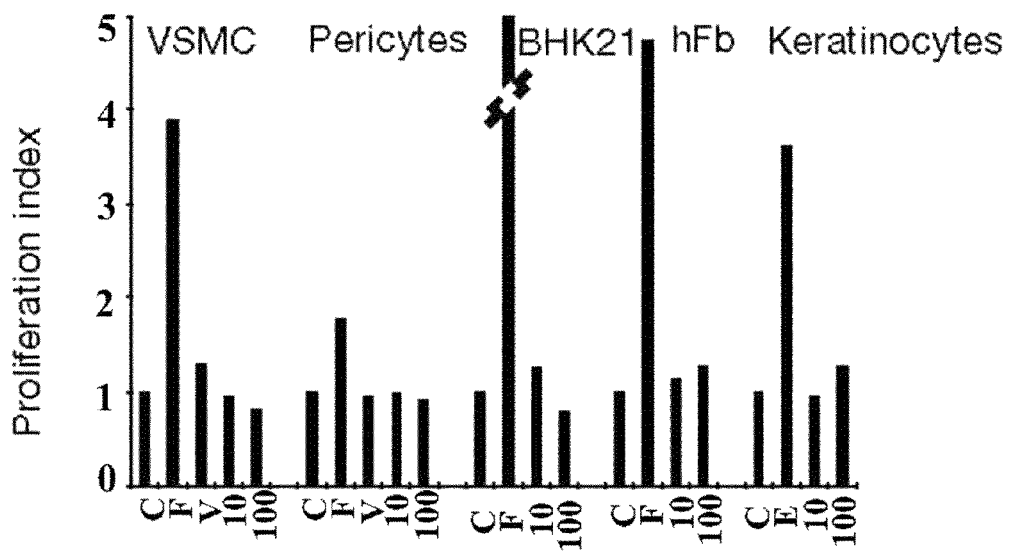
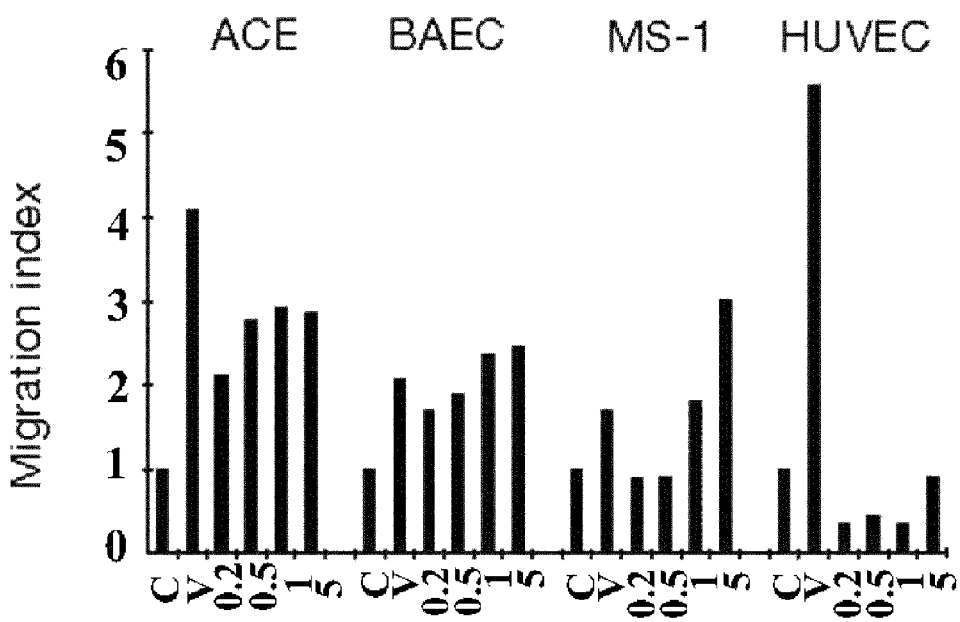
Figure 13C-D

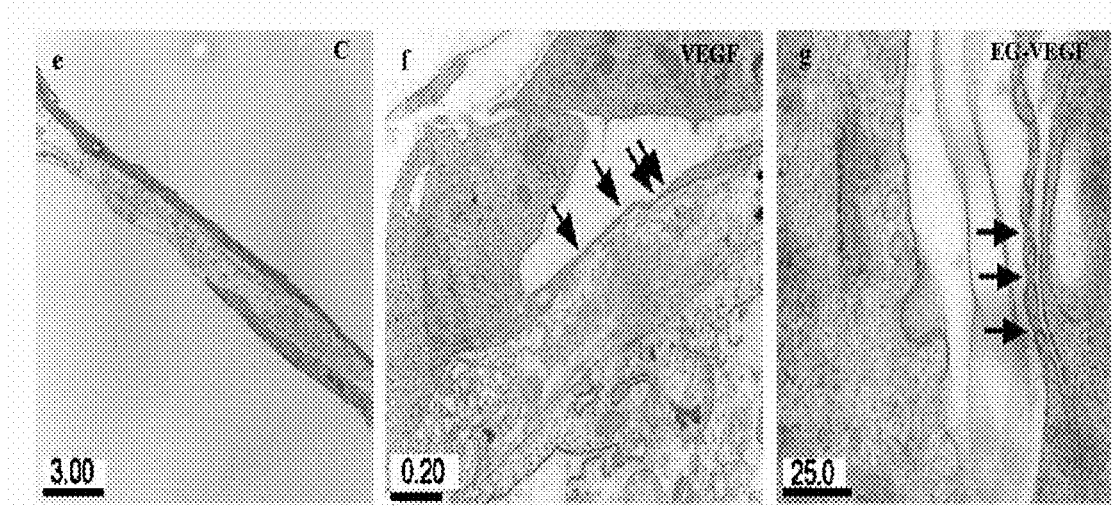
Figure 13E-G

FIGURE 16 A-C a
```
TGGCCTCCCCAGCTTGCCAGGCACAAGGCTGAGCGGGAGGAAGCGAGAGG      50
CATCTAAGCAGGCAGTGTTTTGCCTTCACCCCAAGTGACCATGAGAGGTG
                                        M  R  G
CCACGCGAGTCTCAATCATGCTCCTCCTAGTAACTGTGTCTGACTGTGCT
 A  T  R  V  S  I  M  L  L  L  V  T  V  S  D  C  A
GTGATCACAGGGGCCTGTGAGCGGGATGTCCAGTGTGGGGCAGGCACCTG     200
 V  I  T  G  A  C  E  R  D  V  Q  C  G  A  G  T  C
CTGTGCCATCAGCCTGTGGCTTCGAGGGCTGCGGATGTGCACCCCGCTGG
 C  A  I  S  L  W  L  R  G  L  R  M  C  T  P  L
GGCGGGAAGGCGAGGAGTGCCACCCCGGCAGCCACAAGGTCCCCTTCTTC
 G  R  E  G  E  E  C  H  P  G  S  H  K  V  P  F  F
AGGAAACGCAAGCACCACACCTGTCCTTGCTTGCCCAACCTGCTGTGCTC
 R  K  R  K  H  H  T  C  P  C  L  P  N  L  L  C  S
CAGGTTCCCGGACGGCAGGTACCGCTGCTCCATGGACTTGAAGAACATCA     400
 R  F  P  D  G  R  Y  R  C  S  M  D  L  K  N  I
ATTTTTAGGCGCTTGCCTGGTCTCAGGATACCCACCATCCTTTTCCTGAG
 N  F  *
CACAGCCTGGATTTTTATTTCTGCCATGAAACCCAGCTCCCATGACTCTC
CCAGTCCCTACACTGACTACCCTGATCTCTCTTGTCTAGTACGCACATAT
GCACACAGGCAGACATACCTCCCATCATGACATGGTCCCCAGGCTGGCCT     600
GAGGATGTCACAGCTTGAGGCTGTGGTGTGAAAGGTGGCCAGCCTGGTTC
TCTTCCCTGCTCAGGCTGCCAGAGACGTGGTAAATCGGCAGAAAGGACATT
CCCCCTCCCCTCCCCAGGTGACCTGCTCTCTTTCCTGGGCCCTGCCCCTC
TCCCCACATGTATCCCTCGGTCTGAATTAGACATTCCTGGGCACAGGCTC     800
TTGGGTGCATTGCTCAGAGTCCCAGGTCCTGGCCTGACCCTCAGGCCCTT
CACGTGAGGTCTGTGAGGACCAATTTGTGGGTAGTTCATCTTCCCTCGAT
TGGTTAACTCCTTAGTTTCAGACCACAGACTCAAGATTGGCTCTTCCCAG
AGGGCAGCAGACAGTCACCCCAAGGCAGGTGTAGGCAGCCCAGGGAGGCC
AATCAGCCCCCTGAAGACTCTGGTCCCAGTCAGCCTGTGGCTTGTGGCCT    1000
GTGACCTGTGACCTTCTGCCAGAATTGTCATGCCTCTGAGGCCCCCTCTT
ACCACACTTTACCAGTTAACCACTGAAGCCCCCAATTCCCACAGCTTTTC
CATTAAAATGCAAATGGTGGTGGTTCAATCTAATCTGATATTGACATATT    1200
AGAAGGCAATTAGGGTGTTTCCTTAAACAACTCCTTTCCAAGGATCAGCC
CTGACAGCAGGTTGGTGACTTTGAGGAGGGCAGTCCTCTGTCCAGATTGG
GGTGGGAGCAAGGGACAGGGAGCAGGGCAGGGGCTGAAAGGGGCACTGAT
TCAGACCAGGGAGGCAACTACACACCAACATGCTGGCTTTAGAATAAAAG    1400
CACCAACTGAAAAAA
``` b
```
MRGATRVSIMLLLVTVSDC AVITGACERD VQCG A GTCCA I SLW LRGL RM C  50   EG-VEGF
MLLLLLLLPPLLLPRAGDA AVITGAC DK D SQCG G M CCAVS I WMKS I R I C  48   Bv8 hom
                   AVITGACERD I QCG K GTCCAVSLW I KSMR V C  31   VPRA TP LGRE GE E CHP F SHKVPFF RK R KH HTCPCLPNL L CSR F PDG R YR C SMDL  100  EG-VEGF
TP MGKLG DS CHP L TRK VPFFG RM HHTCPCLF G LAC L R T SFNR F I CIAQK   95  Bv8 hom
TP MGTSGE CHP A SHK L PF S GQ RMHHTCPC A PNLAC V GTHK-K F KCL S K    79  VPRA

KNINF    105    EG-VEGF
``` c
```
E RDV Q CGAGT CCA I SLW LRGLR--M CTPLG REGEE C --H PG SHKVPFF     70   EG-VEGF
D NQRD C QPGL CCA FQ---RGIL FPVCTPL PVEGE H --ID EA SRLLDLI    252   hdkk3
L RSTD C APGL CCA-----RH FWSKI KE VLDEG QV TK RRKGS-----     215   xdkk1
Q LNSA C KSN-C CQ HDTI S SLS R ---CALKA RE NS EC SAFTLYG------    55   col RKRKH-----HT CPC L PN LL C SR---------FPDGRYR C SMDLKNINF     105   EG-VEGF
TWELEPDGALDR CPC ASGLLC QP--------HSHSLVYV C KPTFVG          290   hdkk3
-HGLE---IFQR CH GAG LS CRLQKGEFTTVPKTSRLHT QRH               254   xdkk1
--------VYYK CPC ERGL I CEGDKSLV-GSITNTNFGI C HDVGRSSD         94   col
```

```
/*
 *
 * C-C increased from 12 to 15
 * Z is average of EQ
 * B is average of ND
 * match with stop is _M; stop-stop = 0; J (joker) match = 0
 */
define   _M    -8        /* value of a match with a stop */ int      _day[26][26] = {
/*      A  B  C  D  E  F  G  H  I  J  K  L  M  N  O  P  Q  R  S  T  U  V  W  X  Y  Z */
/* A */ { 2, 0,-2, 0, 0,-4, 1,-1,-1, 0,-1,-2,-1, 0,_M, 1, 0,-2, 1, 1, 0, 0,-6, 0,-3, 0},
/* B */ { 0, 3,-4, 3, 2,-5, 0, 1,-2, 0, 0,-3,-2, 2,_M,-1, 1, 0, 0, 0, 0,-2,-5, 0,-3, 1},
/* C */ {-2,-4,15,-5,-5,-4,-3,-3,-2, 0,-5,-6,-5,-4,_M,-3,-5,-4, 0,-2, 0,-2,-8, 0, 0,-5},
/* D */ { 0, 3,-5, 4, 3,-6, 1, 1,-2, 0, 0,-4,-3, 2,_M,-1, 2,-1, 0, 0, 0,-2,-7, 0,-4, 2},
/* E */ { 0, 2,-5, 3, 4,-5, 0, 1,-2, 0, 0,-3,-2, 1,_M,-1, 2,-1, 0, 0, 0,-2,-7, 0,-4, 3},
/* F */ {-4,-5,-4,-6,-5, 9,-5,-2, 1, 0,-5, 2, 0,-4,_M,-5,-5,-4,-3,-3, 0,-1, 0, 0, 7,-5},
/* G */ { 1, 0,-3, 1, 0,-5, 5,-2,-3, 0,-2,-4,-3, 0,_M,-1,-1,-3, 1, 0, 0,-1,-7, 0,-5, 0},
/* H */ {-1, 1,-3, 1, 1,-2,-2, 6,-2, 0, 0,-2,-2, 2,_M, 0, 3, 2,-1,-1, 0,-2,-3, 0, 0, 2},
/* I */ {-1,-2,-2,-2,-2, 1,-3,-2, 5, 0,-2, 2, 2,-2,_M,-2,-2,-2,-1, 0, 0, 4,-5, 0,-1,-2},
/* J */ { 0, 0, 0, 0, 0, 0, 0, 0, 0, 0, 0, 0, 0, 0,_M, 0, 0, 0, 0, 0, 0, 0, 0, 0, 0, 0},
/* K */ {-1, 0,-5, 0, 0,-5,-2, 0,-2, 0, 5,-3, 0, 1,_M,-1, 1, 3, 0, 0, 0,-2,-3, 0,-4, 0},
/* L */ {-2,-3,-6,-4,-3, 2,-4,-2, 2, 0,-3, 6, 4,-3,_M,-3,-2,-3,-3,-1, 0, 2,-2, 0,-1,-2},
/* M */ {-1,-2,-5,-3,-2, 0,-3,-2, 2, 0, 0, 4, 6,-2,_M,-2,-1, 0,-2,-1, 0, 2,-4, 0,-2,-1},
/* N */ { 0, 2,-4, 2, 1,-4, 0, 2,-2, 0, 1,-3,-2, 2,_M,-1, 1, 0, 1, 0, 0,-2,-4, 0,-2, 1},
/* O */ {_M,_M,_M,_M,_M,_M,_M,_M,_M,_M,_M,_M,_M,_M, 0,_M,_M,_M,_M,_M,_M,_M,_M,_M,_M,_M},
/* P */ { 1,-1,-3,-1,-1,-5,-1, 0,-2, 0,-1,-3,-2,-1,_M, 6, 0, 0, 1, 0, 0,-1,-6, 0,-5, 0},
/* Q */ { 0, 1,-5, 2, 2,-5,-1, 3,-2, 0, 1,-2,-1, 1,_M, 0, 4, 1,-1,-1, 0,-2,-5, 0,-4, 3},
/* R */ {-2, 0,-4,-1,-1,-4,-3, 2,-2, 0, 3,-3, 0, 0,_M, 0, 1, 6, 0,-1, 0,-2, 2, 0,-4, 0},
/* S */ { 1, 0, 0, 0, 0,-3, 1,-1,-1, 0, 0,-3,-2, 1,_M, 1,-1, 0, 2, 1, 0,-1,-2, 0,-3, 0},
/* T */ { 1, 0,-2, 0, 0,-3, 0,-1, 0, 0, 0,-1,-1, 0,_M, 0,-1,-1, 1, 3, 0, 0,-5, 0,-3, 0},
/* U */ { 0, 0, 0, 0, 0, 0, 0, 0, 0, 0, 0, 0, 0, 0,_M, 0, 0, 0, 0, 0, 0, 0, 0, 0, 0, 0},
/* V */ { 0,-2,-2,-2,-2,-1,-1,-2, 4, 0,-2, 2, 2,-2,_M,-1,-2,-2,-1, 0, 0, 4,-6, 0,-2,-2},
/* W */ {-6,-5,-8,-7,-7, 0,-7,-3,-5, 0,-3,-2,-4,-4,_M,-6,-5, 2,-2,-5, 0,-6,17, 0, 0,-6},
/* X */ { 0, 0, 0, 0, 0, 0, 0, 0, 0, 0, 0, 0, 0, 0,_M, 0, 0, 0, 0, 0, 0, 0, 0, 0, 0, 0},
/* Y */ {-3,-3, 0,-4,-4, 7,-5, 0,-1, 0,-4,-1,-2,-2,_M,-5,-4,-4,-3,-3, 0,-2, 0, 0,10,-4},
/* Z */ { 0, 1,-5, 2, 3,-5, 0, 2,-2, 0, 0,-2,-1, 1,_M, 0, 3, 0, 0, 0, 0,-2,-6, 0,-4, 4}
};
```

Page 1 of day.h

FIGURE 20 B

```c
/*
*/
#include <stdio.h>
include <ctype.h> define  MAXJMP    16      /* max jumps in a diag */
define  MAXGAP    24      /* don't continue to penalize gaps larger than this */
#define  JMPS      1024    /* max jmps in an path */
define  MX        4       /* save if there's at least MX-1 bases since last jmp */ define  DMAT      3       /* value of matching bases */
define  DMIS      0       /* penalty for mismatched bases */
#define  DINS0     8       /* penalty for a gap */
#define  DINS1     1       /* penalty per base */
#define  PINS0     8       /* penalty for a gap */
define  PINS1     4       /* penalty per residue */ struct jmp {
        short           n[MAXJMP];          /* size of jmp (neg for dely) */
        unsigned short  x[MAXJMP];          /* base no. of jmp in seq x */
};                                          /* limits seq to 2^16 -1 */ struct diag {
        int             score;              /* score at last jmp */
        long            offset;             /* offset of prev block */
        short           ijmp;               /* current jmp index */
        struct jmp      jp;                 /* list of jmps */
};

struct path {
        int             spc;                /* number of leading spaces */
        short           n[JMPS];            /* size of jmp (gap) */
        int             x[JMPS];            /* loc of jmp (last elem before gap) */
};

char            *ofile;                     /* output file name */
char            *namex[2];                  /* seq names: getseqs() */
char            *prog;                      /* prog name for err msgs */
char            *seqx[2];                   /* seqs: getseqs() */
int             dmax;                       /* best diag: nw() */
int             dmax0;                      /* final diag */
int             dna;                        /* set if dna: main() */
int             endgaps;                    /* set if penalizing end gaps */
int             gapx, gapy;                 /* total gaps in seqs */
int             len0, len1;                 /* seq lens */
int             ngapx, ngapy;               /* total size of gaps */
int             smax;                       /* max score: nw() */
int             *xbm;                       /* bitmap for matching */
long            offset;                     /* current offset in jmp file */
struct  diag    *dx;                        /* holds diagonals */
struct  path    pp[2];                      /* holds path for seqs */
char            *calloc(), *malloc(), *index(), *strcpy();
char            *getseq(), *g_calloc();
```

Page 1 of nw.h

FIGURE 20 C

```c
/* Needleman-Wunsch alignment program
 *
 * usage: progs file1 file2
 *   where file1 and file2 are two dna or two protein sequences.
 *   The sequences can be in upper- or lower-case an may contain ambiguity
 *   Any lines beginning with ';', '>' or '<' are ignored
 *   Max file length is 65535 (limited by unsigned short x in the jmp struct)
 *   A sequence with 1/3 or more of its elements ACGTU is assumed to be DNA
 *   Output is in the file "align.out"
 *
 * The program may create a tmp file in /tmp to hold info about traceback.
 * Original version developed under BSD 4.3 on a vax 8650
 */
include "nw.h"
#include "day.h"

static    _dbval[26] = {
          1,14,2,13,0,0,4,11,0,0,12,0,3,15,0,0,0,5,6,8,8,7,9,0,10,0
};

static    _pbval[26] = {
          1, 2|(1<<('D'-'A'))|(1<<('N'-'A')), 4, 8, 16, 32, 64,
          128, 256, 0xFFFFFFF, 1<<10, 1<<11, 1<<12, 1<<13, 1<<14,
          1<<15, 1<<16, 1<<17, 1<<18, 1<<19, 1<<20, 1<<21, 1<<22,
          1<<23, 1<<24, 1<<25|(1<<('E'-'A'))|(1<<('Q'-'A'))
};

main(ac, av)                                                                    main
          int     ac;
          char    *av[];
{
          prog = av[0];
          if (ac != 3) {
                    fprintf(stderr,"usage: %s file1 file2\n", prog);
                    fprintf(stderr,"where file1 and file2 are two dna or two protein sequences.\n");
                    fprintf(stderr,"The sequences can be in upper- or lower-case\n");
                    fprintf(stderr,"Any lines beginning with ';' or '<' are ignored\n");
                    fprintf(stderr,"Output is in the file \"align.out\"\n");
                    exit(1);
          }
          namex[0] = av[1];
          namex[1] = av[2];
          seqx[0] = getseq(namex[0], &len0);
          seqx[1] = getseq(namex[1], &len1);
          xbm = (dna)? _dbval : _pbval;

endgaps = 0;                    /* 1 to penalize endgaps */
          ofile = "align.out";            /* output file */ nw();                           /* fill in the matrix, get the possible jmps */
          readjmps();                     /* get the actual jmps */
          print();                        /* print stats, alignment */ cleanup(0);                     /* unlink any tmp files */
}
          Page 1 of nw.c
```

FIGURE 20 D

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()                                                                            nw
{
        char       *px, *py;           /* seqs and ptrs */
        int        *ndely, *dely;      /* keep track of dely */
        int        ndelx, delx;        /* keep track of delx */
        int        *tmp;               /* for swapping row0, row1 */
        int        mis;                /* score for each type */
        int        ins0, ins1;         /* insertion penalties */
        register   id;                 /* diagonal index */
        register   ij;                 /* jmp index */
        register   *col0, *col1;       /* score for curr, last row */
        register   xx, yy;             /* index into seqs */ dx = (struct diag *)g_calloc("to get diags", len0+len1+1, sizeof(struct diag));

ndely = (int *)g_calloc("to get ndely", len1+1, sizeof(int));
        dely = (int *)g_calloc("to get dely", len1+1, sizeof(int));
        col0 = (int *)g_calloc("to get col0", len1+1, sizeof(int));
        col1 = (int *)g_calloc("to get col1", len1+1, sizeof(int));
        ins0 = (dna)? DINS0 : PINS0;
        ins1 = (dna)? DINS1 : PINS1;

smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;            /* Waterman Bull Math Biol 84 */
        }
        else
                for (yy = 1; yy <= len1; yy++)
                        dely[yy] = -ins0;

/* fill in match matrix
         */
        for (px = seqx[0], xx = 1; xx <= len0; px++, xx++) {
                /* initialize first entry in col
                 */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;
                }
```

```
for (py = seqx[1], yy = 1; yy <= len1; py++, yy++) {
        mis = col0[yy-1];
        if (dna)
                mis += (xbm[*px-'A']&xbm[*py-'A'])? DMAT : DMIS;
        else
                mis += _day[*px-'A'][*py-'A'];

/* update penalty for del in x seq;
         * favor new del over ongong del
         * ignore MAXGAP if weighting endgaps
         */
        if (endgaps || ndely[yy] < MAXGAP) {
                if (col0[yy] - ins0 >= dely[yy]) {
                        dely[yy] = col0[yy] - (ins0+ins1);
                        ndely[yy] = 1;
                } else {
                        dely[yy] -= ins1;
                        ndely[yy]++;
                }
        } else {
                if (col0[yy] - (ins0+ins1) >= dely[yy]) {
                        dely[yy] = col0[yy] - (ins0+ins1);
                        ndely[yy] = 1;
                } else
                        ndely[yy]++;
        }

/* update penalty for del in y seq;
         * favor new del over ongong del
         */
        if (endgaps || ndelx < MAXGAP) {
                if (col1[yy-1] - ins0 >= delx) {
                        delx = col1[yy-1] - (ins0+ins1);
                        ndelx = 1;
                } else {
                        delx -= ins1;
                        ndelx++;
                }
        } else {
                if (col1[yy-1] - (ins0+ins1) >= delx) {
                        delx = col1[yy-1] - (ins0+ins1);
                        ndelx = 1;
                } else
                        ndelx++;
        }

/* pick the maximum score; we're favoring
         * mis over any del and delx over dely
         */
```

Page 3 of nw.c

```
                    id = xx - yy + len1 - 1;
                    if (mis >= delx && mis >= dely[yy])
                            col1[yy] = mis;
                    else if (delx >= dely[yy]) {
                            col1[yy] = delx;
                            ij = dx[id].ijmp;
                            if (dx[id].jp.n[0] && (!dna || (ndelx >= MAXJMP
                                    && xx > dx[id].jp.x[ij]+MX) || mis > dx[id].score+DINS0)) {
                                            dx[id].ijmp++;
                                            if (++ij >= MAXJMP) {
                                                    writejmps(id);
                                                    ij = dx[id].ijmp = 0;
                                                    dx[id].offset = offset;
                                                    offset += sizeof(struct jmp) + sizeof(offset);
                                            }
                            }
                            dx[id].jp.n[ij] = ndelx;
                            dx[id].jp.x[ij] = xx;
                            dx[id].score = delx;
                    }
                    else {
                            col1[yy] = dely[yy];
                            ij = dx[id].ijmp;
        if (dx[id].jp.n[0] && (!dna || (ndely[yy] >= MAXJMP
                            && xx > dx[id].jp.x[ij]+MX) || mis > dx[id].score+DINS0)) {
                            dx[id].ijmp++;
                            if (++ij >= MAXJMP) {
                                    writejmps(id);
                                    ij = dx[id].ijmp = 0;
                                    dx[id].offset = offset;
                                    offset += sizeof(struct jmp) + sizeof(offset);
                            }
        }
                            dx[id].jp.n[ij] = -ndely[yy];
                            dx[id].jp.x[ij] = xx;
                            dx[id].score = dely[yy];
                    }
                    if (xx == len0 && yy < len1) {
                            /* last col
                            */
                            if (endgaps)
                                    col1[yy] -= ins0+ins1*(len1-yy);
                            if (col1[yy] > smax) {
                                    smax = col1[yy];
                                    dmax = id;
                            }
                    }
            }
            if (endgaps && xx < len0)
                    col1[yy-1] -= ins0+ins1*(len0-xx);
            if (col1[yy-1] > smax) {
                    smax = col1[yy-1];
                    dmax = id;
            }
            tmp = col0; col0 = col1; col1 = tmp;
    }
    (void) free((char *)ndely);
    (void) free((char *)dely);
    (void) free((char *)col0);
    (void) free((char *)col1);}       Page 4 of nw.c
```

FIGURE 20 G

```
/*
*
* print() -- only routine visible outside this module
*
* static:
* getmat() -- trace back best path, count matches: print()
* pr_align() -- print alignment of described in array p[]: print()
* dumpblock() -- dump a block of lines with numbers, stars: pr_align()
* nums() -- put out a number line: dumpblock()
* putline() -- put out a line (name, [num], seq, [num]): dumpblock()
* stars() - -put a line of stars: dumpblock()
* stripname() -- strip any path and prefix from a seqname
*/ include "nw.h"

define SPC      3
#define P_LINE   256    /* maximum output line */
define P_SPC    3      /* space between name or num and seq */ extern   _day[26][26];
int      olen;          /* set output line length */
FILE     *fx;           /* output file */ print()                                                              print
{
        int     lx, ly, firstgap, lastgap;     /* overlap */ if ((fx = fopen(ofile, "w")) == 0) {
                fprintf(stderr,"%s: can't write %s\n", prog, ofile);
                cleanup(1);
        }
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 - 1) {           /* leading gap in x */
                pp[0].spc = firstgap = len1 - dmax - 1;
                ly -= pp[0].spc;
        }
        else if (dmax > len1 - 1) {      /* leading gap in y */
                pp[1].spc = firstgap = dmax - (len1 - 1);
                lx -= pp[1].spc;
        }
        if (dmax0 < len0 - 1) {          /* trailing gap in x */
                lastgap = len0 - dmax0 -1;
                lx -= lastgap;
        }
        else if (dmax0 > len0 - 1) {     /* trailing gap in y */
                lastgap = dmax0 - (len0 - 1);
                ly -= lastgap;
        }
        getmat(lx, ly, firstgap, lastgap);
        pr_align();
}

Page 1 of nwprint.c
```

FIGURE 20 H

```
/*
 * trace back the best path, count matches
 */
static
getmat(lx, ly, firstgap, lastgap)                                              getmat
        int     lx, ly;                 /* "core" (minus endgaps) */
        int     firstgap, lastgap;      /* leading trailing overlap */
{
        int             nm, i0, i1, siz0, siz1;
        char            outx[32];
        double          pct;
        register        n0, n1;
        register char   *p0, *p1;

/* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;

nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }

/* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
```

FIGURE 20 I

...getmat

```c
        fprintf(fx, "<gaps in first sequence: %d", gapx);
        if (gapx) {
                (void) sprintf(outx, " (%d %s%s)",
                        ngapx, (dna)? "base":"residue", (ngapx == 1)? "":"s");
                fprintf(fx,"%s", outx);
        } fprintf(fx, ", gaps in second sequence: %d", gapy);
        if (gapy) {
                (void) sprintf(outx, " (%d %s%s)",
                        ngapy, (dna)? "base":"residue", (ngapy == 1)? "":"s");
                fprintf(fx,"%s", outx);
        }
        if (dna)
                fprintf(fx,
                "\n<score: %d (match = %d, mismatch = %d, gap penalty = %d + %d per base)\n",
                smax, DMAT, DMIS, DINS0, DINS1);
        else
                fprintf(fx,
                "\n<score: %d (Dayhoff PAM 250 matrix, gap penalty = %d + %d per residue)\n",
                smax, PINS0, PINS1);
        if (endgaps)
                fprintf(fx,
                "<endgaps penalized. left endgap: %d %s%s, right endgap: %d %s%s\n",
                firstgap, (dna)? "base" : "residue", (firstgap == 1)? "" : "s",
                lastgap, (dna)? "base" : "residue", (lastgap == 1)? "" : "s");
        else
                fprintf(fx, "<endgaps not penalized\n");
} static          nm;             /* matches in core -- for checking */
static          lmax;           /* lengths of stripped file names */
static          ij[2];          /* jmp index for a path */
static          nc[2];          /* number at start of current line */
static          ni[2];          /* current elem number -- for gapping */
static          siz[2];
static char     *ps[2];         /* ptr to current element */
static char     *po[2];         /* ptr to next output char slot */
static char     out[2][P_LINE]; /* output line */
static char     star[P_LINE];   /* set by stars() */

/*
* print alignment of described in struct path pp[]
*/
static
pr_align()                                                              pr_align
{
        int     nn;     /* char count */
        int     more;
        register i;

for (i = 0, lmax = 0; i < 2; i++) {
                nn = stripname(namex[i]);
                if (nn > lmax)
                        lmax = nn;

nc[i] = 1;
                ni[i] = 1;
                siz[i] = ij[i] = 0;
                ps[i] = seqx[i];
                po[i] = out[i];
        }
Page 3 of nwprint.c
```

FIGURE 20 J

```
for (nn = nm = 0, more = 1; more; ) {                                          ...pr_align
        for (i = more = 0; i < 2; i++) {
                /*
                 * do we have more of this sequence?
                 */
                if (!*ps[i])
                        continue;

more++;

if (pp[i].spc) {       /* leading space */
                        *po[i]++ = ' ';
                        pp[i].spc--;
                }
                else if (siz[i]) {     /* in a gap */
                        *po[i]++ = '-';
                        siz[i]--;
                }
                else {                 /* we're putting a seq element
                                        */
                        *po[i] = *ps[i];
                        if (islower(*ps[i]))
                                *ps[i] = toupper(*ps[i]);
                        po[i]++;
                        ps[i]++;

/*
                         * are we at next gap for this seq?
                         */
                        if (ni[i] == pp[i].x[ij[i]]) {
                                /*
                                 * we need to merge all gaps
                                 * at this location
                                 */
                                siz[i] = pp[i].n[ij[i]++];
                                while (ni[i] == pp[i].x[ij[i]])
                                        siz[i] += pp[i].n[ij[i]++];
                        }
                        ni[i]++;
                }
        }
        if (++nn == olen || !more && nn) {
                dumpblock();
                for (i = 0; i < 2; i++)
                        po[i] = out[i];
                nn = 0;
        }
    }
}
/*
 * dump a block of lines, including numbers, stars: pr_align()
 */
static
dumpblock()                                                                    dumpblock
{
        register i;

for (i = 0; i < 2; i++)
                *po[i]-- = '\0';
Page 4 of nwprint.c
```

FIGURE 20 K

...dumpblock

```
                (void) putc('\n', fx);
                for (i = 0; i < 2; i++) {
                        if (*out[i] && (*out[i] !=' ' || *(po[i]) != ' ')) {
                                if (i == 0)
                                        nums(i);
                                if (i == 0 && *out[1])
                                        stars();
                                putline(i);
                                if (i == 0 && *out[1])
                                        fprintf(fx, star);
                                if (i == 1)
                                        nums(i);
                        }
                }
        }

/*
 * put out a number line: dumpblock()
 */
static
nums(ix)
```
nums
```
        int     ix;     /* index in out[] holding seq line */
{
        char            nline[P_LINE];
        register        i, j;
        register char   *pn, *px, *py;

for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px--)
                                        *px = j%10 + '0';
                                if (i < 0)
                                        *px = '-';
                        }
                        else
                                *pn = ' ';
                        i++;
                }
        }
        *pn = '\0';
        nc[ix] = i;
        for (pn = nline; *pn; pn++)
                (void) putc(*pn, fx);
        (void) putc('\n', fx);
}

/*
 * put out a line (name, [num], seq, [num]): dumpblock()
 */
static
putline(ix)
```
putline
```
        int     ix;
{
```
Page 5 of nwprint.c

FIGURE 20 L

...putline

```
        int             i;
        register char   *px;
        for (px = namex[ix], i = 0; *px && *px != ':'; px++, i++)
                (void) putc(*px, fx);
        for (; i < lmax+P_SPC; i++)
                (void) putc(' ', fx);

/* these count from 1:
         * ni[] is current element (from 1)
         * nc[] is number at start of current line
         */
        for (px = out[ix]; *px; px++)
                (void) putc(*px&0x7F, fx);
        (void) putc('\n', fx);
}

/*
 * put a line of stars (seqs always in out[0], out[1]): dumpblock()
 */
static
stars()                                                                          stars
{
        int             i;
        register char   *p0, *p1, cx, *px;

if (!*out[0] || (*out[0] == ' ' && *(po[0]) == ' ') ||
            !*out[1] || (*out[1] == ' ' && *(po[1]) == ' '))
                return;
        px = star;
        for (i = lmax+P_SPC; i; i--)
                *px++ = ' ';

for (p0 = out[0], p1 = out[1]; *p0 && *p1; p0++, p1++) {
                if (isalpha(*p0) && isalpha(*p1)) { if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
```

Page 6 of nwprint.c

FIGURE 20 M

```
/*
 * strip path or prefix from pn, return len: pr_align()
 */
static
stripname(pn)
        char    *pn;    /* file name (may be path) */
{
        register char   *px, *py;

py = 0;
        for (px = pn; *px; px++)
                if (*px == '/')
                        py = px + 1;
        if (py)
                (void) strcpy(pn, py);
        return(strlen(pn));

}
``` stripname

Page 7 of nwprint.c

FIGURE 20 N

```
/*
 * cleanup() -- cleanup any tmp file
 * getseq() -- read in seq, set dna, len, maxlen
 * g_calloc() -- calloc() with error checkin
 * readjmps() -- get the good jmps, from tmp file if necessary
 * writejmps() -- write a filled array of jmps to a tmp file: nw()
 */
include "nw.h"
include <sys/file.h> char      *jname = "/tmp/homgXXXXXX";         /* tmp file for jmps */
FILE      *fj;

int       cleanup();                          /* cleanup tmp file */
long      lseek();

/*
 * remove any tmp file if we blow
 */
cleanup(i)                                                              cleanup
          int      i;
{
          if (fj)
                   (void) unlink(jname);
          exit(i);
}

/*
 * read, return ptr to seq, set dna, len, maxlen
 * skip lines starting with ';', '<', or '>'
 * seq in upper or lower case
 */
char     *
getseq(file, len)                                                       getseq
          char     *file;       /* file name */
          int      *len;        /* seq len */
{
          char             line[1024], *pseq;
          register char    *px, *py;
          int              natgc, tlen;
          FILE             *fp;

if ((fp = fopen(file,"r")) == 0) {
                   fprintf(stderr,"%s: can't read %s\n", prog, file);
                   exit(1);
          }
          tlen = natgc = 0;
          while (fgets(line, 1024, fp)) {
                   if (*line == ';' || *line == '<' || *line == '>')
                            continue;
                   for (px = line; *px != '\n'; px++)
                            if (isupper(*px) || islower(*px))
                                     tlen++;
          }
          if ((pseq = malloc((unsigned)(tlen+6))) == 0) {
                   fprintf(stderr,"%s: malloc() failed to get %d bytes for %s\n", prog, tlen+6, file);
                   exit(1);
          }
          pseq[0] = pseq[1] = pseq[2] = pseq[3] = '\0';
```

Page 1 of nwsubr.c

FIGURE 20 O

...getseq

```
        py = pseq + 4;
        *len = tlen;
        rewind(fp);

while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU",*(py-1)))
                                natgc++;
                }
        }
        *py++ = '\0';
        *py = '\0';
        (void) fclose(fp);
        dna = natgc > (tlen/3);
        return(pseq+4);
} char    *
g_calloc(msg, nx, sz)                                                        g_calloc
        char    *msg;           /* program, calling routine */
        int     nx, sz;         /* number and size of elements */
{
        char    *px, *calloc();

if ((px = calloc((unsigned)nx, (unsigned)sz)) == 0) {
                if (*msg) {
                        fprintf(stderr, "%s: g_calloc() failed %s (n=%d, sz=%d)\n", prog, msg, nx, sz);
                        exit(1);
                }
        }
        return(px);
}

/*
* get final jmps from dx[] or tmp file, set pp[], reset dmax: main()
*/
readjmps()                                                                   readjmps
{
        int             fd = -1;
        int             siz, i0, i1;
        register  i, j, xx;

if (fj) {
                (void) fclose(fj);
                if ((fd = open(jname, O_RDONLY, 0)) < 0) {
                        fprintf(stderr, "%s: can't open() %s\n", prog, jname);
                        cleanup(1);
                }
        }
        for (i = i0 = i1 = 0, dmax0 = dmax, xx = len0; ; i++) {
                while (1) {
                        for (j = dx[dmax].ijmp; j >= 0 && dx[dmax].jp.x[j] >= xx; j--)
                                ;
```

Page 2 of nwsubr.c

FIGURE 20 P

...readjmps

```
                if (j < 0 && dx[dmax].offset && fj) {
                        (void) lseek(fd, dx[dmax].offset, 0);
                        (void) read(fd, (char *)&dx[dmax].jp, sizeof(struct jmp));
                        (void) read(fd, (char *)&dx[dmax].offset, sizeof(dx[dmax].offset));
                        dx[dmax].ijmp = MAXJMP-1;
                }
                else
                        break;
        }
        if (i >= JMPS) {
                fprintf(stderr, "%s: too many gaps in alignment\n", prog);
                cleanup(1);
        }
        if (j >= 0) {
                siz = dx[dmax].jp.n[j];
                xx = dx[dmax].jp.x[j];
                dmax += siz;
                if (siz < 0) {                  /* gap in second seq */
                        pp[1].n[i1] = -siz;
                        xx += siz;
                        /* id = xx - yy + len1 - 1
                         */
                        pp[1].x[i1] = xx - dmax + len1 - 1;
                        gapy++;
                        ngapy -= siz;
/* ignore MAXGAP when doing endgaps */
                        siz = (-siz < MAXGAP || endgaps)? -siz : MAXGAP;
                        i1++;
                }
                else if (siz > 0) {     /* gap in first seq */
                        pp[0].n[i0] = siz;
                        pp[0].x[i0] = xx;
                        gapx++;
                        ngapx += siz;
/* ignore MAXGAP when doing endgaps */
                        siz = (siz < MAXGAP || endgaps)? siz : MAXGAP;
                        i0++;
                }
        }
        else
                break;
}
/* reverse the order of jmps
 */
for (j = 0, i0--; j < i0; j++, i0--) {
        i = pp[0].n[j]; pp[0].n[j] = pp[0].n[i0]; pp[0].n[i0] = i;
        i = pp[0].x[j]; pp[0].x[j] = pp[0].x[i0]; pp[0].x[i0] = i;
}
for (j = 0, i1--; j < i1; j++, i1--) {
        i = pp[1].n[j]; pp[1].n[j] = pp[1].n[i1]; pp[1].n[i1] = i;
        i = pp[1].x[j]; pp[1].x[j] = pp[1].x[i1]; pp[1].x[i1] = i;
}
if (fd >= 0)
        (void) close(fd);
if (fj) {
        (void) unlink(jname);
        fj = 0;
        offset = 0;
}
}
```

Page 3 of nwsubr.c

FIGURE 20 Q

```
/*
 * write a filled jmp struct offset of the prev one (if any): nw()
 */
writejmps(ix)                                                                    writejmps
        int     ix;
{
        char    *mktemp();

if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}

Page 4 of nwsubr.c
```

FIGURE 24
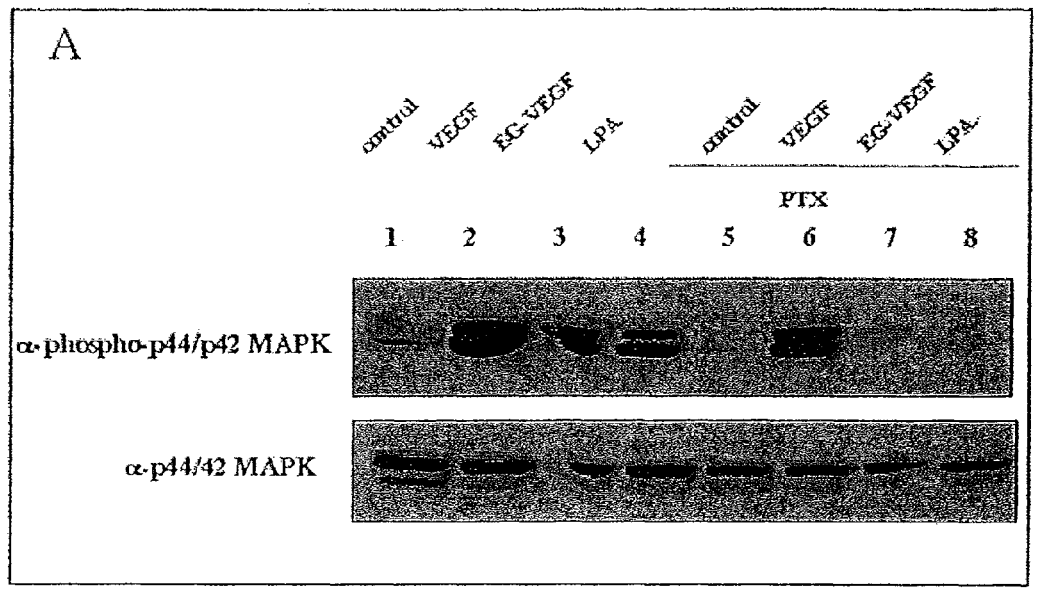
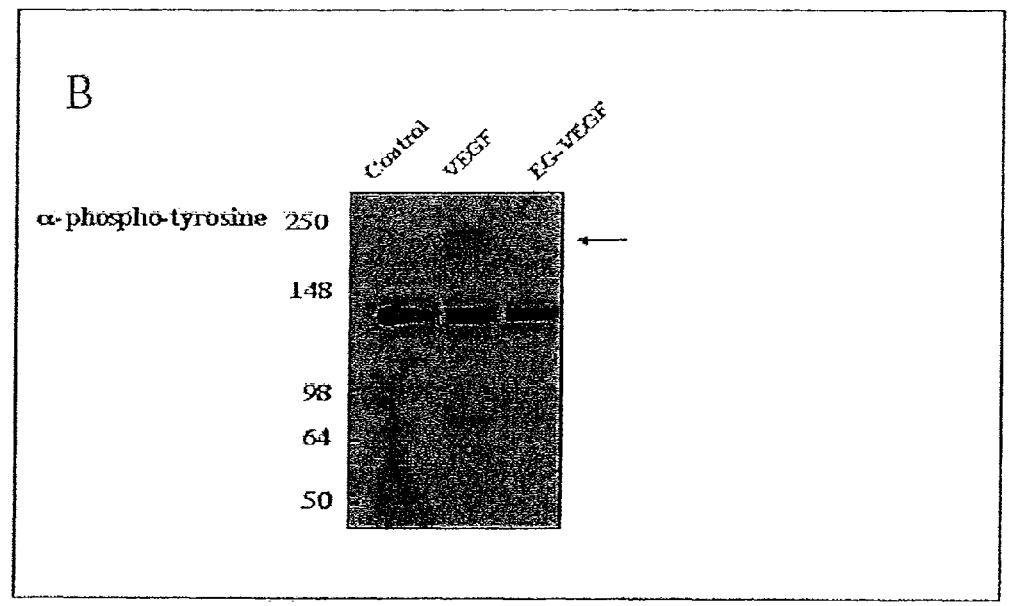

Figure 26A-E

EG-VEGF NUCLEIC ACIDS AND POLYPEPTIDES AND METHODS OF USE

This application is a divisional of U.S. application Ser. No. 11/537,472 filed Sep. 29, 2006, now U.S. Pat. No. 7,736,645 which is a continuation of U.S. application Ser. No. 10/027,603 filed Dec. 19, 2001, now U.S. Pat. No. 7,264,801, which is a continuation-in-part of application Ser. No. 09/886,242 filed on Jun. 20, 2001 (abandoned), which claims priority to U.S. Provisional Application Nos. 60/230,978 filed on Sep. 7, 2000 and 60/213,637 filed on Jun. 23, 2000. Application Ser. No. 09/886,242 is a continuation-in-part of international Application No. PCT/US00/32678 filed on Dec. 1, 2000, and is a continuation-in-part of international Application No. PCT/US00/08439 filed on Mar. 30, 2000, and is a continuation-in-part application of PCT Application No. PCT/US00/04914 filed on Feb. 24, 2000, and is a continuation-in-part of PCT Application No. PCT/US00/00219 filed on Jan. 5, 2000. The PCT/US00/0219 application claims priority to U.S. Provisional Application No. 60/145,698 filed on Jul. 26, 1999. The Ser. No. 09/886,242 application is a continuation-in-part of Ser. No. 09/709,238 filed on Nov. 8, 2000 (abandoned), which is a continuation of application Ser. No. 09/380,137 filed on Aug. 25, 1999 (abandoned), which is a national phase application of international application No. PCT/US99/12252, Jun. 2, 1999 which claims priority to U.S. Provisional Application No. 60/096,146 filed on Aug. 11, 1998, each of which are incorporated by reference herein in their entireties.

FIELD OF THE INVENTION

The present invention relates generally to the identification and isolation of novel DNA and to the recombinant production of novel polypeptides, designated herein as endocrine gland-derived vascular endothelial growth factors (EG-VEGF), earlier called endocrine gland-derived endothelial cell growth factors (EG-ECGF), previously also referred to as "VRPA" polypeptides and polypeptides encoded by "DNA60621-1516". The present invention also relates to methods, compositions and assays utilizing such polypeptides for
producing pharmaceutically active materials having therapeutic and pharmacological properties.

BACKGROUND OF THE INVENTION

Endothelial Cells

The local microenvironment profoundly affects the phenotype and growth properties of vascular endothelial cells in a tissue- or organ-specific manner, but the nature of the local instructive signals is largely unknown. There is compelling evidence that the vascular endothelial growth factor (VEGF) and angiopoietin families of endothelial cell specific growth factors are essential for embryonic development and for angiogenesis in a variety of physiological and pathological circumstances [Ferrara and Alitalo, *Nature Medicine*, 5:1359-1364 (1999); Carmeliet, *Nature Medicine*, 6:389-395 (2000)]. There is also strong evidence for a local, tissue-specific, regulation of endothelial cell phenotype and growth [Aird et al., *J. Cell Biol.*, 138:1117-1124 (1997); Stewart and Wiley, *Dev. Biol.*, 84:183-192 (1981)]. The morphological and functional characteristics of endothelial cells vary extensively among different organs [Simionescu and Simionescu, *Cell and Tissue Biology*, Urban and Schwarzemberg, Baltimore, (1988) pp. 355-398]. Furthermore, the site of application determines the properties of new vessels to an even greater extent than the type of angiogenic factor tested [Dellian et al., *Am. J. Pathology*, 149:59-71 (1996); Roberts et al., *Am. J. Pathology*, 153:1239-1248 (1998)]. The molecular basis for this influence of the local microenvironment on the properties of the vasculature is unknown, but it is believed that the specialized stroma plays a major role [Dellian, supra]. Conceivably, an integrated network of stimuli, which may include tissue-specific secreted proteins, in addition to cellular and extracellular matrix components, functions to determine the structure and function as well as modulate growth of the resident endothelium.

Thus there is a current need to identify and characterize novel growth and differentiation factors that influence the growth and/or differentiation of endothelial cells. In addition to increasing our knowledge of the development of the vasculature, such compounds could be useful in the diagnosis and treatment of conditions associated with vascular tissue.

Hormone Secreting Cells

While there has been progress in the advancement of science and medical therapies, there is still a need for new treatments for the medical ailments of society. One approach to finding new treatments has been to study how the organism operates. In particular, of interest is how signaling cells control the behavior of the organism. For example, endocrine cells secrete signaling molecules called hormones wherein malfunctioning of secretion of these hormones can lead to a variety of disorders.

Cells specialized for secretion of hormones include the cells of gonads, secreting testosterone (Leydig cell of testis), estrogen (theca interna cell of ovarian follicle) and progesterone (corpus luteum cell of ruptured ovarian follicle). While there are a variety of treatments in the medical field which utilize exogenous administration of testosterone, estrogen and progesterone, there remains a need to regulate the cells which produce these hormones.

Other cells specialized for secretion of hormones include the cells of the adrenal gland and the cells of the digestive system. For example, cells of the adrenal gland secrete epinephrine, norepinephrine and steroid hormones such as mineralocorticoids and glucocorticoids. Of particular interest is cortisol which is produced in the cortex of the adrenal gland and which influences the metabolism of many cell types. Cells of the digestive system include those of the pancreas which secretes insulin. Insulin is secreted by the islets of Langerhans and is essential for the metabolism of carbohydrates. Insulin is used in the treatment and control of diabetes mellitus, however, there is still a need for efficient treatments for disorders such as diabetes. Other hormones of interest of the gut and respiratory tract include serotonin, endorphin, somatostatin, gastrin, secretin, cholecystokinin, glucagon and bombesin.

There are numerous diseases and disorders associated with hormone secreting cells, in particular steroidogenic endothelial cells within endocrine glands. It would, therefore, be desirable to identify growth factors specifically affecting such endothelial cells. Such endothelial cell specific growth factors would be valuable tools for diagnosing and treating disorders associated with such cell types, and for identifying further drug candidates useful in diagnosis and treatment of such diseases.

SUMMARY OF THE INVENTION

The present invention is based on the identification and characterization of a novel, tissue-restricted, growth and differentiation factor that acts selectively on one endothelial cell type. This factor, referred to as endocrine gland-derived vascular endothelial growth factor (EG-VEGF), has been found to induce proliferation, migration and fenestrations in capillary endothelial cells derived from endocrine glands, but has shown no effect on a variety of other endothelial and non-endothelial cell types tested. As described in detail herein, EG-VEGF nucleic acids and polypeptides can be used in a number of assays and in diagnosis and treatment of conditions associated with hormone producing tissue.

In one aspect, the present invention concerns a composition of matter comprising an EG-VEGF polypeptide, or an agonist or antagonist of an EG-VEGF polypeptide, as herein described, in admixture with a pharmaceutically acceptable carrier. In one embodiment, this composition further comprises a vascular endothelial cell growth factor (VEGF) or an agonist or antagonist thereof.

In a further aspect, the present invention provides an article of manufacture comprising a container, a label on the container and a composition comprising an active agent that is contained within the container. The active agent is selected from the group consisting of an EG-VEGF polypeptide, an agonist of an EG-VEGF polypeptide and an antagonist of an EG-VEGF polypeptide. The label on the container indicates that the composition is effective for treating a condition that is associated with a hormone producing endothelial tissue. In one embodiment of this aspect of the invention, the condition is associated with steroidogenic endothelial cells within an endocrine gland. In a second embodiment, the tissue is ovarian, testicular, cervical, adrenal, placental or prostate tissue. The condition may preferably be infertility, polynistic ovary syndrome or cancer.

In another aspect, the present invention provides for a method for identifying a compound that binds to EG-VEGF. This method comprises contacting a candidate compound with EG-VEGF and determining whether the candidate compound binds to the EG-VEGF. In one embodiment, the assay is a competitive binding assay, i.e. the ability of the candidate compound to compete with a molecule known to bind EG-VEGF is measured. The assay may, for example, be a cell-based assay wherein the candidate compound is contacted with a whole cell or a cell membrane fraction expressing the coding sequence of EG-VEGF.

The present invention also concerns a method for identifying a compound that modulates a biological activity of EG-VEGF. This method comprises the steps of contacting a candidate compound with EG-VEGF and determining if an alteration in a biological activity of EG-VEGF has occurred. In one embodiment, the compound inhibits a biological activity of EG-VEGF, and in another embodiment the compound enhances a biological activity of EG-VEGF. The biological activity may, for example, be the ability to induce phosphorylation of a kinase involved in cell proliferation or survival. In a preferred embodiment, the kinase is a MAP kinase, more preferably ERK1 or ERK2. In a further embodiment the biological activity is the ability to phosphorylate Akt and eNOS. In other embodiments, the biological activity is cell proliferation, induction of chemotaxis, angiogenesis, induction of cell differentiation, promotion of cell survival or the induction of endothelial cell fenestration. Just as before, the assay may, for example, be a cell-based assay wherein the candidate molecule is contacted with a whole cell or a cell membrane fraction expressing the coding sequence of EG-VEGF. In a preferred embodiment, the cell is a recombinant host cell engineered to express EG-VEGF. Alternatively, the candidate molecule may be contacted with an isolated EG-VEGF. In a preferred embodiment, the EG-VEGF is immobilized on a solid support.

In another aspect, the invention specifically covers compounds that have been identified by one of the assays described above as having the ability to bind EG-VEGF or modulate a biological activity of EG-VEGF.

Additionally provided herein is a method of identifying a receptor for EG-VEGF. This method comprises combining EG-VEGF with a composition that comprises cell membrane material wherein the EG-VEGF complexes with a receptor on the cell membrane material and the receptor is identified as an EG-VEGF receptor. In one embodiment of this aspect of the invention, EG-VEGF binds to the receptor and EG-VEGF and the receptor are crosslinked.

Another aspect of this invention concerns a method of stimulating a biological activity in cells or tissue. This includes a method of stimulating cell proliferation, a method of inducing chemotaxis in cells, a method of inducing angiogenesis in hormone producing tissue, a method of inducing cell differentiation in cells, a method of enhancing cell survival and a method of inducing fenestration in cells. In each of these methods, the biological activity is stimulated by contacting the cells or tissue with EG-VEGF or an EG-VEGF agonist in an amount effective to induce the desired biological activity, or by introducing a nucleic acid encoding EG-VEGF or an EG-VEGF agonist into the cells or tissue in an amount effective to induce the biological activity. The cells preferably are endothelial cells, in particular hormone producing endothelial cells or tissue.

The invention also provides for methods of inhibiting all of the biological activities described above by contacting the cells or hormone producing tissue with an EG-VEGF antagonist in an amount effective to inhibit the biological activity, or by introducing a nucleic acid encoding an EG-VEGF antagonist into the cells.

An additional aspect of the invention provides for methods of treating individuals. These methods include a method for treating an individual for a condition associated with hormone producing tissue, a method for regulating fertility in an individual, a method of treating cancer in cells responsive to EG-VEGF in an individual, a method of treating cancer of the reproductive organs in an individual, and a method of treating an ovarian cyst in an individual. In one embodiment of the methods of this aspect of the invention, the methods comprise administering to the individual a composition comprising EG-VEGF or an agonist or antagonist thereof in an amount effective to treat the condition, regulate fertility, treat the cancer or treat the ovarian cyst. In another embodiment, the method comprises administering to the individual a composition comprising a nucleic acid encoding EG-VEGF or an agonist or antagonist thereof in an amount effective to treat the condition. In a particular embodiment, fertility is regulated by inhibiting follicle maturation. In a further embodiment, fertility is regulated by inhibiting ovulation. In another embodiment the individual has or is at risk of having polycystic ovary syndrome and fertility is regulated so as to maintain fertility. The cancer to be treated may, for example, be ovarian cancer, testicular cancer, prostate cancer, or uterine cancer.

The preferred embodiments described below apply to all aspects of the invention.

In one embodiment, EG-VEGF polypeptide is a native sequence EG-VEGF. In a further embodiment the native sequence EG-VEGF is human. In another embodiment, the EG-VEGF is a fragment of a native sequence EG-VEGF. In still another embodiment, the EG-VEGF is an amino acid sequence variant of a native sequence EG-VEGF, which preferably has at least about 85% sequence identity to the sequence of amino acid residues from about 1 or about 20 to about 105, inclusive, of FIG. 2 (SEQ ID NO: 2). In yet another embodiment, the amino acid sequence variant is a conservative substitution variant. In another embodiment the EG-VEGF is a fragment of an amino acid sequence variant of a native sequence EG-VEGF. In another embodiment the EG-VEGF is present as a fusion protein.

The compositions and methods described above may further involve the use of a VEGF polypeptide. In one embodiment, the VEGF polypeptide is a native sequence VEGF. In a further embodiment the native sequence VEGF is human. In another embodiment, the VEGF is a fragment of a native sequence VEGF. In still another embodiment, the VEGF is an amino acid sequence variant of a native sequence VEGF. In a further embodiment the amino acid sequence variant has at least about 85% sequence identity to the sequence of native sequence VEGF. In yet another embodiment, the amino acid sequence variant is a conservative substitution variant. In another embodiment the VEGF is a fragment of an amino acid sequence variant of a native sequence VEGF. In another embodiment the VEGF is present as a fusion protein.

In one embodiment, the EG-VEGF agonist or VEGF agonist is an anti-EG-VEGF antibody or anti-VEGF antibody, respectively, specifically including antibody fragments. In another embodiment, the EG-VEGF or VEGF agonist is a small molecule.

Similarly, the EG-VEGF or VEGF antagonist may, for example be an anti-EG-VEGF or anti-VEGF antibody, respectively, specifically including antibody fragments. In another embodiment the EG-VEGF or VEGF antagonist is a small molecule.

In one embodiment, the whole cell or cell membrane fraction expressing the coding sequence of EG-VEGF is a recombinant host cell engineered to express EG-VEGF.

The invention further concerns anti-EG-VEGF antibodies, in particular anti-EG-VEGF monoclonal antibodies 1C6, 2A3, 2A8 and 4H9, and antibodies that bind essentially the same epitope(s) as any of these antibodies. Fragments of such antibodies, as well as chimeric, humanized, or human antibodies sharing an epitope with any of monoclonal antibodies 1C6, 2A3, 2A8 and 4H9 are specifically included herein, as are antibody variants comprising amino acid alterations (substitutions, insertions and/or deletions) within the sequence, including the variable region, of such antibodies, as long as the antibodies retain the qualitative antigen-binding properties of any of monoclonal antibodies 1C6, 2A3, 2A8 and 4H9.

Other embodiments and variations of the present invention will become apparent by the description of the invention given in detail below.

BRIEF DESCRIPTION OF THE DRAWINGS

FIG. 1 shows the nucleotide sequence (SEQ ID NO:1) of a cDNA containing a nucleotide sequence (nucleotides 91-405) encoding native sequence EG-VEGF, wherein the nucleotide sequence (SEQ ID NO:1) is a clone designated herein as cDNA60621-1516". Also presented in bold font and underlined are the positions of the respective start and stop codons.

FIG. 2 shows the amino acid sequence (SEQ ID NO:2) of a native sequence EG-VEGF polypeptide as derived from the coding sequence of SEQ ID NO:1. Also shown are the approximate locations of various other important polypeptide domains.

FIGS. 3A-D show hypothetical exemplifications for using the below described method to determine % amino acid sequence identity (FIGS. 3A-B) and % nucleic acid sequence identity (FIGS. 3C-D) using the ALIGN-2 sequence comparison computer program, wherein "PRO" represents the amino acid sequence of a hypothetical EG-VEGF polypeptide of interest, "Comparison Protein" represents the amino acid sequence of a polypeptide against which the "PRO" polypeptide of interest is being compared, "PRO-DNA" represents a hypothetical EG-VEGF-encoding nucleic acid sequence of interest, "Comparison DNA" represents the nucleotide sequence of a nucleic acid molecule against which the "PRO-DNA" nucleic acid molecule of interest is being compared, "X", "Y" and "Z" each represent different hypothetical amino acid residues and "N", "L" and "V" each represent different hypothetical nucleotides.

FIG. 4 shows a nucleotide sequence designated herein as DNA56748 (SEQ ID NO:3).

FIGS. 5A and 5B show 2-year-old chimp ovary where FIG. 5A shows a hematoxylin-eosin stain and FIG. 5B shows expression using FITC. FIGS. 5C and 5D show cyno monkey ovary where FIG. 5C shows a hematoxylin-eosin stain and FIG. 5D shows EG-ECGF expression using FITC. FIGS. 5E and 5F show chimp stromal ovary where FIG. 5E shows a hematoxylin-eosin stain and FIG. 5F shows EG-ECGF expression using FITC.

FIG. 6A shows a hematoxylin-eosin stain and FIG. 6B shows EG-ECGF expression using FITC. FIG. 6C shows a hematoxylin-eosin stain and FIG. 6D shows EG-ECGF expression using FITC.

FIGS. 8A and 8B show nucleic acid identification using DAPI and FIGS. 8C and 8D show protein identification using FITC.

FIG. 12A shows the results using pericytes. FIG. 12B shows the results using human aortic vascular smooth muscle cells (HA-VSMC). FIG. 12C shows the results using baby hamster kidney fibroblasts (BHK21). FIG. 12D shows the results using ACE. FIG. 12E shows the results using bovine brain capillary endothelial cells (BBC).

FIG. 13 shows that EG-VEGF is a mitogen and chemoattractant for specific endothelial cells. Panel a shows that in ACE cultures, EG-VEGF induced a maximal mitogenic response at 2 nM, with an $ED_{50}$ of 0.2 nM. Panel b shows the results of proliferation assays with several endothelial cell types: HUVEC, HMVEC, BBC, ABAE. Panel c shows the results of proliferation assays with non-endothelial cell types: human aortic vascular smooth muscle cells (VSMC), pericytes and fibroblasts (BHK21) and human neonatal fibroblasts—hFb) and keratinocytes. Basal media served as a negative control (Ct); bFGF (F), EGF (E), or VEGF (V), added respectively at 5.5 and 10 ng'ml, served as positive controls. EG-VEGF was tested at 1, 10, and 100 nM. Panel d shows that EG-VEGF induced a chemotactic response in ACE cells, primary baboon adrenal endothelial cells (BAEC) and MS-1, but not in HUVEC. Each graph is a representative experiment. Data are mean values with error bars indicating standard deviation, and the proliferation or migration index is relative to the negative control arbitrarily set to the value 1. Panels e-g illustrate that EG-VEGF induces fenestration in adrenal cortex-derived capillary endothelial cells. ACE, growth to confluence on ECM, were treated with 2.5 nM VEGF, 10 nM EG-VEGF, or the combination of the two factors. Electron micrographs of ACE cells untreated (panel e), treated with VEGF (panel f), or EG-VEGF (panel g) revealed that both molecules are capable of inducing fenestrae. Arrowheads indicate the locations of fenestrae. Magnification is indicated (e and f μm; g nm).

FIGS. 16A-C show EG-VEGF cDNA and amino acid sequences and alignments with homologous proteins. FIG. 16A shows the 1.4 kb human EG-VEGF cDNA sequence. The 1.4 kb human EG-VEGF cDNA encodes a protein of 105 amino acids, with a classical signal sequence of 19 amino acids (underlined), and a mature protein of 86 amino acids. A striking feature of the primary protein structure is the cysteine content, 10 residues that potentially form 5 disulfide bridges. FIG. 16B shows an alignment of the sequences of human EG-VEGF, human Bv8 homologue (SEQ ID NO: 4), and snake VPRA (SEQ ID NO: 5). Boxed residues indicate identity. FIG. 16C is an alignment of human EG-VEGF, human dickkopf-3 (hdkk3, SEQ ID NO: 6), *Xenopus* dkk-1 (xdkk1, SEQ ID NO: 7) and porcine colipase (col, SEQ ID NO: 8). The alignment illustrates the conserved cysteines that form the characteristic disulfide-bonding pattern of this protein domain—the colipase fold. This motif in EG-VEGF is 37% identical and 41% homologous to the cysteine-rich C-terminal domain of human dkk-3; and 32% identical, 42% homologous to the *Xenopus* dkk-1 domain. Numbers indicate a position in the respective protein and bozed residues are identical to EG-VEGF.

FIG. 17A shows Taqman analysis of RNA from SW13 (closed box) and H295 (open box) adrenal carcinoma cells exposed to normoxic (22% $O_2$) versus hypoxic (2% $O_2$) conditions for 18 hours revealed that EG-VEGF transcription increased 275% and 210% in SW13 and H295R, respectively, comparable to the 350% and 252% increases in VEGF over the normoxic controls. VEGF and EG-VEGF data was normalized to β-actin. FIG. 17B shows HRE luciferase activities in normoxic (open box) versus hypoxic (closed box) conditions. Activities of luciferase reporters and vector were normalized to the co-transfected *Renilla* luciferase. Both the Epo consensus and EG-VEGF constructs were induced approximately 3.4-fold in hypoxia above their respective normoxic controls. Mutation of the core sequence, in Epomutant and EG-VEGFmutant, abrogated the responsiveness to hypoxic conditions, resulting in activities similar to vector control.

FIGS. 20A-P provide the complete source code for the ALIGN-2 sequence comparison computer program. This source code may be routinely compiled for use on a UNIX operating system to provide the ALIGN-2 sequence comparison computer program.

FIGS. 24A-B show that EG-VEGF-induced p44/42 MAPK activation is PTX-sensitive. (A) Subconfluent ACE cells were serum starved overnight and pre-treated with 200 n/ml PTX for 1 hour (lanes 5-8), then incubated 10 minutes at 37° C. with 0.5 nM VEGF (lanes 2 and 6), 20 nM EG-VEGF (lanes 3 and 7), 20 nM LPA (lanes 4 and 8) or left untreated (lanes 1 and 5). Cell lysates were electrophoresed, transferred and probed with phospho-p44/43 MAPK (upper panel and p44/42 MAPK protein (lower panel). (B) Confluent ACE cells in 150 mm tissue culture plates were serum starved overnight and stimulated with 20 ng/ml VEGF or 20 nM EG-VEGF for 10 minutes. Cell lysates were incubated with wheat-germ agglutinin beads. The lectin complex was Western-blotted and probed with phospho-tyrosine antibody 4G10. Non-stimulated ACE cell lysate was used as a negative control. The arrow indicates phosphorylated-KDR.

DETAILED DESCRIPTION OF THE PREFERRED EMBODIMENTS

I. Definitions

Figure 5A:
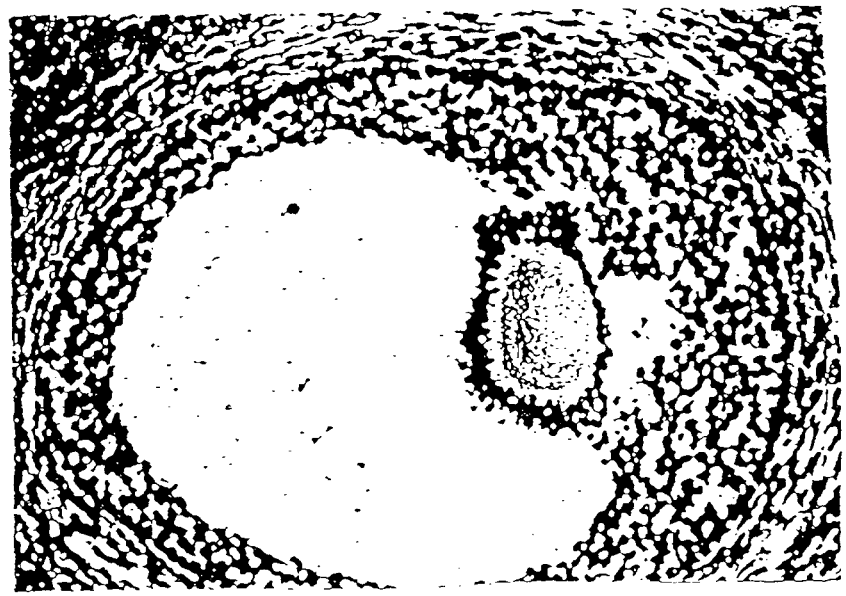
FIGS. 5A-5F show EG-ECGF in situ expression in ovaries.

Unless defined otherwise, technical and scientific terms used herein have the same meaning as commonly understood by one of ordinary skill in the art to which this invention belongs. See, e.g. Singleton et al., *Dictionary of Microbiology and Molecular Biology* 2nd ed., J. Wiley & Sons (New York, N.Y. 1994); Sambrook et al., *Molecular Cloning, A Laboratory Manual*, Cold Springs Harbor Press (Cold Springs Harbor, N.Y. 1989). For purposes of the present invention, the following terms are defined below.

The terms "EG-VEGF polypeptide", "EG-VEGF protein" and "EG-VEGF" (and also "VRPA polypeptide", "VRPA protein" and "VRPA", terms used earlier to describe the same polypeptides) when used herein encompass native sequence EG-VEGF and EG-VEGF polypeptide variants (which are further defined herein). The EG-VEGF polypeptide may be isolated from a variety of sources, such as from human tissue types or from another source, or prepared by recombinant and/or synthetic methods.

A "native sequence EG-VEGF" comprises a polypeptide having the same amino acid sequence as an EG-VEGF derived from nature. Such native sequence EG-VEGF can be isolated from nature or can be produced by recombinant and/or synthetic means. The term "native sequence EG-VEGF" specifically encompasses naturally-occurring truncated or secreted forms (e.g., an extracellular domain sequence), naturally-occurring variant forms (e.g., alternatively spliced forms) and naturally-occurring allelic variants of the EG-VEGF. In one embodiment of the invention, the native sequence EG-VEGF is a mature or full-length native sequence EG-VEGF comprising amino acids 1 to 105 of FIG. 2 (SEQ ID NO:2). Also, while the EG-VEGF polypeptide disclosed in FIG. 2 (SEQ ID NO:2) is shown to begin with the methionine residue designated herein as amino acid position 1, it is conceivable and possible that another methionine residue located either upstream or downstream from amino acid position 1 in FIG. 2 (SEQ ID NO:2) may be employed as the starting amino acid residue for the EG-VEGF polypeptide.

"EG-VEGF variant polypeptide" means an active EG-VEGF polypeptide as defined below having at least about 80% amino acid sequence identity with the amino acid sequence of (a) residues 1 or about 20 to 105 of the EG-VEGF polypeptide shown in FIG. 2 (SEQ ID NO:2), (b) X to 105 of the EG-VEGF polypeptide shown in FIG. 2 (SEQ ID NO:2), wherein X is any amino acid residue from 14 to 24 of FIG. 2 (SEQ ID NO:2), or (c) another specifically derived fragment of the amino acid sequence shown in FIG. 2 (SEQ ID NO:2). Such EG-VEGF variant polypeptides include, for instance, EG-VEGF polypeptides wherein one or more amino acid residues are added, or deleted, at the N- and/or C-terminus, as well as within one or more internal domains, of the sequence of FIG. 2 (SEQ ID NO:2). Ordinarily, a EG-VEGF variant polypeptide will have at least about 80% amino acid sequence identity, more preferably at least about 81% amino acid sequence identity, more preferably at least about 82% amino acid sequence identity, more preferably at least about 83% amino acid sequence identity, more preferably at least about 84% amino acid sequence identity, more preferably at least about 85% amino acid sequence identity, more preferably at least about 86% amino acid sequence identity, more preferably at least about 87% amino acid sequence identity, more preferably at least about 88% amino acid sequence identity, more preferably at least about 89% amino acid sequence identity, more preferably at least about 90% amino acid sequence identity, more preferably at least about 91% amino acid sequence identity, more preferably at least about 92% amino acid sequence identity, more preferably at least about 93% amino acid sequence identity, more preferably at least about 94% amino acid sequence identity, more preferably at least about 95% amino acid sequence identity, more preferably at least about 96% amino acid sequence identity, more preferably at least about 97% amino acid sequence identity, more preferably at least about 98% amino acid sequence identity and yet more preferably at least about 99% amino acid sequence identity with (a) residues 1 or about 20 to 105 of the EG-VEGF polypeptide shown in FIG. 2 (SEQ ID NO:2), (b) X to 105 of the EG-VEGF polypeptide shown in FIG. 2 (SEQ ID NO:2), wherein X is any amino acid residue from 14 to 24 of FIG. 2 (SEQ ID NO:2), or (c) another specifically derived fragment of the amino acid sequence shown in FIG. 2 (SEQ ID NO:2). EG-VEGF variant polypeptides do not encompass the native EG-VEGF polypeptide sequence. Ordinarily, EG-VEGF variant polypeptides are at least about 10 amino acids in length, often at least about 20 amino acids in length, more often at least about 30 amino acids in length, more often at least about 40 amino acids in length, more often at least about 50 amino acids in length, more often at least about 60 amino acids in length, more often at least about 70 amino acids in length, more often at least about 80 amino acids in length, more often at least about 90 amino acids in length, more often at least about 100 amino acids in length, more often at least about 150 amino acids in length, more often at least about 200 amino acids in length, more often at least about 250 amino acids in length, more often at least about 300 amino acids in length, or more.

"Percent (%) amino acid sequence identity" with respect to the EG-VEGF polypeptide sequences identified herein is defined as the percentage of amino acid residues in a candidate sequence that are identical with the amino acid residues in a EG-VEGF sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2, wherein the complete source code for the ALIGN-2 program is provided in FIG. 20. The ALIGN-2 sequence comparison computer program was authored by Genentech, Inc. and the source code shown in FIG. 20 has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided herein. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations, FIGS. 3A-B demonstrate how to calculate the % amino acid sequence identity of the amino acid sequence designated "Comparison Protein" to the amino acid sequence designated "PRO".

Unless specifically stated otherwise, all % amino acid sequence identity values used herein are obtained as described above using the ALIGN-2 sequence comparison computer program. However, % amino acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"EG-VEGF variant polynucleotide" or "EG-VEGF variant nucleic acid sequence" means a nucleic acid molecule which encodes an active EG-VEGF polypeptide as defined below and which has at least about 80% nucleic acid sequence identity with either (a) a nucleic acid sequence which encodes residues 1 or about 20 to 105 of the EG-VEGF polypeptide shown in FIG. 2 (SEQ ID NO:2), (b) a nucleic acid sequence which encodes amino acids X to 105 of the EG-VEGF polypeptide shown in FIG. 2 (SEQ ID NO:2), wherein X is any amino acid residue from 14 to 24 of FIG. 2 (SEQ ID NO:2), or (c) a nucleic acid sequence which encodes another specifically derived fragment of the amino acid sequence shown in FIG. 2 (SEQ ID NO:2). Ordinarily, a EG-VEGF variant polynucleotide will have at least about 80% nucleic acid sequence identity, more preferably at least about 81% nucleic acid sequence identity, more preferably at least about 82% nucleic acid sequence identity, more preferably at least about 83% nucleic acid sequence identity, more preferably at least about 84% nucleic acid sequence identity, more preferably at least about 85% nucleic acid sequence identity, more preferably at least about 86% nucleic acid sequence identity, more preferably at least about 87% nucleic acid sequence identity, more preferably at least about 88% nucleic acid sequence identity, more preferably at least about 89% nucleic acid sequence identity, more preferably at least about 90% nucleic acid sequence identity, more preferably at least about 91% nucleic acid sequence identity, more preferably at least about 92% nucleic acid sequence identity, more preferably at least about 93% nucleic acid sequence identity, more preferably at least about 94% nucleic acid sequence identity, more preferably at least about 95% nucleic acid sequence identity, more preferably at least about 96% nucleic acid sequence identity, more preferably at least about 97% nucleic acid sequence identity, more preferably at least about 98% nucleic acid sequence identity and yet more preferably at least about 99% nucleic acid sequence identity with either (a) a nucleic acid sequence which encodes residues 1 or about 20 to 105 of the EG-VEGF polypeptide shown in FIG. 2 (SEQ ID NO:2), (b) a nucleic acid sequence which encodes amino acids X to 105 of the EG-VEGF polypeptide shown in FIG. 2 (SEQ ID NO:2), wherein X is any amino acid residue from 14 to 24 of FIG. 2 (SEQ ID NO:2), or (c) a nucleic acid sequence which encodes another specifically derived fragment of the amino acid sequence shown in FIG. 2 (SEQ ID NO:2). EG-VEGF polynucleotide variants do not encompass the native EG-VEGF nucleotide sequence.

Ordinarily, EG-VEGF variant polynucleotides are at least about 30 nucleotides in length, often at least about 60 nucleotides in length, more often at least about 90 nucleotides in length, more often at least about 120 nucleotides in length, more often at least about 150 nucleotides in length, more often at least about 180 nucleotides in length, more often at least about 210 nucleotides in length, more often at least about 240 nucleotides in length, more often at least about 270 nucleotides in length, more often at least about 300 nucleotides in length, more often at least about 450 nucleotides in length, more often at least about 600 nucleotides in length, more often at least about 900 nucleotides in length, or more.

"Percent (%) nucleic acid sequence identity" with respect to the EG-VEGF polypeptide-encoding nucleic acid sequences identified herein is defined as the percentage of nucleotides in a candidate sequence that are identical with the nucleotides in a EG-VEGF polypeptide-encoding nucleic acid sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % nucleic acid sequence identity values are obtained as described below by using the sequence comparison computer program ALIGN-2, wherein the complete source code for the ALIGN-2 program is provided below. The ALIGN-2 sequence comparison computer program was authored by Genentech, Inc. and the source code shown below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided below. The ALIGN-2 program should be compiled for use on a UNIX operating system, preferably digital UNIX V4.0D. All sequence comparison parameters are set by the ALIGN-2 program and do not vary.

For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, FIGS. 3C-D demonstrate how to calculate the % nucleic acid sequence identity of the nucleic acid sequence designated "Comparison DNA" to the nucleic acid sequence designated "PRO-DNA".

Unless specifically stated otherwise, all % nucleic acid sequence identity values used herein are obtained as described above using the ALIGN-2 sequence comparison computer program. However, % nucleic acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, EG-VEGF variant polynucleotides are nucleic acid molecules that encode an active EG-VEGF polypeptide and which are capable of hybridizing, preferably under stringent hybridization and wash conditions, to nucleotide sequences encoding the full-length EG-VEGF polypeptide shown in FIG. 2 (SEQ ID NO:2). EG-VEGF variant polypeptides may be those that are encoded by a EG-VEGF variant polynucleotide.

The term "positives", in the context of the amino acid sequence identity comparisons performed as described above, includes amino acid residues in the sequences compared that are not only identical, but also those that have similar properties. Amino acid residues that score a positive value to an amino acid residue of interest are those that are either identical to the amino acid residue of interest or are a preferred substitution (as defined in Table 1 below) of the amino acid residue of interest.

For purposes herein, the % value of positives of a given amino acid sequence A to, with, or against a given amino acid sequence B (which can alternatively be phrased as a given amino acid sequence A that has or comprises a certain % positives to, with, or against a given amino acid sequence B) is calculated as follows:

100 times the fraction X/Y where X is the number of amino acid residues scoring a positive value as defined above by the sequence alignment program ALIGN-2 in that program's alignment of A and B, and where Y is the total number of amino acid residues in B. It will be appreciated that where the length of amino acid sequence A is not equal to the length of amino acid sequence B, the % positives of A to B will not equal the % positives of B to A.

"Isolated," when used to describe the various polypeptides disclosed herein, means polypeptide that has been identified and separated and/or recovered from a component of its natural environment. Preferably, the isolated polypeptide is free of association with all components with which it is naturally associated. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the EG-VEGF natural environment will not be present. Ordinarily, however, isolated polypeptide will be prepared by at least one purification step.

An "isolated" nucleic acid molecule encoding a EG-VEGF polypeptide is a nucleic acid molecule that is identified and separated from at least one contaminant nucleic acid molecule with which it is ordinarily associated in the natural source of the EG-VEGF-encoding nucleic acid. Preferably, the isolated nucleic is free of association with all components with which it is naturally associated. An isolated EG-VEGF-encoding nucleic acid molecule is other than in the form or setting in which it is found in nature. Isolated nucleic acid molecules therefore are distinguished from the EG-VEGF-encoding nucleic acid molecule as it exists in natural cells. However, an isolated nucleic acid molecule encoding a EG-VEGF polypeptide includes EG-VEGF-encoding nucleic acid molecules contained in cells that ordinarily express EG-VEGF where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adapters or linkers are used in accordance with conventional practice.

The term "antibody" is used in the broadest sense and specifically covers, for example, single anti-EG-VEGF monoclonal antibodies (including agonist, antagonist, and neutralizing antibodies), anti-EG-VEGF antibody compositions with polyepitopic specificity, single chain anti-EG-VEGF antibodies, and fragments of anti-EG-VEGF antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature, which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a EG-VEGF polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of EG-VEGF which retain a biological and/or an immunological activity of native or naturally-occurring EG-VEGF, wherein "biological" activity refers to a biological function (either inhibitory or stimulatory) caused by a native or naturally-occurring EG-VEGF other than the ability to induce the production of an antibody against an antigenic epitope possessed by a native or naturally-occurring EG-VEGF and an "immunological" activity refers to the ability to induce the production of an antibody against an antigenic epitope possessed by a native or naturally-occurring EG-VEGF. Biological activities specifically include regulation of cellular proliferation and chemotaxis. A preferred biological activity is the ability to regulate the production, growth, differentiation, survival, and/or migration of endothelial cells. Even more preferably, the biological activity is the ability to induce proliferation, migration and/or fenestrations in capillary endothelial cells, preferably steroidogenic cells, within endocrine glands. Another preferred biological activity is the ability to promote angiogenesis and/or regulate vascular permeability in endocrine glands, especially in steroidogenic tissues within endocrine glands. Yet another preferred biological activity is the ability to induce phosphorylation of a signaling molecule involved in cell proliferation and/or survival, such as MAP kinase, e.g. ERK1 or ERK2, Akt and eNOS. Yet a further preferred biological activity is the ability to promote endothelial cell survival.

The term "angiogenesis" is used in the broadest sense and specifically includes the creation of new blood vessels from existing vessels, just as the de novo assembly of endothelial progenitor cells into vessels through migration, proliferation, cell-cell aggregation, assembly and morphogenesis (also referred to as "vasculogenesis").

The term "antagonist" is used in the broadest sense, and includes any molecule that partially or fully blocks, inhibits, or neutralizes a biological activity of a native EG-VEGF polypeptide disclosed herein. In a similar manner, the term "agonist" is used in the broadest sense and includes any molecule that mimics a biological activity of a native EG-VEGF polypeptide disclosed herein. Suitable agonist or antagonist molecules specifically include agonist or antagonist antibodies or antibody fragments, fragments or amino acid sequence variants of native EG-VEGF polypeptides, peptides, small organic molecules, etc. Methods for identifying agonists or antagonists of a EG-VEGF polypeptide may comprise contacting a EG-VEGF polypeptide with a candidate agonist or antagonist molecule and measuring a detectable change in one or more biological activities normally associated with the EG-VEGF polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. For example, in tumor (e.g., cancer) treatment, a therapeutic agent may directly decrease the pathology of tumor cells, or render the tumor cells more susceptible to treatment by other therapeutic agents, e.g., radiation and/or chemotherapy.

"Steroidogenesis" is the hormonally induced, CAMP-mediated acute regulation of steroid hormone biosynthesis in "steroidogenic cells" characterized by the mobilization of cholesterol from cellular stores to the mitochondria outer membrane, and its translocation to the inner membrane where the conversion of cholesterol to pregnenolone occurs.

"Steroidogenic tissue" refers to tissue which produces steroidal hormones by the process of steroidogenesis. Examples include tissues of the adrenal gland, the reproductive organs, gut and respiratory tract tissue.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, other higher primates, domestic and farm animals, and zoo, sports, or pet animals, such as dogs, cats, cattle, horses, sheep, pigs, goats, rabbits, etc. Preferably, the mammal is human.

"Tumor", as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancers of particular interest herein include cancers of the reproductive organs, e.g. ovarian cancer, testicular cancer, uterine cancer, cervical cancer; prostate cancer; cancers of the adrenal gland, including cancers of the adrenal cortex (e.g. adrenocortical carcinoma) and the adrenal medulla; thyroid cancer; parathyroid cancer; pancreatic cancer; and endometrial carcinoma.

The "pathology" of a disease includes all phenomena that compromise the well-being of the patient. For cancer, this includes, without limitation, abnormal or uncontrollable cell growth, metastasis, interference with the normal functioning of neighboring cells, release of cytokines or other secretory products at abnormal levels, suppression or aggravation of inflammatory or immunological response, etc.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the VH and VL domains of antibody, wherein these domains are present in a single polypeptide chain. Preferably, the Fv polypeptide further comprises a polypeptide linker between the VH and VL domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a EG-VEGF polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

The terms "vascular endothelial growth factor", "VEGF", "VEGF polypeptide" and "VEGF protein" when used herein encompass native sequence VEGF and VEGF variants (which are further defined herein). The VEGF polypeptide may be isolated from a variety of sources, such as from human tissue types or from another source, or prepared by recombinant and/or synthetic methods.

A "native sequence VEGF" comprises a polypeptide having the same amino acid sequence as a VEGF derived from nature. Such native sequence VEGF can be isolated from nature or can be produced by recombinant and/or synthetic means. The term "native sequence VEGF" specifically encompasses naturally-occurring truncated or secreted forms (e.g., an extracellular domain sequence), naturally-occurring variant forms (e.g., alternatively spliced forms) and naturally-occurring allelic variants of the VEGF. In one embodiment of the invention, the native sequence VEGF is one of the five known isoforms, consisting of 121, 145, 165, 189, and 206 amino acid residues, respectively, as described, for example in U.S. Pat. Nos. 5,332,671 and 5,240,848; in PCT Publication No. WO 98/10071; Leung et al., Science 246:1306-1309 (1989); and Keck et al., Science 246:1309-1312 (1989).

"VEGF variant polypeptide" means an active VEGF polypeptide as defined below having at least about 80%, preferably at least about 85%, more preferably at least about 90%, event more preferably at least about 95%, most preferably at least about 98% amino acid sequence identity with the amino acid sequence of a native sequence VEGF. Such VEGF variant polypeptides include, for instance, VEGF polypeptides wherein one or more amino acid residues are added, or deleted, at the N- and/or C-terminus, as well as within one or more internal domains, of the native sequence.

The sequence identity (either amino acid or nucleic acid) for VEGF is determined using the same approach specifically described with regard to EG-VEGF. Similarly, the definitions provided for agonist and antagonists of EG-VEGF, including but not limited to antibodies, will apply to VEGF agonists and antagonists.

An antibody binds "essentially the same epitope" as a reference antibody, when the two antibodies recognize identical or sterically overlapping epitopes. The most widely used and rapid methods for deteing whether two epitopes bind to identical or sterically overlapping epitope are competition binding assays (e.g. competition ELISA assays), which can be configured in a number of different formats, using either labeled antigen or labeled antibody. Usually, the antigen is immobilized on a 96-well plate, and the ability of the unlabeled antibodies to block the binding of labeled antibodies is measured using radioactive or enzyme labels.

II. Compositions and Methods of the Invention

A. Full-Length EG-VEGF Polypeptide

The present invention provides newly identified and isolated nucleotide sequences encoding polypeptides referred to in the present application as EG-VEGF (or also UNQ600). In particular, cDNA encoding a EG-VEGF polypeptide has been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by DNA60621-1516 as well as all further native homologues and variants included in the foregoing definition of EG-VEGF, will be referred to as "EG-VEGF", regardless of their origin or mode of preparation.

As disclosed in the Examples below, a cDNA clone designated herein as DNA60621-1516 has been deposited with the ATCC. The actual nucleotide sequence of the clone can readily be determined by the skilled artisan by sequencing of the deposited clone using routine methods in the art. The predicted amino acid sequence can be determined from the nucleotide sequence using routine skill. For the EG-VEGF polypeptide and encoding nucleic acid described herein, Applicants have identified what is believed to be the reading frame best identifiable with the sequence information available at the time.

Using the ALIGN-2 sequence alignment computer program referenced above, it has been found that the full-length native sequence EG-VEGF (shown in FIG. 2 and SEQ ID NO:2) has certain amino acid sequence identity with EG-VEGF_DENPO, a protein from black mamba venom. However, no significant sequence identities to any known mammalian proteins were revealed.

B. EG-VEGF Variants

In addition to the full-length native sequence EG-VEGF polypeptides described herein, it is contemplated that EG-VEGF variants can be prepared. EG-VEGF variants can be prepared by introducing appropriate nucleotide changes into the EG-VEGF DNA, and/or by synthesis of the desired EG-VEGF polypeptide. Those skilled in the art will appreciate that amino acid changes may alter post-translational processes of the EG-VEGF, such as changing the number or position of glycosylation sites or altering the membrane anchoring characteristics.

Variations in the native full-length sequence EG-VEGF or in various domains of the EG-VEGF described herein, can be made, for example, using any of the techniques and guidelines for conservative and non-conservative mutations set forth, for instance, in U.S. Pat. No. 5,364,934. Variations may be a substitution, deletion or insertion of one or more codons encoding the EG-VEGF that results in a change in the amino acid sequence of the EG-VEGF as compared with the native sequence EG-VEGF. Optionally the variation is by substitution of at least one amino acid with any other amino acid in one or more of the domains of the EG-VEGF. Guidance in determining which amino acid residue may be inserted, substituted or deleted without adversely affecting the desired activity may be found by comparing the sequence of the EG-VEGF with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

EG-VEGF polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the EG-VEGF polypeptide.

EG-VEGF fragments may be prepared by any of a number of conventional techniques. Desired peptide fragments may be chemically synthesized. An alternative approach involves generating EG-VEGF fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, EG-VEGF polypeptide fragments share at least one biological and/or immunological activity with the native EG-VEGF polypeptide shown in FIG. 2 (SEQ ID NO:2).

In particular embodiments, conservative substitutions of interest are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the EG-VEGF polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the EG-VEGF variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244: 1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

C. Modifications of EG-VEGF

Covalent modifications of EG-VEGF are included within the scope of this invention. One type of covalent modification includes reacting targeted amino acid residues of a EG-VEGF polypeptide with an organic derivatizing agent that is capable of reacting with selected side chains or the N- or C-terminal residues of the EG-VEGF. Derivatization with bifunctional agents is useful, for instance, for crosslinking EG-VEGF to a water-insoluble support matrix or surface for use in the method for purifying anti-EG-VEGF antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the EG-VEGF polypeptide included within the scope of this invention comprises altering the native glycosylation pattern of the polypeptide. "Altering the native glycosylation pattern" is intended for purposes herein to mean deleting one or more carbohydrate moieties found in native sequence EG-VEGF (either by removing the underlying glycosylation site or by deleting the glycosylation by chemical and/or enzymatic means), and/or adding one or more glycosylation sites that are not present in the native sequence EG-VEGF. In addition, the phrase includes qualitative changes in the glycosylation of the native proteins, involving a change in the nature and proportions of the various carbohydrate moieties present.

Addition of glycosylation sites to the EG-VEGF polypeptide may be accomplished by altering the amino acid sequence. The alteration may be made, for example, by the addition of, or substitution by, one or more serine or threonine residues to the native sequence EG-VEGF (for O-linked glycosylation sites). The EG-VEGF amino acid sequence may optionally be altered through changes at the DNA level, particularly by mutating the DNA encoding the EG-VEGF polypeptide at preselected bases such that codons are generated that will translate into the desired amino acids.

Another means of increasing the number of carbohydrate moieties on the EG-VEGF polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the EG-VEGF polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of EG-VEGF comprises linking the EG-VEGF polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

The EG-VEGF of the present invention may also be modified in a way to form a chimeric molecule comprising EG-VEGF fused to another, heterologous polypeptide or amino acid sequence.

In one embodiment, such a chimeric molecule comprises a fusion of the EG-VEGF with a tag polypeptide which provides an epitope to which an anti-tag antibody can selectively bind. The epitope tag is generally placed at the amino- or carboxyl-terminus of the EG-VEGF. The presence of such epitope-tagged forms of the EG-VEGF can be detected using an antibody against the tag polypeptide. Also, provision of the epitope tag enables the EG-VEGF to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the EG-VEGF with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a EG-VEGF polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of EG-VEGF

The description below relates primarily to production of EG-VEGF by culturing cells transformed or transfected with a vector containing EG-VEGF nucleic acid. It is, of course, contemplated that alternative methods, which are well known in the art, may be employed to prepare EG-VEGF. For instance, the EG-VEGF sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the EG-VEGF may be chemically synthesized separately and combined using chemical or enzymatic methods to produce the full-length EG-VEGF.

1. Isolation of DNA Encoding EG-VEGF

DNA encoding EG-VEGF may be obtained from a cDNA library prepared from tissue believed to possess the EG-VEGF mRNA and to express it at a detectable level. Accordingly, human EG-VEGF DNA can be conveniently obtained from a cDNA library prepared from human tissue, such as described in the Examples. The EG-VEGF-encoding gene may also be obtained from a genomic library or by known synthetic procedures (e.g., automated nucleic acid synthesis).

Libraries can be screened with probes (such as antibodies to the EG-VEGF or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding EG-VEGF is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for EG-VEGF production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for EG-VEGF-encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; Louvencourt et al., *J. Bacteriol.*, 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus*; *yarrowia* (EP 402,226); *Pichia pastoris* (EP 183,070; Sreekrishna et al., *J. Basic Microbiol.*, 28:265-278 [1988]); *Candida*; *Trichoderma reesia* (EP 244,234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora*, *Penicillium*, *Tolypocladium* (WO 91/00357 published 10 Jan. 1991), and *Aspergillus* hosts such as *A. nidulans* (Ballance et al., *Biochem. Biophys. Res. Commun.*, 112: 284-289 [1983]; Tilburn et al., *Gene*, 26:205-221 [1983]; Yelton et al., *Proc. Natl. Acad. Sci. USA*, 81: 1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of *Hansenula*, *Candida*, *Kloeckera*, *Pichia*, *Saccharomyces*, *Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated EG-VEGF are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/−DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding EG-VEGF may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The EG-VEGF may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the EG-VEGF-encoding DNA that is inserted into the vector. The signal sequence may be a prokaryotic signal sequence selected, for example, from the group of the alkaline phosphatase, penicillinase, 1pp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the EG-VEGF-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the EG-VEGF-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding EG-VEGF.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

EG-VEGF transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the EG-VEGF by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the EG-VEGF coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding EG-VEGF.

Still other methods, vectors, and host cells suitable for adaptation to the synthesis of EG-VEGF in recombinant vertebrate cell culture are described in Gething et al., *Nature*, 293:620-625 (1981); Mantei et al., *Nature,* 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence EG-VEGF polypeptide or against a synthetic peptide based on the DNA sequences provided herein or against exogenous sequence fused to EG-VEGF DNA and encoding a specific antibody epitope.

5. Purification of Polypeptide

Forms of EG-VEGF may be recovered from culture medium or from host cell lysates. If membrane-bound, it can be released from the membrane using a suitable detergent solution (e.g. Triton-X 100) or by enzymatic cleavage. Cells employed in expression of EG-VEGF can be disrupted by various physical or chemical means, such as freeze-thaw cycling, sonication, mechanical disruption, or cell lysing agents.

It may be desired to purify EG-VEGF from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the EG-VEGF. Various methods of protein purification may be employed and such methods are known in the art and described for example in Deutscher, *Methods in Enzymology,* 182 (1990); Scopes, *Protein Purification: Principles and Practice*, Springer-Verlag, New York (1982). The purification step(s) selected will depend, for example, on the nature of the production process used and the particular EG-VEGF produced.

E. Uses for EG-VEGF

Nucleotide sequences (or their complement) encoding EG-VEGF have various applications in the art of molecular biology, including uses as hybridization probes, in chromosome and gene mapping and in the generation of anti-sense RNA and DNA. EG-VEGF nucleic acid will also be useful for the preparation of EG-VEGF polypeptides by the recombinant techniques described herein.

The full-length native sequence EG-VEGF gene (SEQ ID NO:1), or portions thereof, may be used as hybridization probes for a cDNA library to isolate the full-length EG-VEGF cDNA or to isolate still other cDNAs (for instance, those encoding naturally-occurring variants of EG-VEGF or EG-VEGF from other species) which have a desired sequence identity to the EG-VEGF sequence disclosed in FIG. 1 (SEQ ID NO:1). Optionally, the length of the probes will be about 20 to about 50 bases. The hybridization probes may be derived from at least partially novel regions of the nucleotide sequence of SEQ ID NO:1 wherein those regions may be determined without undue experimentation or from genomic sequences including promoters, enhancer elements and introns of native sequence EG-VEGF. By way of example, a screening method will comprise isolating the coding region of the EG-VEGF gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the EG-VEGF gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the EG-VEGF nucleic acids include antisense or sense oligonucleotides comprising a singe-stranded nucleic acid sequence (either RNA or DNA) capable of binding to target EG-VEGF mRNA (sense) or EG-VEGF DNA (antisense) sequences. Antisense or sense oligonucleotides, according to the present invention, comprise a fragment of the coding region of EG-VEGF DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of EG-VEGF proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The probes may also be employed in PCR techniques to generate a pool of sequences for identification of closely related EG-VEGF coding sequences.

Nucleotide sequences encoding a EG-VEGF can also be used to construct hybridization probes for mapping the gene which encodes that EG-VEGF and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

This invention also provides for methods of using the EG-VEGF in assays to identify other proteins or molecules that can bind to the EG-VEGF protein. By such methods, inhibitors of the receptor/ligand binding interaction can be identified. Proteins involved in such binding interactions can also be used to screen for peptide or small molecule inhibitors or agonists of the binding interaction. Also, the receptor EG-VEGF can be used to isolate correlative ligand(s). Screening assays can be designed to find lead compounds that mimic the biological activity of a native EG-VEGF or a receptor for EG-VEGF. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode EG-VEGF or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding EG-VEGF can be used to clone genomic DNA encoding EG-VEGF in accordance with established techniques and the genomic sequences used to generate transgenic animals that contain cells which express DNA encoding EG-VEGF. Methods for generating transgenic animals, particularly animals such as mice or rats, have become conventional in the art and are described, for example, in U.S. Pat. Nos. 4,736,866 and 4,870,009. Typically, particular cells would be targeted for EG-VEGF transgene incorporation with tissue-specific enhancers. Transgenic animals that include a copy of a transgene encoding EG-VEGF introduced into the germ line of the animal at an embryonic stage can be used to examine the effect of increased expression of DNA encoding EG-VEGF. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of EG-VEGF can be used to construct a EG-VEGF "knock out" animal which has a defective or altered gene encoding EG-VEGF as a result of homologous recombination between the endogenous gene encoding EG-VEGF and altered genomic DNA encoding EG-VEGF introduced into an embryonic stem cell of the animal. For example, cDNA encoding EG-VEGF can be used to clone genomic DNA encoding EG-VEGF in accordance with established techniques. A portion of the genomic DNA encoding EG-VEGF can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the EG-VEGF polypeptide.

Nucleic acid encoding the EG-VEGF polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The EG-VEGF polypeptides described herein may also be employed as molecular weight markers for protein electrophoresis purposes.

The nucleic acid molecules encoding the EG-VEGF polypeptides or fragments thereof described herein are useful for chromosome identification. In this regard, there exists an ongoing need to identify new chromosome markers, since relatively few chromosome marking reagents, based upon actual sequence data are presently available. Each EG-VEGF nucleic acid molecule of the present invention can be used as a chromosome marker.

The EG-VEGF polypeptides and nucleic acid molecules of the present invention may also be used for tissue typing, wherein the EG-VEGF polypeptides of the present invention may be differentially expressed in one tissue as compared to another. EG-VEGF nucleic acid molecules will find use for generating probes for PCR, Northern analysis, Southern analysis and Western analysis.

The EG-VEGF polypeptides and modulators thereof described herein may also be employed as therapeutic agents. The EG-VEGF polypeptides and EG-VEGF modulators of the present invention can be formulated according to known methods to prepare pharmaceutically useful compositions, whereby the EG-VEGF product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a EG-VEGF polypeptide or agonist or antagonist thereof is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a mariner different from that to another organ or tissue.

Where sustained-release administration of a EG-VEGF polypeptide or modulator is desired in a formulation with release characteristics suitable for the treatment of any disease or disorder requiring administration of the EG-VEGF polypeptide, microencapsulation of the EG-VEGF polypeptide is contemplated. Microencapsulation of recombinant proteins for sustained release has been successfully performed with human growth hormone (rhGH), interferon-(rhIFN-), interleukin-2, and MN rgp120. Johnson et al., *Nat. Med.*, 2:795-799 (1996); Yasuda, *Biomed. Ther.*, 27:1221-1223 (1993); Hora et al., *Bio/Technology*, 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasm and R. Langer (Eds.), *Biodegradable Polymers as Drug Delivery Systems* (Marcel Dekker: New York, 1990), pp. 1-41.

The therapeutic agents provided herein can be used in a number of treatments. The treatments include treating an individual with a condition associated with hormone producing tissue or endocrine glands. In one aspect, EG-VEGF or a EG-VEGF agonist is administered to an individual in need thereof in an amount effective to treat the condition. EG-VEGF can be administered in a polypeptide or nucleic acid form. Preferably, the condition is one which requires an increase in the number of cells producing a particular hormone or the survival of such cells. Examples of such conditions include diabetes. Other conditions include those wherein it is desired to increase the number of cells in the reproductive organs such as those of the ovary, testis, uterus, prostate and placenta.

Preferably, a EG-VEGF antagonist is administered to an individual with a condition associated with hormone producing tissue or endocrine glands. Wherein an EG-VEGF antagonist is administered, preferably the condition is one which requires a decrease in the number of cells producing a particular hormone or a decrease in cell proliferation. For example, a method of regulating fertility in an individual is provided herein which comprises administering a EG-VEGF antagonist to the individual in an amount effective to regulate fertility. In one embodiment, fertility is regulated by inhibiting follicle maturation and/or ovulation. Alternatively, wherein the individual has or is at risk of having polycystic ovary syndrome a EG-VEGF antagonist is administered to the individual to maintain fertility by preventing the infertility which generally results from not treating the syndrome. An individual is at risk of a condition if there if the condition is hereditary and frequent in the family or has early symptoms of the condition. EG-VEGF antagonists can also be administered to treat cysts and other conditions associated with overproliferation, inflammation and excessive angiogenesis in hormone producing tissues.

Steroid hormone-dependent disorders that may be addressed using compositions and methods of the present invention further include lipoid congenital adrenal hyperplasia, infertility, sexual maturation, androgen-dependent tumors, precocious puberty, McCune-Albright syndrome, adrenal-hypoplasia congenita, or hypogonadotropic hypogonadism.

A specific condition which can be treated by the agents and compositions provided herein is cancer, in particular steroid-, e.g. androgen-dependent cancer. A preferred method of treating cancer as provided herein comprises administering a EG-VEGF antagonist to an individual with or at risk of having cancer in an amount effective to treat cancer. In one embodiment, the cancer is of a tissue selected from the group consisting of ovary, testis, prostate and uterus.

It is understood that the methods of enhancing cell survival, cell proliferation, inhibition of cell proliferation, chemotaxis, and methods of inhibiting chemotaxis can be performed in vivo or in vitro. In some cases, it may be desirable to add EG-VEGF to a cell sample in vitro so as to stimulate proliferation or survival of a specific cell type. The EG-VEGF treated sample can then be used in screening assays or be transplanted into an individual in need of treatment or into an animal model.

This invention also encompasses methods of screening compounds to identify those that mimic or enhance the EG-VEGF polypeptide (agonists) or prevent the effect of the EG-VEGF polypeptide (antagonists). EG-VEGF agonists and antagonists are also referred to as EG-VEGF modulators herein. Screening assays for antagonist drug candidates are designed to identify compounds that bind or complex with the EG-VEGF polypeptides encoded by the genes identified herein, or otherwise interfere with the interaction of the encoded polypeptides with other cellular proteins. The screening assays provided herein include assays amenable to high-throughput screening of chemical libraries, making them particularly suitable for identifying small molecule drug candidates. Generally, binding assays and activity assays are provided.

The assays can be performed in a variety of formats, including protein-protein binding assays, biochemical screening assays, immunoassays, and cell-based assays, which are well characterized in the art.

All assays for antagonists are common in that they call for contacting the drug candidate with an EG-VEGF polypeptide encoded by a nucleic acid identified herein under conditions and for a time sufficient to allow these two components to interact.

In binding assays, the interaction is binding and the complex formed can be isolated or detected in the reaction mixture. In a particular embodiment, either the EG-VEGF polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the EG-VEGF polypeptide and drying. Alternatively, an immobilized antibody, e.g., a monoclonal antibody, specific for the EG-VEGF polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular EG-VEGF polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA*, 88:9578-

9582 (1991)) as disclosed by Chevray and Nathans, *Proc. Natl. Acad. Sci. USA*, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding an EG-VEGF polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for agonists and antagonists, the EG-VEGF polypeptide may be added to a cell along with the compound to be screened. A particular activity known to be modulated by EG-VEGF is observed and the ability of the compound to enhance or inhibit this activity, in the presence of the EG-VEGF polypeptide, indicates that the compound is an agonist or antagonist to the EG-VEGF polypeptide, respectively. Alternatively, agonists and antagonists may be detected by combining the EG-VEGF polypeptide and candidate compounds with membrane-bound EG-VEGF polypeptide receptors or recombinant receptors under appropriate conditions for a competitive inhibition assay. The EG-VEGF polypeptide can be labeled, such as by radioactivity, such that the number of EG-VEGF polypeptide molecules bound to the receptor can be used to determine the effectiveness of the potential agonist or antagonist.

The gene encoding the receptor for EG-VEGF can be identified by numerous methods known to those of skill in the art, for example, ligand panning and FACS sorting. Coligan et al., *Current Protocols in Immun.*, 1(2): Chapter 5 (1991). Preferably, expression cloning is employed wherein polyadenylated RNA is prepared from a cell responsive to the EG-VEGF polypeptide and a cDNA library created from this RNA is divided into pools and used to transfect COS cells or other cells that are not responsive to the EG-VEGF polypeptide. Transfected cells that are grown on glass slides are exposed to labeled EG-VEGF polypeptide. The EG-VEGF polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled EG-VEGF polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled EG-VEGF polypeptide in the presence of the candidate compound. The ability of the compound to enhance or block this interaction could then be measured.

More specific examples of potential antagonists include an oligonucleotide that binds to the fusions of immunoglobulin with EG-VEGF polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the EG-VEGF polypeptide that recognizes the receptor but imparts no effect, thereby competitively inhibiting the action of the EG-VEGF polypeptide.

Another potential EG-VEGF polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature EG-VEGF polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al., *Science*, 241: 456 (1988); Dervan et al., *Science*, 251:1360 (1991)), thereby preventing transcription and the production of the EG-VEGF polypeptide. The antisense RNA oligonucleotide hybridizes to the mRNA in vivo and blocks translation of the mRNA molecule into the EG-VEGF polypeptide (antisense—Mario, *Neurochem.*, 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the EG-VEGF polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the EG-VEGF polypeptide, thereby blocking the normal biological activity of the EG-VEGF polypeptide. Examples of small molecules include, but are not limited to, small peptides or peptide-like molecules, preferably soluble peptides, and synthetic non-peptidyl organic or inorganic compounds.

In an alternative embodiment, overexpression of an agonist can serve as an antagonist wherein activity is regulated by positive feedback.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known to those skilled in the art.

It is appreciated that all the assays provided herein can be used to screen a wide variety of candidate bioactive agents. The term "candidate bioactive agent", "candidate agent" or "drug candidate" or grammatical equivalents as used herein describes any molecule, e.g., protein, oligopeptide, small organic molecule, polysaccharide, polynucleotide, purine analog, etc., to be tested for bioactive agents that are capable of directly or indirectly altering either the cellular activity phenotype or the expression of a EG-VEGF sequence, including both nucleic acid sequences and protein sequences.

Candidate agents can encompass numerous chemical classes, though typically they are organic molecules, preferably small organic compounds having a molecular weight of more than 100 and less than about 2,500 daltons. Small molecules are further defined herein as having a molecular weight of between 50 kD and 2000 kD. In another embodiment, small molecules have a molecular weight of less than 1500, or less than 1200, or less than 1000, or less than 750, or less than 500 kD. In one embodiment, a small molecule as used herein has a molecular weight of about 100 to 200 kD. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eucaryotic proteins may be made for screening in the methods of the invention. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occurring nucleic acids, random nucleic acids, or "biased" random nucleic acids. For example, digests of procaryotic or eucaryotic genomes may be used as is outlined above for proteins.

In a preferred embodiment, the candidate bioactive agents are organic chemical moieties, a wide variety of which are available in the literature.

In a preferred embodiment, as outlined above, screens may be done on individual genes and gene products (proteins). In a preferred embodiment, the gene or protein has been identified as described below in the Examples as a differentially expressed gene associated with particular tissues and thus conditions related to those tissues. Thus, in one embodiment, screens are designed to first find candidate agents that can bind to EG-VEGF, and then these agents may be used in assays that evaluate the ability of the candidate agent to modulate EG-VEGF activity. Thus, as will be appreciated by those in the art, there are a number of different assays which may be run.

In one embodiment, EG-VEGF, preferably immobilized on a solid support, is contacted with a plurality of candidate bioactive agents and candidates that bind to EG-VEGF are selected for further study. Binding of candidate bioactive agents may be measured directly if the candidate bioactive agent is labelled. A candidate bioactive agent may preferably be labelled radioactively. Alternatively it may be labelled fluorescently. If the candidate bioactive agent is not labelled, binding may be determined indirectly based on a measured response to the binding. Alternatively, interaction with a candidate bioactive compound can be assessed based on the ability of the candidate bioactive compound to inhibit the binding of a known, labelled ligand.

Screening for agents that modulate the activity of EG-VEGF may also be done. In a preferred embodiment, methods for screening for a bioactive agent capable of modulating the activity of EG-VEGF comprise the steps of adding a candidate bioactive agent to a sample of EG-VEGF and determining an alteration in the biological activity of EG-VEGF. "Modulating the activity of EG-VEGF" includes an increase in activity, a decrease in activity, or a change in the type or kind of activity present. Thus, in this embodiment, the candidate agent should both bind to EG-VEGF (although this may not be necessary), and alter its biological or biochemical activity as defined herein. The methods include both in vitro screening methods, as are generally outlined above, and in vivo screening of cells for alterations in the presence, distribution, activity or amount of EG-VEGF.

Thus, in this embodiment, the methods comprise combining a sample and a candidate bioactive agent, and evaluating the effect on EG-VEGF activity. By "EG-VEGF protein activity" or grammatical equivalents herein is meant at least one of the EG-VEGF protein's biological activities, including, but not limited to cell survival, cellular proliferation, chemotaxis/migration activity, angiogenesis, cell differentiation and cell fenestration. These activities are preferably specific in hormone producing tissues and cells, and more preferably, steroidogenic cells. Preferred cell types for specific activity include those of the reproductive system including cells of the ovaries, testis, prostate, uterus and placenta. Particular preferred cell types include the stroma and theca interna of the ovary and Leydig cells of the testis. Cells of the pancreas and the adrenal cortex are also preferred. An inhibitor of EG-VEGF activity is the inhibition of any one or more EG-VEGF protein activities.

In a preferred embodiment, the activity of the EG-VEGF protein is increased; in another preferred embodiment, the activity of the EG-VEGF protein is decreased. Thus, bioactive agents that are antagonists are preferred in some embodiments, and bioactive agents that are agonists may be preferred in other embodiments.

In one aspect of the invention, cells containing EG-VEGF sequences are used in drug screening assays by evaluating the effect of drug candidates on EG-VEGF. Cell type include normal cells, and more preferably cells with abnormal proliferative rates including tumor cells, most preferably human tumor cells.

Methods of assessing EG-VEGF activity are known in the art and include growth and viability assays using cultured or primary cells. In such assays, cell populations are monitored for growth and or viability, often over time and comparing samples incubated with various concentrations of the bioactive agent or without the bioactive agent. Cell number can be quantified using agents that such as 3-(4,5-dimethylthiazol-2-yl)-2,5-diphenyltetrazolium bromide (MTT), 3-(4,5-dimethylthiazol-2-yl)-5-(3-carboxymethoxyphenyl)-2-(4-sulfophenyl)-2H-tetrazolium (MTS) [U.S. Pat. No. 5,185,450] and Alamar Blue which are converted to colored or fluorescent compounds in the presence of metabolically active cells. Alternatively, dyes that bind to cellular protein such as sulforhodamine B (SRB) or crystal violet can be used to quantify cell number. Alternatively, cells can be directly counted using a particle counter, such as a Coulter Counter™ manufactured by Beckman Coulter, or counted using a microscope to observe cells on a hemocytometer. Preferably, cells counted using the hemocytometer are observed in a solution of trypan blue to distinguish viable from dead cells. Other methods of quantifying cell number are known to those skilled in the art. These assays can be performed on any of the cells, including those in a state of necrosis.

A protein has chemotactic activity for a particular cell population if it can stimulate, directly or indirectly, the directed orientation or movement of the cell population. Preferably, the protein has the ability to directly stimulate directed movement of the cells. As described below, EG-VEGF has chemotactic activity. Changes in the chemotactic activity of EG-VEGF can readily be determined by employing known assays for cell chemotaxis (e.g., migration assays as described below in the examples).

In a preferred embodiment, the methods comprise adding a candidate bioactive agent, as defined above, to a cell comprising EG-VEGF. Preferred cell types include almost any cell. The cells contain a nucleic acid, preferably recombinant, that encodes a EG-VEGF protein. In a preferred embodiment, a library of candidate agents are tested on a plurality of cells.

In one aspect, the assays are evaluated in the presence or absence or previous or subsequent exposure to physiological signals, for example hormones, antibodies, peptides, antigens, cytokines, growth factors, action potentials, pharmacological agents including chemotherapeutics, radiation, carcinogenics, or other cells (i.e. cell-cell contacts). In another example, the determinations are determined at different stages of the cell cycle process.

The EG-VEGF sequences provided herein can also be used in methods of diagnosis. Overexpression of EG-VEGF may indicate a cyst or cancer in a reproductive organ. Moreover, a sample from a patient may be analyzed for mutated or disfunctional EG-VEGF. Generally, such methods include comparing a sample from a patient and comparing EG-VEGF expression to that of a control.

F. Anti-EG-VEGF Antibodies

The present invention further provides anti-EG-VEGF antibodies. Exemplary antibodies include polyclonal, monoclonal, humanized, bispecific, and heteroconjugate antibodies.

1. Polyclonal Antibodies

The anti-EG-VEGF antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the EG-VEGF polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-EG-VEGF antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the EG-VEGF polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice,* Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications,* Marcel Dekker, Inc., New York, (1987) pp. 51-63].

The culture medium in which the hybridoma cells are cultured can then be assayed for the presence of monoclonal antibodies directed against EG-VEGF. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-EG-VEGF antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

4. Bispecific Antibodies

Bispecific antibodies are monoclonal, preferably human or humanized, antibodies that have binding specificities for at least two different antigens. In the present case, one of the binding specificities is for the EG-VEGF, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab☐)$_2$ bispecific antibodies). Techniques for generating bispecific antibodies from antibody fragments have been described in the literature. For example, bispecific antibodies can be prepared using chemical linkage. Brennan et at, Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from E. coli and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies may bind to two different epitopes on a given EG-VEGF polypeptide herein. Alternatively, an anti-EG-VEGF polypeptide arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular EG-VEGF polypeptide. Bispecific antibodies may also be used to localize cytotoxic agents to cells which express a particular EG-VEGF polypeptide. These antibodies possess a EG-VEGF-binding arm and an arm which binds a cytotoxic agent or a radionuclide chelator, such as EOTUBE, DPTA, DOTA, or TETA. Another bispecific antibody of interest binds the EG-VEGF polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med., 176:

1191-1195 (1992) and Shopes, *J. Immunol.*, 148: 2918-2922 (1992). Homodimeric antibodies with enhanced anti-tumor activity may also be prepared using heterobifunctional crosslinkers as described in Wolff et al. *Cancer Research*, 53: 2560-2565 (1993). Alternatively, an antibody can be engineered that has dual Fc regions and may thereby have enhanced complement lysis and ADCC capabilities. See Stevenson et al., *Anti-Cancer Drug Design*, 3: 219-230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA*, 82: 3688 (1985); Hwang et al., *Proc. Natl. Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.*, 257: 286-288 (1982) via a disulfide-interchange reaction. A chemotherapeutic agent (such as Doxorubicin) is optionally contained within the liposome. See Gabizon et al., *J. National Cancer Inst.*, 81(19): 1484 (1989).

9. Pharmaceutical Compositions of Antibodies

Antibodies specifically binding a EG-VEGF polypeptide identified herein, as well as other molecules identified by the screening assays disclosed hereinbefore, can be administered for the treatment of various disorders in the form of pharmaceutical compositions.

If the EG-VEGF polypeptide is targeted intracellularly and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA*, 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

G. Uses for Anti-EG-VEGF Antibodies

The anti-EG-VEGF antibodies of the invention have various utilities. For example, anti-EG-VEGF antibodies may be used in diagnostic assays for EG-VEGF, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-EG-VEGF antibodies also are useful for the affinity purification of EG-VEGF from recombinant cell culture or natural sources. In this process, the antibodies against EG-VEGF are immobilized on a suitable support, such a Sephadex resin or filter paper, using methods well known in the art. The immobilized antibody then is contacted with a sample containing the EG-VEGF to be purified, and thereafter the support is washed with a suitable solvent that will remove substantially all the material in the sample except the EG-VEGF, which is bound to the immobilized antibody. Finally, the support is washed with another suitable solvent that will release the EG-VEGF from the antibody. In addition, anti-EG-VEGF antibodies are useful as therapeutic and diagnostic agent, and can be used for the treatment and/or diagnosis of the conditions discussed before in connection with EG-VEGF and EG-VEGF antagonists.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Isolation of cDNA Clones Encoding a Human EG-VEGF

DNA60621-1516 was identified by applying a proprietary signal sequence finding algorithm (FIG. 20A-Q) developed by Genentech, Inc. (South San Francisco, Calif.) upon ESTs as well as clustered and assembled EST fragments from public (e.g., GenBank) and/or private (LIFESEQ™, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST cluster sequence from the LIFESEQ™ database, Incyte Pharmaceuticals, Palo Alto, database, designated herein as DNA157032. This EST cluster sequence was then compared to a variety of expressed sequence tag (EST) databases which included public EST databases (e.g., GenBank) and a proprietary EST DNA database (LIFESEQ™, Incyte Pharmaceuticals, Palo Alto, Calif.) to identify existing homologies. The homology search was performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is shown in FIG. 4 (SEQ ID NO:3), wherein the consensus sequence is herein designated DNA56748.

In light of an observed sequence homology between the DNA56748 sequence and an EST sequence encompassed within clone no. 3476792 from the Incyte database, clone no. 3476792 was purchased and the cDNA insert was obtained and sequenced. Clone no. 3476792 was isolated from a library from ovarian tissue. Sectioning of the tissue found the posterior serosa contained a focus of endometriosis. Pathology for the associated tumor tissue indicated multiple leiomyomata, ranging in size. It was found herein that that cDNA insert encoded a full-length protein. The sequence of this cDNA insert is shown in FIG. 1 and is herein designated as DNA60621-1516.

Clone DNA60621-1516 contains a single open reading frame with an apparent translational initiation site at nucleotide positions 91-93 and ending at the stop codon at nucleotide positions 406-408 (FIG. 1). The predicted polypeptide precursor is 105 amino acids long (FIG. 2). The full-length EG-VEGF protein shown in FIG. 2 has an estimated molecular weight of about 11715 daltons and a pI of about 9.05. Mature EG-VEGF is an 8600 dalton protein encoded by a cDNA cloned from a human ovary library. The 1.4 kilobase cDNA encodes a protein of 105 amino acids with a well defined signal sequence. EG-VEGF is a cysteine-rich protein comprised of a colipase fold motif. Of the 86 amino acids expected in the mature protein, 10 are cysteines (FIGS. 15*a* and *b*). The protein has a series of short beta strands with large connecting loops which are held together by disulfide bonds resulting in a flat fold with finger-like projections that act as interactive surfaces. Analysis of the full-length EG-VEGF sequence shown in FIG. 2 (SEQ ID NO:2) evidences the presence of a variety of important polypeptide domains as shown in FIG. 2, wherein the locations given for those important polypeptide domains are approximate as described above. Clone DNA60621-1516 has been deposited with ATCC on Aug. 4, 1998 and is assigned ATCC Deposit No. 203091.

An analysis of the Dayhoff database (version 35.45 SwissProt 35), using the ALIGN-2 sequence alignment analysis of the full-length sequence shown in FIG. 2 (SEQ ID NO:2), evidenced sequence identity between the EG-VEGF amino acid sequence and the following Dayhoff sequences: VRPA_DENPO, LFE4_CHICK, AF034208_1, AF030433_1, A55035, COL_RABIT, CELB0507_9, S67826_1, S34665 and CRU73817_1.

Remarkably, EG-VEGF displays a high degree of homology (80%) and identity (63%) to a non-toxic protein purified from the venom of black mamba snake *Dendroaspis polylepis polylepis*, and named venom protein A (VPRA) [Joubert and Strydom, *Hoppe-Seylers Zeitschrift fur Phys. Chemie*, 361: 1787-1794 (1980)] and a high degree of homology (76%) and identity (58%) to a human molecule closely related to a peptide isolated from *Bombina variegata*, and termed "Bv8" [Wechselberger et al., *FEBS Lett.*, 462:177-181 (1999)]. FIG. 15b illustrates this homology. In FIG. 15b, boxed residues indicate identity and human EG-VEGF, snake VPRA, and human BV8 homologue (Bv8 horn) amino acid sequences are indicated. Notably, the number and spacing of cysteines for EG-VEGF are completely conserved. Thus, EG-VEGF is the human orthologue or a closely related homologue of VPRA and Bv8. EG-VEGF displays a more limited but significant homology with the cysteine-rich carboxyl sequence of the *Xenopus* head organizer dickkopf, an inhibitor of wnt signaling, and to colipase, as can be seen in FIG. 15c [Glinka et al., *Nature*, 391:357-362; Aravind and Koonin, *Curr. Biology*, 8:477-478 (1998)]. FIG. 15c is an alignment of human EG-VEGF, human dickkopf-3 (hdkk3) [Krupnik et al., *Gene*, 238:301-313 (1999)], *Xenopus* dkk-1 (xdkk1) [Glinka et al., *Nature*, 391:357-362 (1998)] and porcine colipase (col). This illustrates the conserved cysteines which form the characteristic disulfide-bonding pattern of the colipase fold domain [van Tilbeurgh et al., *Nature*, 359:159-162 (1992)]. This motif in EG-VEGF is 37% identical and 41% homologous to the cysteine rich C-terminal domain of human dkk-3 and 32% identical, 42% homologous to the *Xenopus* dkk-1 domain. Numbers indicate amino acid position in the respective protein and boxed residues are identical to EG-VEGF.

Example 2

Use of EG-VEGF as a Hybridization Probe

The following method describes use of a nucleotide sequence encoding EG-VEGF as a hybridization probe.

DNA comprising the coding sequence of full-length or mature EG-VEGF is employed as a probe to screen for homologous DNAs (such as those encoding naturally-occurring variants of EG-VEGF) in human tissue cDNA libraries or human tissue genomic libraries.

Hybridization and washing of filters containing either library DNAs is performed under the following high stringency conditions. Hybridization of radiolabeled EG-VEGF-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence EG-VEGF can then be identified using standard techniques known in the art.

Example 3

Expression of EG-VEGF in *E. coli*

This example illustrates preparation of an unglycosylated form of EG-VEGF by recombinant expression in *E. coli*.

The DNA sequence encoding EG-VEGF is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a tip promoter, a polyhis leader (including the first six STII codons, polyhis sequence, and enterokinase cleavage site), the EG-VEGF coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized EG-VEGF protein can then be purified using a metal chelating column under conditions that allow tight binding of the protein.

EG-VEGF may be expressed in *E. coli* in a poly-His tagged form, using the following procedure. The DNA encoding EG-VEGF is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) lon galE rpoHts(htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate 2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

E. coli paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded EG-VEGF polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Example 4

Expression of EG-VEGF in Mammalian Cells

This example illustrates preparation of a potentially glycosylated form of EG-VEGF by recombinant expression in mammalian cells.

The vector, pRK5 (see EP 307,247, published Mar. 15, 1989), is employed as the expression vector. Optionally, the EG-VEGF DNA is ligated into pRK5 with selected restriction enzymes to allow insertion of the EG-VEGF DNA using ligation methods such as described in Sambrook et al., supra. The resulting vector is called pRK5-EG-VEGF.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-EG-VEGF DNA is mixed with about 1 µg DNA encoding the VA RNA gene [Thimmappaya et al., Cell, 31:543 (1982)] and dissolved in 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of EG-VEGF polypeptide. The cultures containing transfected cells may undergo further incubation (in serum free medium) and the medium is tested in selected bioassays.

In an alternative technique, EG-VEGF may be introduced into 293 cells transiently using the dextran sulfate method described by Somparyrac et al., Proc. Natl. Acad. Sci., 12:7575 (1981). 293 cells are grown to maximal density in a spinner flask and 700 µg pRK5-EG-VEGF DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed EG-VEGF can then be concentrated and purified by any selected method, such as dialysis and/or column chromatography.

In another embodiment, EG-VEGF can be expressed in CHO cells. The pRK5-EG-VEGF can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of EG-VEGF polypeptide, the culture medium may be replaced with serum free medium. Preferably, the cultures are incubated for about 6 days, and then the conditioned medium is harvested. The medium containing the expressed EG-VEGF can then be concentrated and purified by any selected method.

Epitope-tagged EG-VEGF may also be expressed in host CHO cells. The EG-VEGF may be subcloned out of the pRK5 vector. The subclone insert can undergo PCR to fuse in frame with a selected epitope tag such as a poly-his tag into a Baculovirus expression vector. The poly-his tagged EG-VEGF insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged EG-VEGF can then be concentrated and purified by any selected method, such as by $Ni^{2+}$-chelate affinity chromatography.

EG-VEGF may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect™ (Quiagen), Dosper™ or Fugene™ (Boehringer Mannheim). The cells are grown as described in Lucas et al., supra. Approximately $3 \times 10^{-7}$ cells are frozen in an ampule for further growth and production as described below.

The ampules containing the plasmid DNA are thawed by placement into water bath and mixed by vortexing. The contents are pipetted into a centrifuge tube containing 10 nits of media and centrifuged at 1000 rpm for 5 minutes. The supernatant is aspirated and the cells are resuspended in 10 mL of selective media (0.2 µm filtered PS20 with 5% 0.2 µm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3L production spinner is seeded at $1.2 \times 10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 □m filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 5

Expression of EG-VEGF in Yeast

The following method describes recombinant expression of EG-VEGF in yeast.

First, yeast expression vectors are constructed for intracellular production or secretion of EG-VEGF from the ADH2/GAPDH promoter. DNA encoding EG-VEGF and the promoter is inserted into suitable restriction enzyme sites in the selected plasmid to direct intracellular expression of EG-VEGF. For secretion, DNA encoding EG-VEGF can be cloned into the selected plasmid, together with DNA encoding the ADH2/GAPDH promoter, a native EG-VEGF signal peptide or other mammalian signal peptide, or, for example, a yeast alpha-factor or invertase secretory signal/leader sequence, and linker sequences (if needed) for expression of EG-VEGF.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant EG-VEGF can subsequently be isolated and purified by removing the yeast cells from the fermentation medium by centrifugation and then concentrating the medium using selected cartridge filters. The concentrate containing EG-VEGF may further be purified using selected column chromatography resins.

Example 6

Expression of EG-VEGF in Baculovirus-Infected Insect Cells

The following method describes recombinant expression of EG-VEGF in Baculovirus-infected insect cells.

The sequence coding for EG-VEGF is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (PharMingen). Briefly, the sequence encoding EG-VEGF or the desired portion of the coding sequence of EG-VEGF such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

For example, the coding sequences of human EG-VEGF were amplified by PCR and subcloned into the EcoRI and StuI sites of pBPH.IgG to generate a C-terminal fusion with the Fc region of human IgG1 or into the EcoRI and SmaI sites of pBPH.His.c to generate a C-terminal GHHHHHHHH tag. Vectors pBPH.IgG and pBPH.His.c are derivatives of the baculovirus expression vector PVL1393 (PharMingen).

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 2-4 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged EG-VEGF can then be purified, for example, by either protein A-Sepharose beads (Pharmacia) for Fc fusion proteins or Ni-NTA agarose beads (Qiagen) for His-tagged proteins. For His-tagged proteins, extracts are prepared from recombinant virus-infected Sf9 cells as described by Rupert et al., *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 µm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged EG-VEGF are pooled and dialyzed against loading buffer.

Alternatively, purification of the IgG tagged (or Fc tagged) EG-VEGF can be performed using known chromatography techniques, including for instance, Protein A or protein G column chromatography.

To examine protein expression, SDS/PAGE analysis was performed on the affinity-purified, recombinant proteins under non-reducing and reducing conditions, followed by staining. Proteins were routinely submitted for N-terminal sequencing and endotoxin measurements, which were below 1 eu/mg.

Example 7

Preparation of Antibodies that Bind EG-VEGF

This example illustrates preparation of monoclonal antibodies which can specifically bind EG-VEGF.

Techniques for producing the monoclonal antibodies are known in the art and are described, for instance, in Goding, supra. Immunogens that may be employed include purified EG-VEGF, fusion proteins containing EG-VEGF, and cells expressing recombinant EG-VEGF on the cell surface. Selection of the immunogen can be made by the skilled artisan without undue experimentation.

Mice, such as Balb/c, are immunized with the EG-VEGF immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-EG-VEGF antibodies.

After a suitable antibody titer has been detected, the animals "positive" for antibodies can be injected with a final intravenous injection of EG-VEGF. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against EG-VEGF. Determination of "positive" hybridoma cells secreting the desired monoclonal antibodies against EG-VEGF is within the skill in the art.

The positive hybridoma cells can be injected intraperitoneally into syngeneic Balb/c mice to produce ascites containing the anti-EG-VEGF monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 8

Purification of EG-VEGF Polypeptides Using Specific Antibodies

Native or recombinant EG-VEGF polypeptides may be purified by a variety of standard techniques in the art of protein purification. For example, pro-EG-VEGF polypeptide, mature EG-VEGF polypeptide, or pre-EG-VEGF polypeptide is purified by immunoaffinity chromatography using antibodies specific for the EG-VEGF polypeptide of interest. In general, an immunoaffinity column is constructed by covalently coupling the anti-EG-VEGF polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of EG-VEGF polypeptide by preparing a fraction from cells containing EG-VEGF polypeptide in a soluble form. This preparation is derived by solubilization of the whole cell or of a subcellular fraction obtained via differential centrifugation by the addition of detergent or by other methods well known in the art. Alternatively, soluble EG-VEGF polypeptide containing a signal sequence may be secreted in useful quantity into the medium in which the cells are grown.

A soluble EG-VEGF polypeptide-containing preparation is passed over the immunoaffinity column, and the column is washed under conditions that allow the preferential absorbance of EG-VEGF polypeptide (e.g., high ionic strength buffers in the presence of detergent). Then, the column is eluted under conditions that disrupt antibody/EG-VEGF polypeptide binding (e.g., a low pH buffer such as approximately pH 2-3, or a high concentration of a chaotrope such as urea or thiocyanate ion), and EG-VEGF polypeptide is collected.

Example 9

Drug Screening

This invention is particularly useful for screening compounds by using EG-VEGF polypeptides or binding fragment thereof in any of a variety of drug screening techniques. The EG-VEGF polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the EG-VEGF polypeptide or fragment. Drugs are screened against such transformed cells in competitive binding assays. Such cells, either in viable or fixed form, can be used for standard binding assays. One may measure, for example, the formation of complexes between EG-VEGF polypeptide or a fragment and the agent being tested. Alternatively, one can examine the diminution in complex formation between the EG-VEGF polypeptide and its target cell or target receptors caused by the agent being tested.

Thus, the present invention provides methods of screening for drugs or any other agents which can affect a EG-VEGF polypeptide-associated disease or disorder. These methods comprise contacting such an agent with an EG-VEGF polypeptide or fragment thereof and assaying (I) for the presence of a complex between the agent and the EG-VEGF polypeptide or fragment, or (ii) for the presence of a complex between the EG-VEGF polypeptide or fragment and the cell, by methods well known in the art. In such competitive binding assays, the EG-VEGF polypeptide or fragment is typically labeled. After suitable incubation, free EG-VEGF polypeptide or fragment is separated from that present in bound form, and the amount of free or uncomplexed label is a measure of the ability of the particular agent to bind to EG-VEGF polypeptide or to interfere with the EG-VEGF polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a EG-VEGF polypeptide, the peptide test compounds are reacted with EG-VEGF polypeptide and washed. Bound EG-VEGF polypeptide is detected by methods well known in the art. Purified EG-VEGF polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding EG-VEGF polypeptide specifically compete with a test compound for binding to EG-VEGF polypeptide or fragments thereof. In this manner, the antibodies can be used to detect the presence of any peptide which shares one or more antigenic determinants with EG-VEGF polypeptide.

The present invention also provides for methods of screening for a bioactive agent that is capable of modulating the activity of EG-VEGF. In these method a candidate bioactive agent is added to a sample of EG-VEGF and it is determined if an alteration in the biological activity of EG-VEGF results. Such an alteration might be in EG-VEGF's ability to stimulate cell proliferation, to induce chemotaxis, to stimulate angiogenesis, to induce cell differentiation or to phosphorylate ERK1 and ERK2.

Example 10

Rational Drug Design

The goal of rational drug design is to produce structural analogs of biologically active polypeptide of interest (i.e., a EG-VEGF polypeptide) or of small molecules with which they interact, e.g., agonists, antagonists, or inhibitors. Any of these examples can be used to fashion drugs which are more active or stable forms of the EG-VEGF polypeptide or which enhance or interfere with the function of the EG-VEGF polypeptide in vivo (c.f., Hodgson, *Bio/Technology*, 9: 19-21 (1991)).

In one approach, the three-dimensional structure of the EG-VEGF polypeptide, or of an EG-VEGF polypeptide-inhibitor complex, is determined by x-ray crystallography, by computer modeling or, most typically, by a combination of the two approaches. Both the shape and charges of the EG-VEGF polypeptide must be ascertained to elucidate the structure and to determine active site(s) of the molecule. Less often, useful information regarding the structure of the EG-VEGF polypeptide may be gained by modeling based on the structure of homologous proteins. In both cases, relevant structural information is used to design analogous EG-VEGF polypeptide-like molecules or to identify efficient inhibitors. Useful examples of rational drug design may include molecules which have improved activity or stability as shown by Braxton and Wells, *Biochemistry*, 31:7796-7801 (1992) or which act as inhibitors, agonists, or antagonists of native peptides as shown by Athauda et al., *J. Biochem.*, 113:742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the EG-VEGF polypeptide may be made available to perform such analytical studies as X-ray crystallography. In addition, knowledge of the EG-VEGF polypeptide amino acid sequence provided herein will provide guidance to those employing computer modeling techniques in place of or in addition to x-ray crystallography.

Example 11

Northern Blot Analysis

To elucidate the expression pattern of EG-VEGF, Northern blot analysis was performed using RNA from a wide variety of human tissues. Human RNA blots were hybridized to a $^{32}$P-labelled DNA probe based on the EG-VEGF cDNA. Human multiple tissue polyA+RNA array and human polyA+ RNA multiple tissue northern blots were purchased from Clontech. Other northern blots used included human fetal RNA blot MTN (Clontech) and human adult RNA blot MTN-II (Clontech).

Northern blot analysis was performed according to methods well known in the art. For example, cDNA probes were prepared using 30-50 ng of the human or mouse cDNA fragments with the Redi-Prime II kit (Amersham), using $^{32}$P-dCTP 3000 μCi/mmol (Amersham). Probes were purified on Sephadex G50 spin columns (Pharmacia) and hybridization was carried out at 68° C. in ExpressHyb hybridization solution (Stratagene). In another example, blots were incubated with the probes in hybridization buffer (5×SSPE; 2 ×Denhardt's solution; 100 mg/mL denatured sheared salmon sperm DNA; 50% formamide; 2% SDS) for 60 hours at 42° C. The blots were washed several times in 2×SSC; 0.05% SDS for 1 hour at room temperature, followed by a 30 minute wash in 0.1×SSC; 0.1% SDS at 50° C. The blots were developed after overnight exposure by phosphorimager analysis (Fuji). Equivalent RNA loading was assessed by hybridization with the control actin probe.

Figure 18:
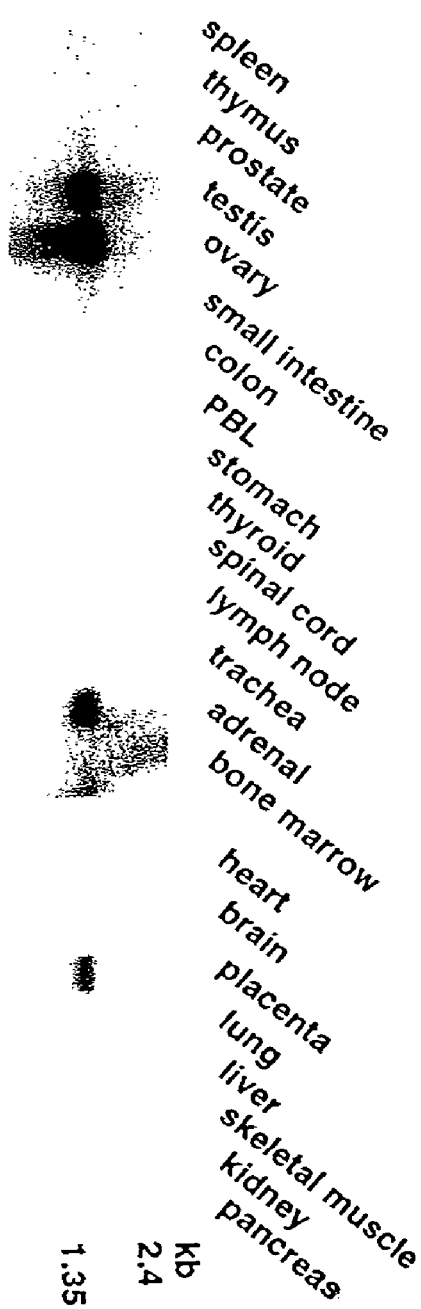
FIG. 18 shows northern blot analysis of EG-VEGF expression. Northern blot analyses of human RNA samples revealed a single transcript of approximately 1.4 kb. Expression is highest in ovary and testis, followed by adrenal and placenta. A less abundant signal, apparent after longer exposure, is present in prostate. Equivalent RNA loading was assessed by hybridization with the control actin probe (data not shown). Contents of the lanes are indicated above the blots, and the size (kb) is indicated at the right.

EG-VEGF mRNA transcripts were detected. FIG. 18 shows that, in several independent experiments, a single mRNA species of 1.4 kb was expressed, in decreasing order of intensity, in ovary, testis, adrenal gland and placenta. No expression was detected in any other tissue, with the exception of a very weak signal in the prostate after prolonged exposure (FIG. 18). Similar findings were obtained by in situ hybridization in human multi-tissue arrays (data not shown). These findings indicate that steroidogenic endocrine glands are the major site of expression of EG-VEGF mRNA.

Example 12

In Situ Ligand Binding

To identify the cell types that express EG-VEGF, in situ hybridization studies were performed using a series of testis and ovary specimens from human and other primates. Several sets of experiments were performed, one set using fluorescence and one using labelled probes.

In the first set of experiments, unfixed, fresh tissue embedded in OCT was sectioned at 10 microns and stored at −20° C. for 4 days without desiccant. All steps were carried out at room temperature, with the exception of the fixation, performed at 4° C. Sections were incubated in 35 mM acetic acid (pH 3.5), 3 mM CaCl$_2$, 3 mM MgSO$_4$, 5 mM KCl, 1 M NaCl for 4 minutes. The slides were washed 3 times with HEPES buffered saline plus cation buffer (25 mM Hepes (pH7/2), 150 mM NaCl, 3 mM CaCl$_2$, 3 mM MgSO$_4$, 5 mM Kcl, and 32 mM sucrose) prior to blocking with 1.5% mouse serum in HBS-C plus protease inhibitors (Boehringer Mannheim) for 20 minutes. Further blocking was carried out using the avidin/biotin blocking kit from Vector Laboratories. The initial experiment used liver, adrenal gland and ovary prepared from adult rat. As described below, other tissues were analyzed. These sections were incubated with ligand, ranging from 0 to 1.5 nM EG-VEGF-Fc, for 60 minutes. Displacement was achieved using excess EG-VEGF-his tagged protein. Sections were washed with HBS-C with 0.1% BSA 3 times, and then fixed for 10 minutes in 4% paraformaldehyde. A 1:4000 dilution of secondary antibody, biotinylated goat anti-human Fc (Jackson Laboratories) with 1.5% mouse serum in HBS-C, was added to sections for 30 minutes. After washing, sections were post-fixed for 10 minutes in paraformaldehyde. Slides were washed with TBS (100 mM Tris-HCl (pH8.0), 150 mM NaCl) twice and then treated with 3% H$_2$O$_2$ in TBS for 10 minutes. Following washes with TBS, sections were reacted with Dupont TSA kit components, HRP-streptavidin at 1:1000 and biotinylated tyramide 1:50 in amplification diluent. Finally, FITC-conjugated streptavidin (DAKO), 1:1000 dilution in TBS, was reacted for 30 minutes. After extensive washing in TBS with 0.05% Tween-20, coverslips were applied using Vectashield mounting media. Images were obtained using the FITC channel of a fluorescent microscope. In some cases, DAPI (e.g., Molecular Probes), a nucleic acid stain was used. DAPI can be excited with a mercury-arc lamp or with the UV lines of the argon-ion laser. Additionally, hematoxylin-eosin stains were used according to standard methods previously described in order to show the structure of the tissue where expression was demonstrated.

Figure 5B:
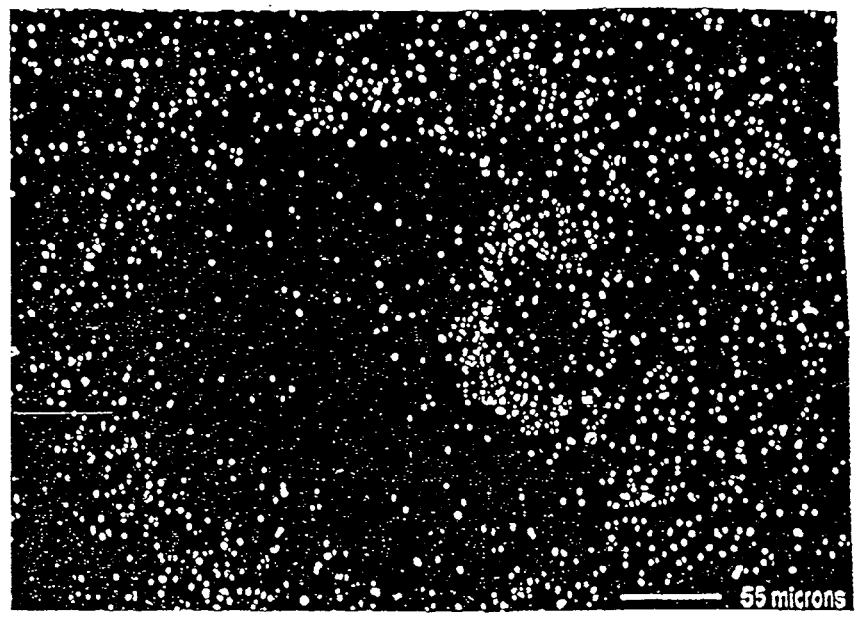
Figure 5C:
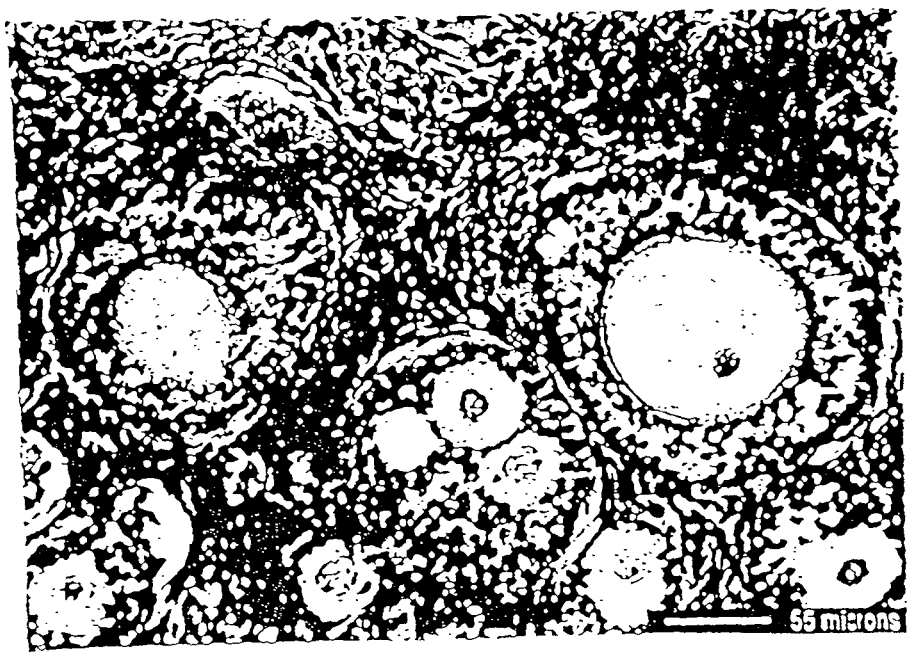
Figure 5D:
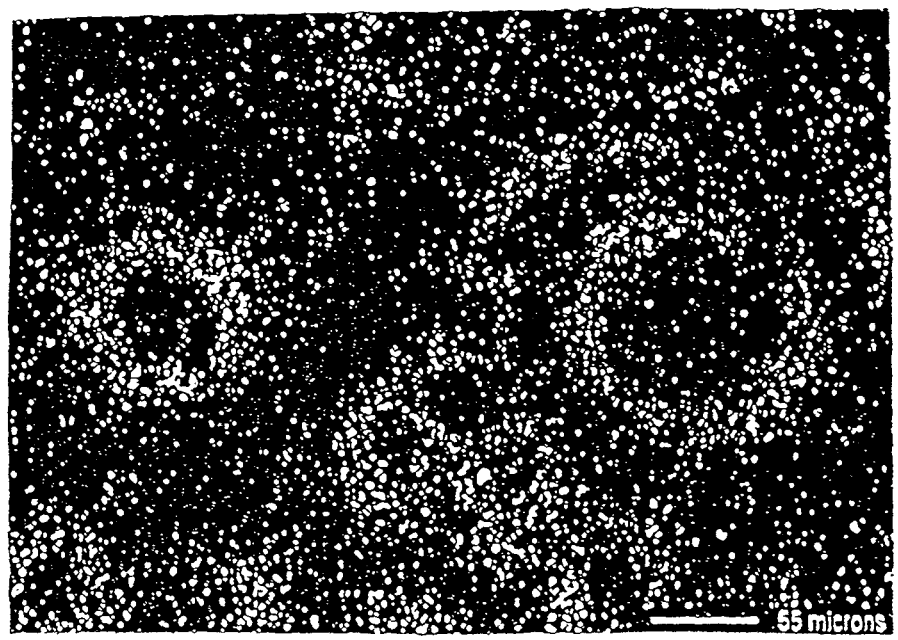
Figure 5E:
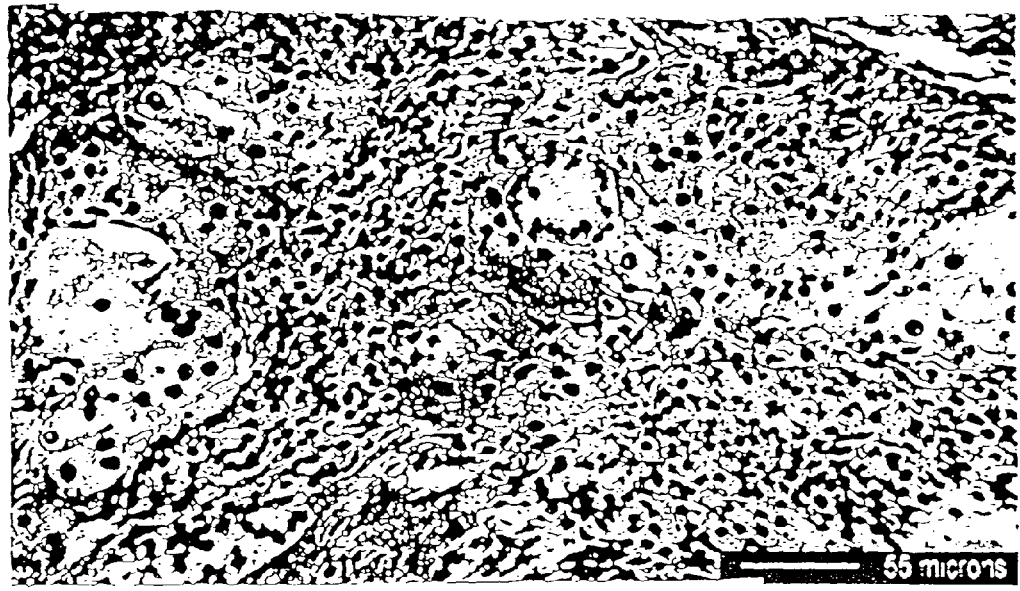
Figure 5F:
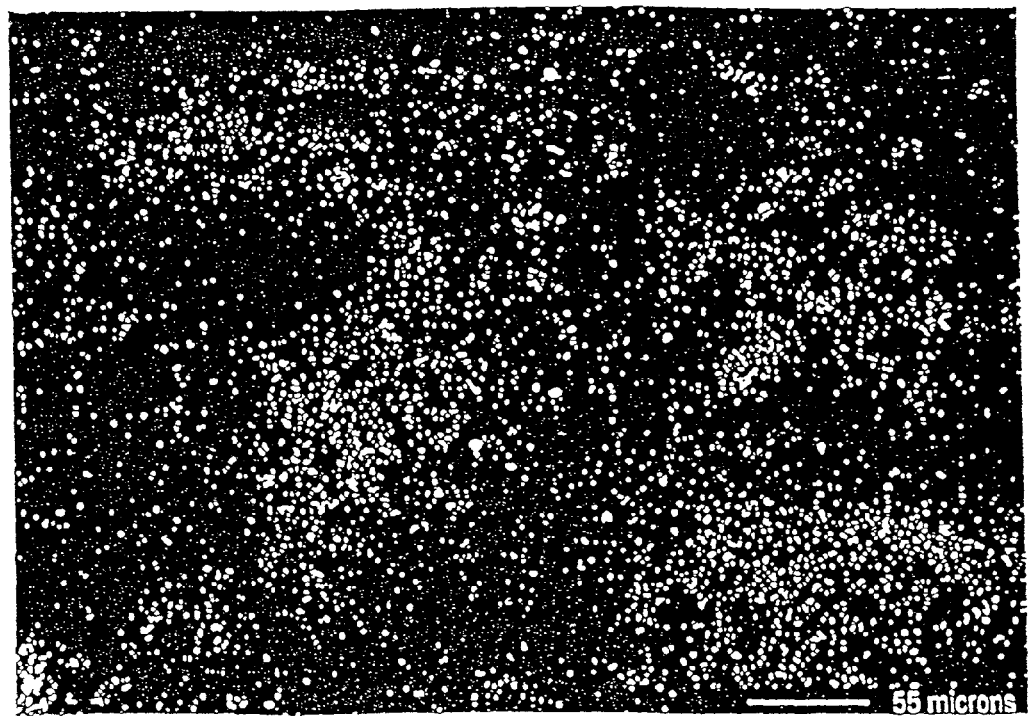

In chimp and monkey ovaries, the most intense signal was over the granulosa cells, especially those nearest to the oocyte, in primary follicles. Weaker signal was present over granulosa cells in primordial follicles and in cumulus oophorus. Significant signal was present in the ovarian cortex, especially around small, involuted corpora lutea (cyno monkey sample) and in poorly defined clusters of cells at the vascular pole of the ovary. The results are shown in FIGS. 5A-F (all at 55 microns). FIG. 5A shows a hematoxylin-eosin stain and FIG. 5B shows EG-VEGF expression of EG-VEGF using FITC in the ovary of a 2 year old chimp. FIG. 5C shows a hematoxylin-eosin stain and FIG. 5D shows EG-VEGF expression using FITC in the ovary of a cyno monkey. FIG. 5E shows a hematoxylin-eosin stain and FIG. 5F shows EG-VEGF expression using FITC in a chimp stromal ovary.

Figure 6A:
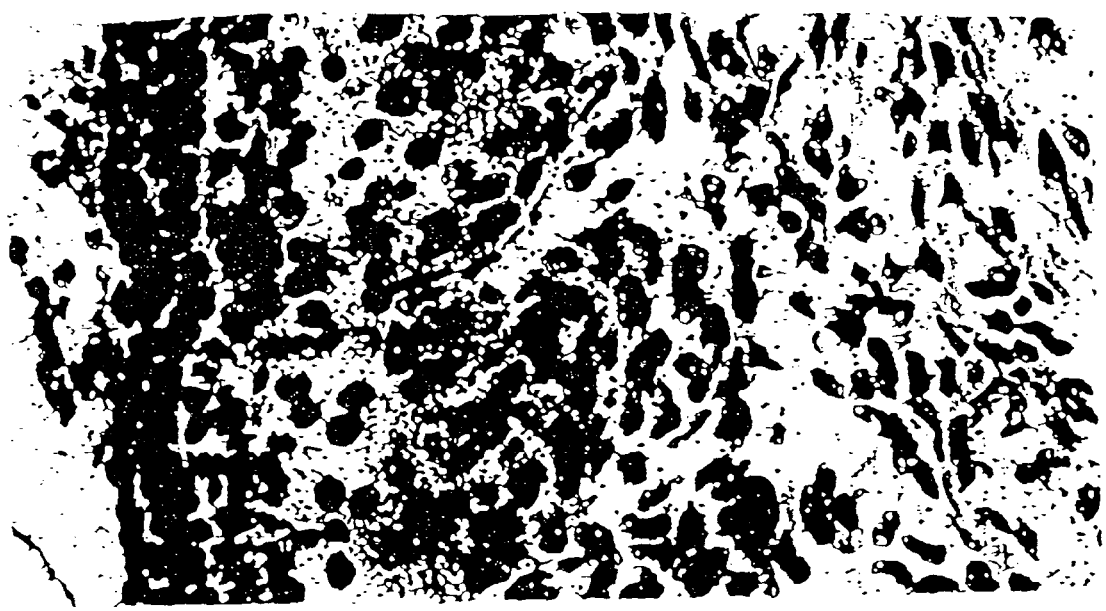
FIGS. 6A-D show actin and EG-ECGF in situ expression in frozen and paraffin-embedded human ovaries.
Figure 6B:
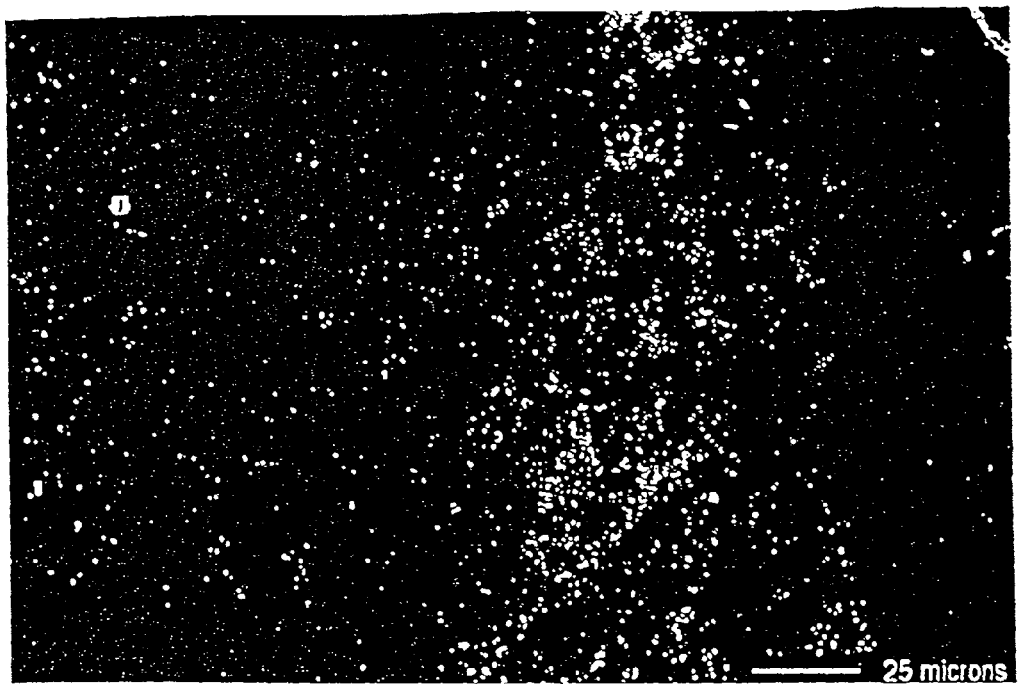
Figure 6C:
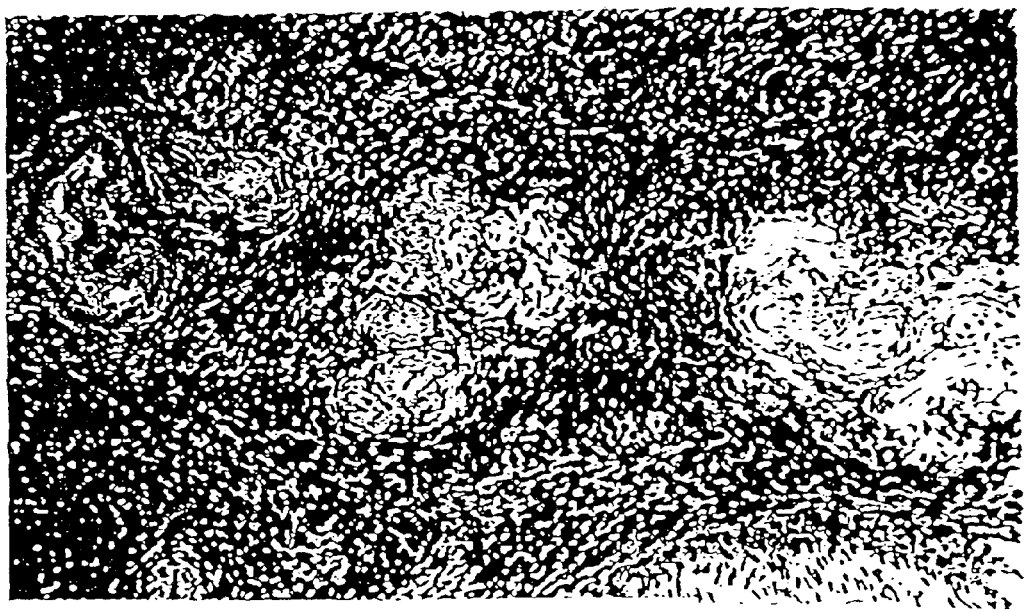
Figure 6D:
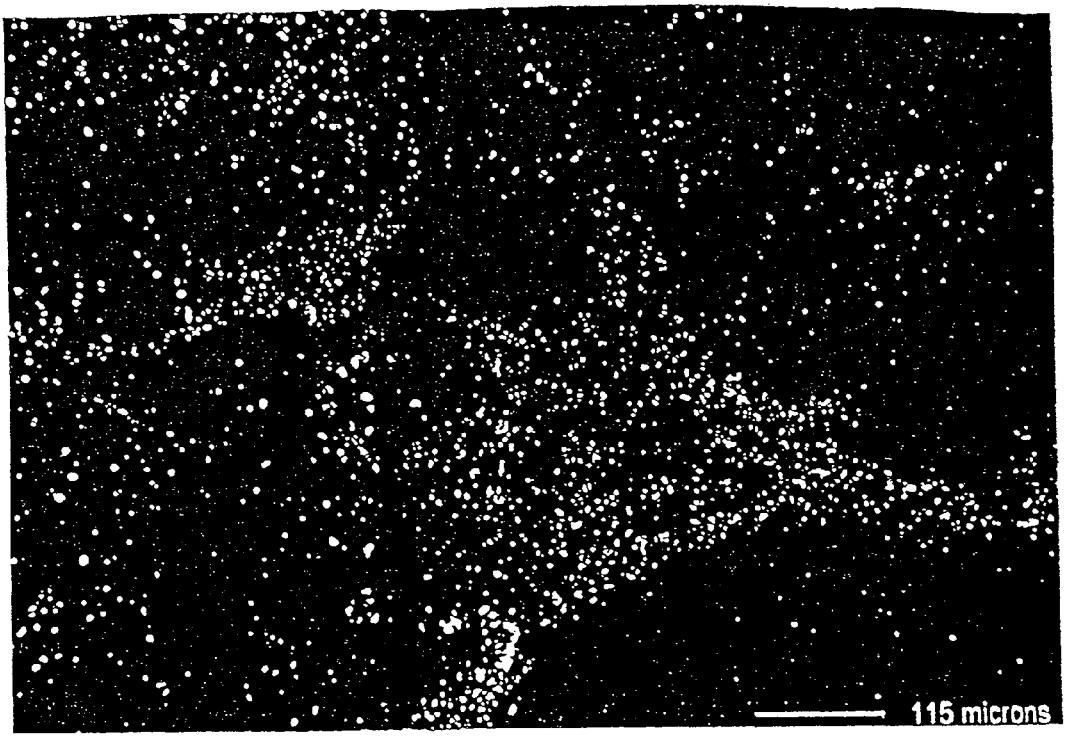

In human ovaries, there was diffuse moderate expression in cortical stroma. The signal was intense over theca externa around corpus hemmorhagicum. Additionally, there was moderate focal positive signal in corpora lutea. The results are shown in FIGS. 6A-D. FIG. 6A shows a hematoxylin-eosin stain and FIG. 6B shows EG-VEGF expression using FITC (25 microns). FIG. 6C shows a hematoxylin-eosin stain and FIG. 6D shows EG-VEGF expression using FITC (115 microns).

Figure 7A:
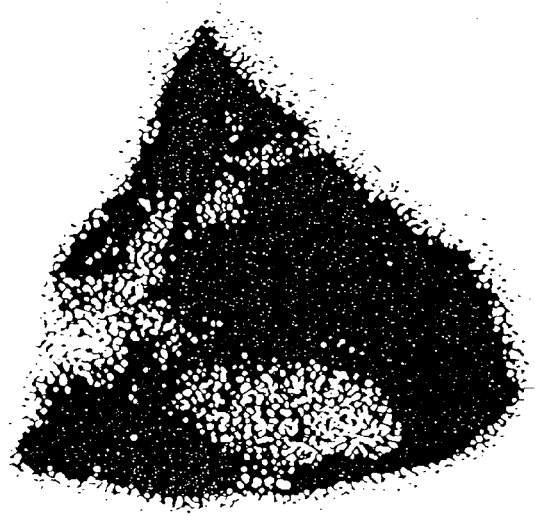
FIG. 7A shows an autoradiogram of EG-ECGF in situ expression in an ovary from a 46 year old woman with uterine prolapse and FIG. 7B shows a hematoxylin-eosin stain of the same ovary.
Figure 7B:

In situ hybridization studies were also performed on an ovary from a 46 year old woman with uterine prolapse. In this case, EG-VEGF was radioactively labeled using standard techniques previously described. The autoradiogram showing EG-VEGF expression is shown in FIG. 7A. FIG. 7B shows a hematoxylin-eosin stain of the same ovary.

Figure 8:
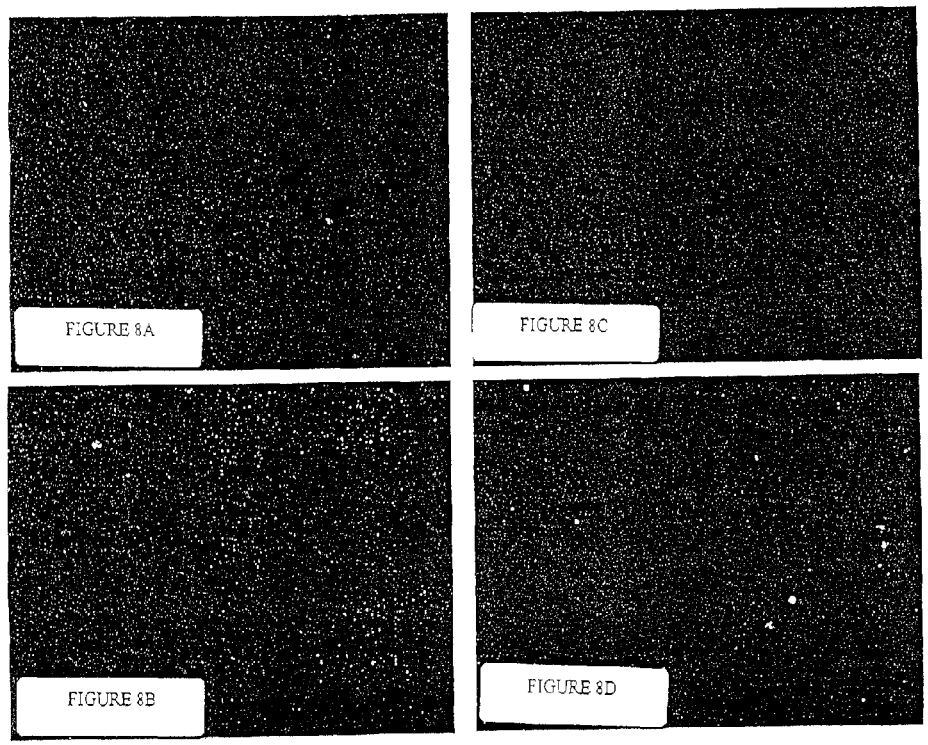
FIGS. 8A-D show EG-ECGF in situ expression in adrenal gland.

Additionally, in situ hybridization studies were performed on rat adrenal cortex tissue sections. FIGS. 8A and 8B show EG-VEGF nucleic acid identification using DAPI and FIGS. 8C and 8D show EG-VEGF protein identification using FITC.

Figure 9:
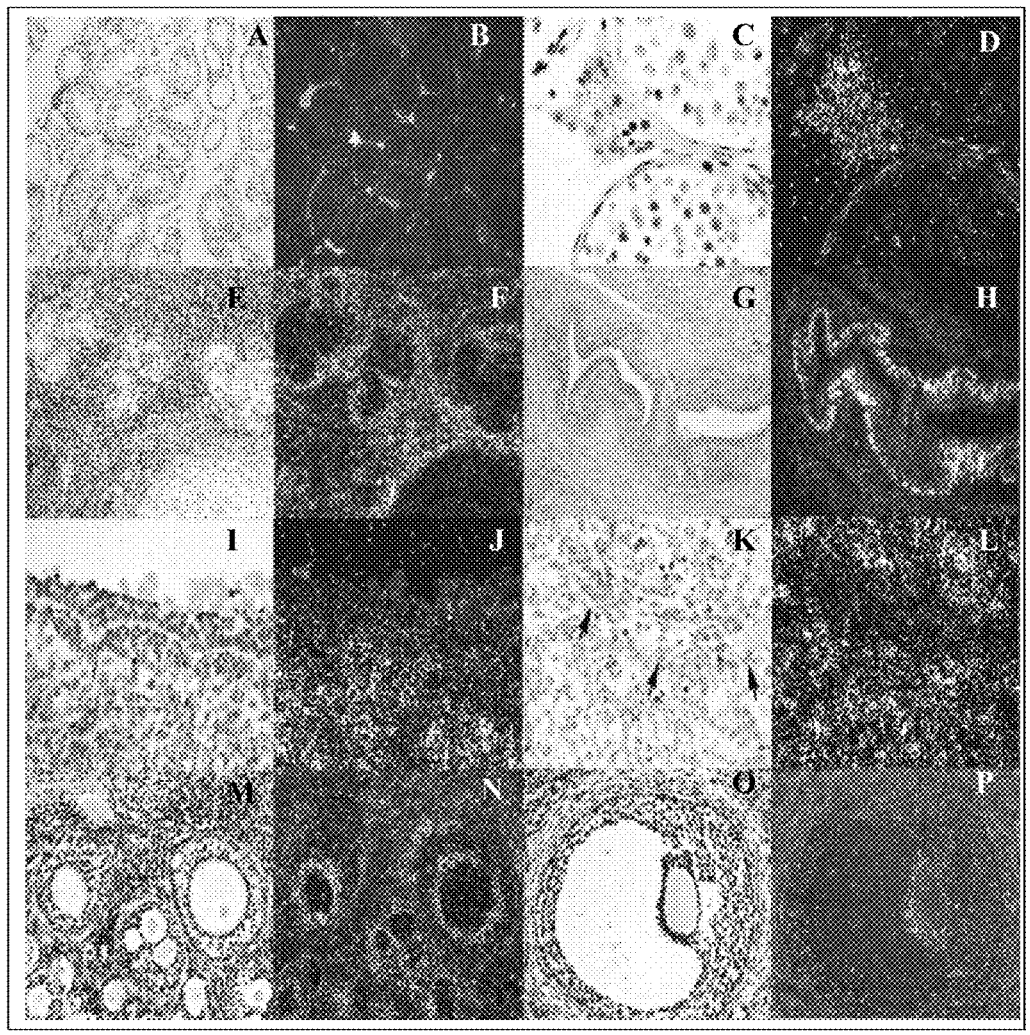
FIG. 9 In situ hybridization studies revealed that in the human testis, EG-VEGF transcript is restricted to the testosterone-producing Leydig cells (panels A-D). E, F) EG-VEGF signal is prevalent in the human ovarian stroma in cells that can be described as perivascular (K,L). A very similar pattern was evidenced in the chimpanzee ovary (data not shown). G,H) A strong signal is detected in the human corpus hemorrhagicum. In human (I,J) and chimpanzee (M, N, O, P) developing follicles, EG-VEGF RNA is expressed in the theca and granulosa cells—both steroidogenic cell types, and the cumulus oophorus. A, C, E, G, I, K, M, O are bright—field images, and B, D, F, H, J, L, N, P the corresponding dark—field images. Arrows point to the course of a blood vessel.

Furthermore, positive in situ hybridization results were found in the following tissues: ovarian carcinoma, papillary serous; ovarian, normal cortex; ovarian cyst, simple cyst; testis, chronic inflammation; normal ovary; ovarian tumor, papillary serous; adrenal adenoma; and normal testis. In the second set of experiments, $^{33}$P-UTP-labelled RNA probes were generated according to methods known in the art. For example, according to the method described in Melton, D. A., et al., *Nucleic Acids Res.,* 12:7035-7056 (1984). Sense and antisense probes were synthesized from a cDNA fragment corresponding to nucleotides 219-958 of the human EG-VEGF sequence. The in situ hybridization was carried out according to methods well known in the art. The results of this set of experiments are shown in FIG. 9. Panels A, C, E, G, I, K, M and O are bright-field images, and B, D, F, H, J, L, N and P are the corresponding dark-field images. Arrows indicate the location of a blood vessel.

In the testis, a strong hybridization signal was detected (FIG. 9, panels A-E). FIG. 9, panels A-E show that this signal was restricted to the testosterone producing Leydig cells. It is noteworthy that the endothelium of the testis has a surprisingly high turnover: as many as 3% of endothelial cells are labeled with BrdU, probably related to the intense metabolic activity associated with spermatogenesis and steroidogenesis [Collin and Bergh, *Int. J. Androl.,* 19:221-228 (1996)]. In this context, Leydig cells are known to be a source of angiogenic and permeability-enhancing factors such as VEGF [Collin, supra]. Interestingly, in these experiments the VEGF hybridization signal was considerably less intense than the EG-VEGF signal (data not shown). In the ovary, intense EG-VEGF mRNA expression was localized to the androgen-producing cortical stroma, the cumulus oophorus, theca and granulosa of developing follicles (FIG. 9, panels F-P). The strong expression of EG-VEGF mRNA within the theca is coincident with the development of a capillary network associated with follicular development and steroid hormone production [Basset, *Am. J. Anat.,* 73:251-278 (1943)], and is consistent with a pro-angiogenic role of EG-VEGF. This expression pattern is essentially similar in the other primate species examined, cynomologus monkey and chimpanzee (FIG. 9, panels G-I and data not shown). While VEGF has a very low expression in the specialized stroma [Ravindranath et al., *Endocrinology,* 131:254-260 (1992)], EG-VEGF is instead strongly expressed (FIG. 9, panels F, G). Interestingly, such stroma becomes intensely hyperplastic and angiogenic, producing excessive amounts of androgens, in the polycystic ovary syndrome [Goldziher and Green, *J. Clin. Endocrino. Meta.,* 22:325-332 (1962)]. In further experiments it was found that EG-VEGF is also highly expressed in human polycystic ovary syndrome (PCO) specimens. The expression pattern of EG-VEGF in the cumulus oophorus (FIG. 9, panels N-P) is very similar to that of VEGF Ravindranath et al., supra; Philips et al., *Endocrinology,* 127:965-967 (1990)]. In the corpus luteum (CL), EG-VEGF expression was localized to discrete nests of cells (data not shown). While EG-VEGF is highly expressed in the ovarian stroma and within developing follicles (FIG. 9, panels D-I and data not shown), VEGF is expressed at the highest level in the CL [Ravindranath et al., supra]. Inactivation of VEGF in rodents [Ferrara et al., *Nat. Med.,* 4:336-340 (1998)] or in primates [Ryan et al., *Toxicol. Pathol.,* 27:78-86 (1999); Fraser et al., *Endocrinology,* 141:995-1000 (2000)] results in a dramatic suppression of CL development. However, follicular development proceeds almost unimpaired (unpublished observations), indicating that other factors contribute to follicular angiogenesis. It is likely that EG-VEGF contributes to such VEGF-independent angiogenesis. Thus, the partially complementary expression patterns of VEGF and EG-VEGF indicate that these molecules may function in a coordinated or complementary manner to promote angiogenesis in the ovary, and potentially in other tissues that co-express these factors.

Example 13

$^{125}$I EG-VEGF Cell Binding Assays $^{125}$I ligand binding studies were performed with EG-VEGF to characterize the receptor distribution on a variety of cell types. In one case, EG-VEGF-tagged protein, 500 μg, was labeled with 0.5 mCi $^{125}$I using the Iodobead preparation from Pierce. The labeled protein was purified on a C18 Sep Pak in 50% acetonitrile, 0.1% TFA. In a second set of experiments, EG-VEGF was iodinated by the lactoperoxidase method using Na$^{125}$I (Amersham) and the labeled protein was subsequently purified by reverse phase chromatography using a prepacked SynChropak RP HPLC C4 column (Micra Scientific, Inc.). The specific activity of the molecule ranged from 49 to 70 μCi/μg. Competitive binding assays were performed on various cell types including Cos cells. Cells were cultured for 2-3 days in 24-well dishes prior to binding.

In one set of experiments, assays were performed using 0.2 to 0.4 nM labeled ligand and unlabeled EG-VEGF-his as competitor. The highest concentration of unlabeled EG-VEGF-his used in the assays was 270 nM, and a three-fold dilution series for the next 10 concentrations of competitor. bFGF and VEGF were also included as competitors (at 500-fold molar excess), with neither ligand displacing the labeled EG-VEGF-his.

In another set of experiments, competition assays were performed by adding unlabeled, tagged EG-VEGF at 3-fold serial dilutions starting at 270 nM for 12 concentrations in at least duplicate. In other experiments, unrelated ligands including bFGF and VEGF at 200-molar excess were added to confirm specific binding. Ligand binding data was analyzed using the New Ligand program.

Figure 10:
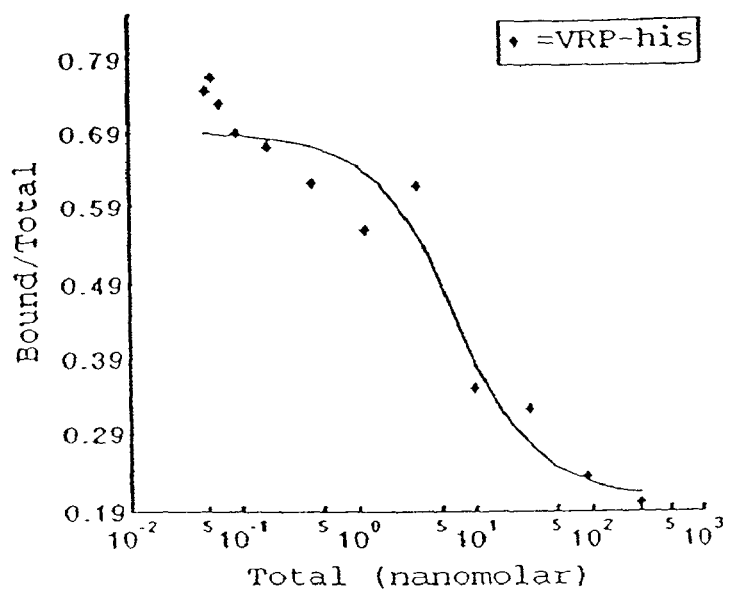
FIGS. 10A-C are a displacement plot and scatchard plot, respectively, showing $^{125}$I-EG-VEGF-his ligand binding analysis in bovine adrenal cortical capillary endothelial cells (ACE).
Figure 10:
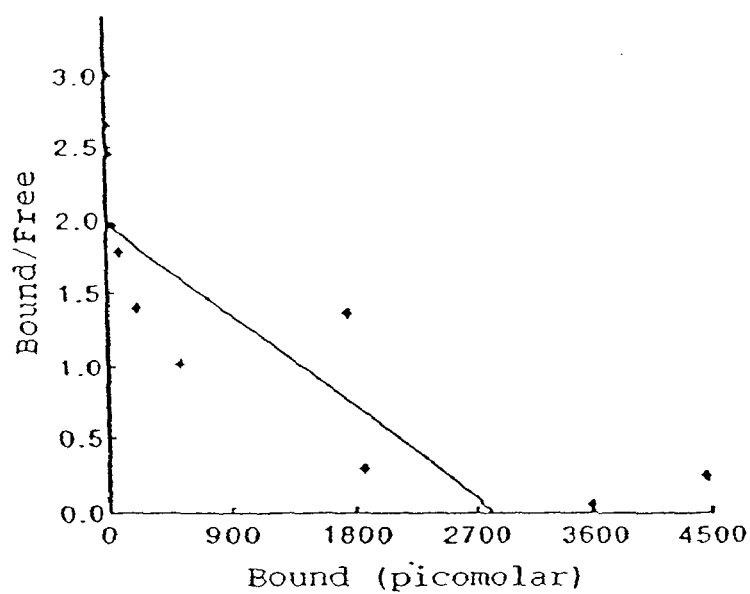
Figure 10C:
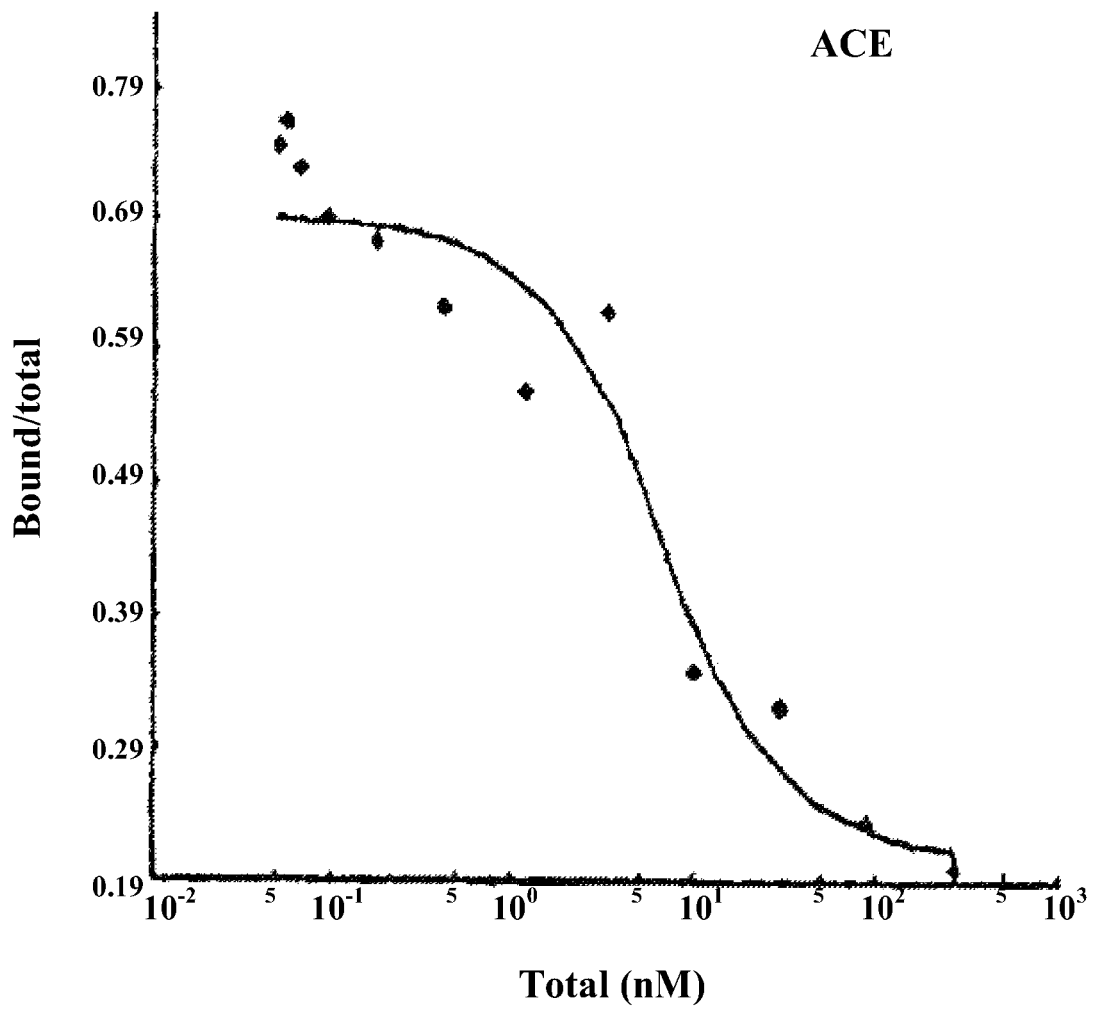
Figure 11:
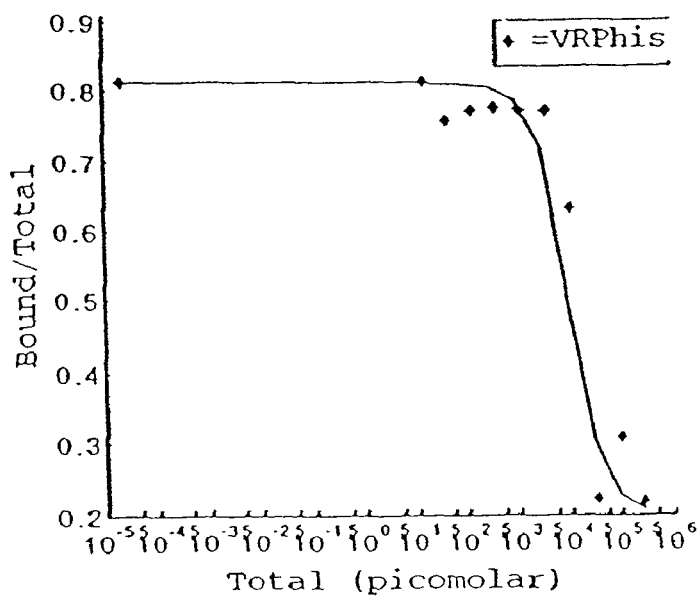
FIGS. 11A-B are a displacement plot and scatchard plot, respectively, showing $^{125}$I-EG-VEGF-his ligand binding analysis in MS-1, a mouse endothelial cell line derived from the endocrine pancreas.
FIG. 11C shows EG-VEGF-his ligand binding analysis in human umbilical vein endothelial cells (HUVEC).
Figure 11:
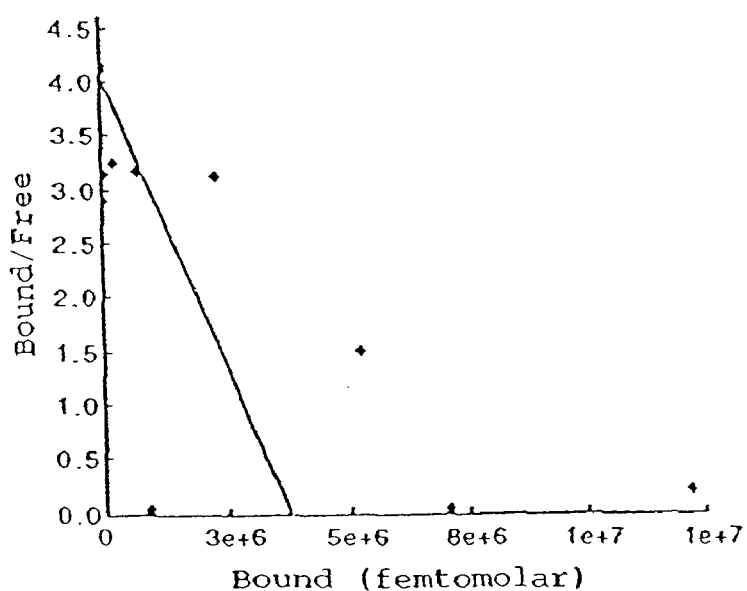
Figure 11C:
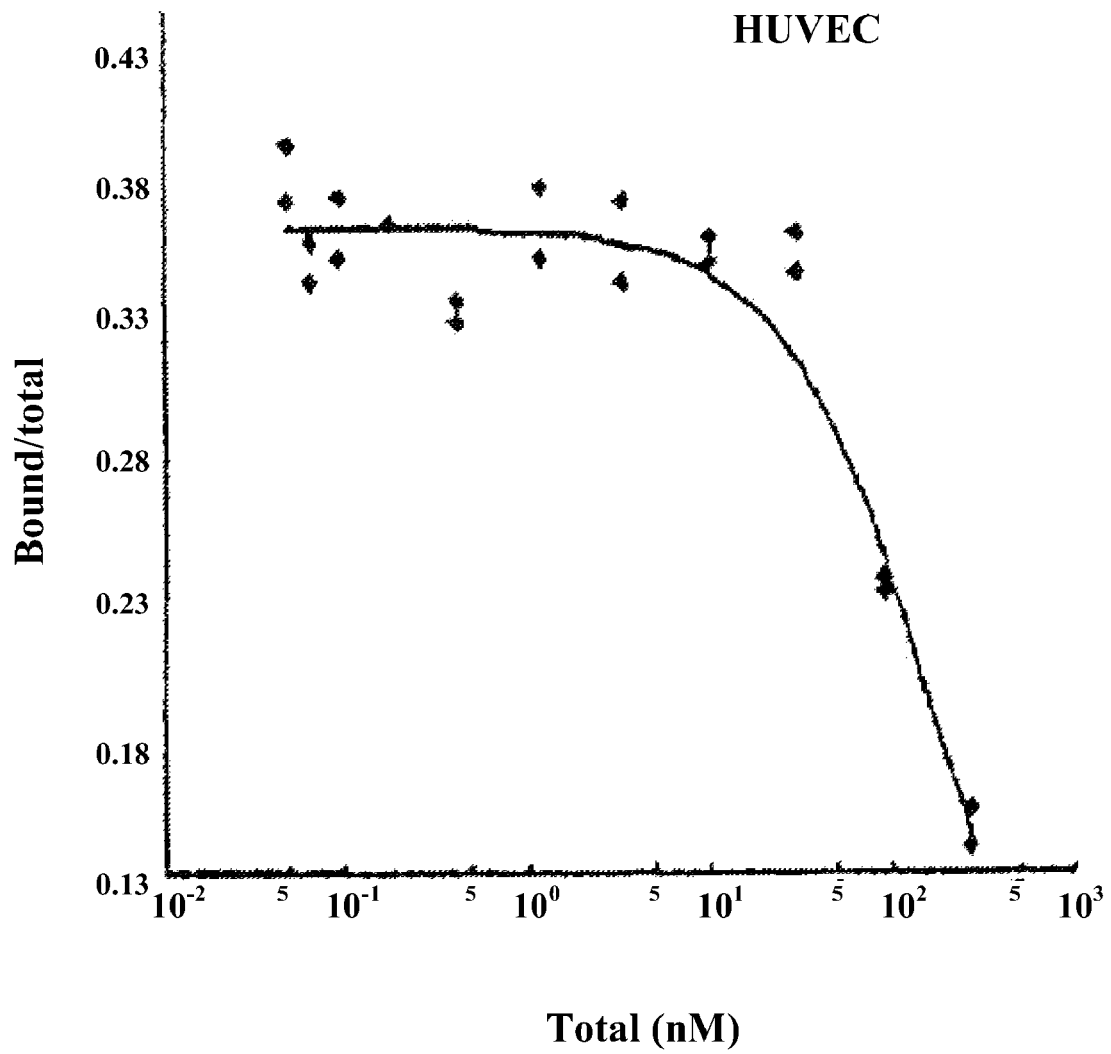

The competition analysis revealed high affinity, specific binding of EG-VEGF to ACE cells with a Kd of 0.9-1.0 nM with an ED$_{50}$-10 nM (FIGS. 10A, 10B, and 10C). A similar high affinity binding was evidenced in MS-1 cells (FIGS. 11A and B). However, other non-responsive cells, including HUVEC, exhibited a low affinity binding component (Kd of >80 nM) or little significant binding and the apparent non-specific, low affinity binding was only displaced at competitor concentrations above 270 nM (FIG. 11C and data not shown). Similarly, 5 other non-responsive cell types assayed did not display the high affinity binding component. Protein cross-linking experiments and membrane protein phosphorylation analyses indicate that the EG-VEGF receptor components are restricted to the specific EG-VEGF responsive cells (data not shown).

Example 14

Cell Proliferation Assays

To determine the spectrum of cell types that respond to EG-VEGF, a panel of endothelial and non-endothelial cell types was assayed for proliferative response. Cells were grown in the presence of a range of concentration of Fc-tagged and His-tagged EG-VEGF ligand for 5-8 days. The cell types assayed included bovine adrenal cortical capillary endothelial cells (ACE), bovine brain capillary endothelial cells (BBC), human umbilical vein endothelial cells (HUVEC), human dermal microvascular endothelial cells (HMVEC), adult bovine aortic endothelial cells (ABAE), bovine pericytes, human aortic vascular smooth muscle cells (HA-VSMC), baby hamster kidney fibroblasts (BHK-21) and human neonatal fibroblasts hFb. Cells were plated at a density of 4000 to 6000 cells/ml in 6 or 12 well dishes. At time of plating, no ligand, 5 ng/ml bFGF (GIBCO BRL), 5 ng/ml VEGF, or a range of EG-VEGF-Fc or -His tagged protein from 1 nM to 100 nM was added to the wells. Duplicate or triplicate samples were plated for each cell type. Confluence and morphology were monitored daily. At day 5 to 7 of the assay, cells were trypsinized in 0.01% trypsin (Gibco BRL) and cell number was assessed using a Coulter counter. Media and other cell culture reagents were obtained from Life Technologies, Inc. HUVEC, HMVEC and human keratinocytes were purchased from Clonetics. Bovine pericytes and human neonatal fibroblasts were a gift from M. Gerritsen. For the performance of assay see also Aravind and Koonin, *Curr. Biol.* 8:477-478 (1998).

Figure 12A:
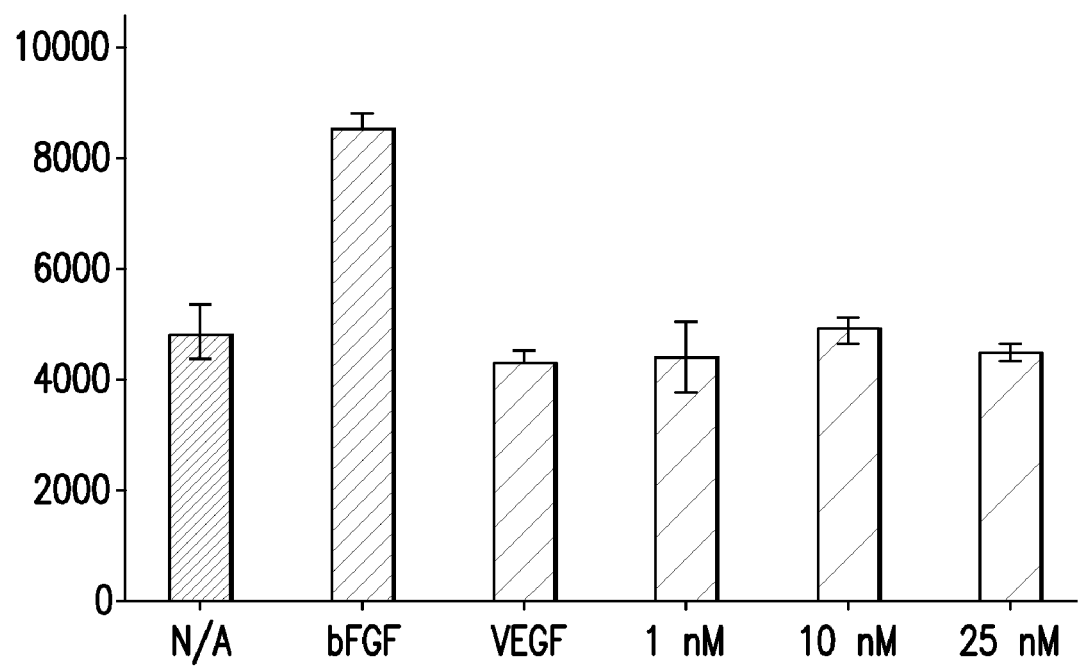
FIGS. 12A-E show bar graphs indicating relative proliferation of cells using either a control, bFGF, VEGF, or EG-VEGF in the concentration of 1 nM, 10 nM or 25 nM.
Figure 12B:
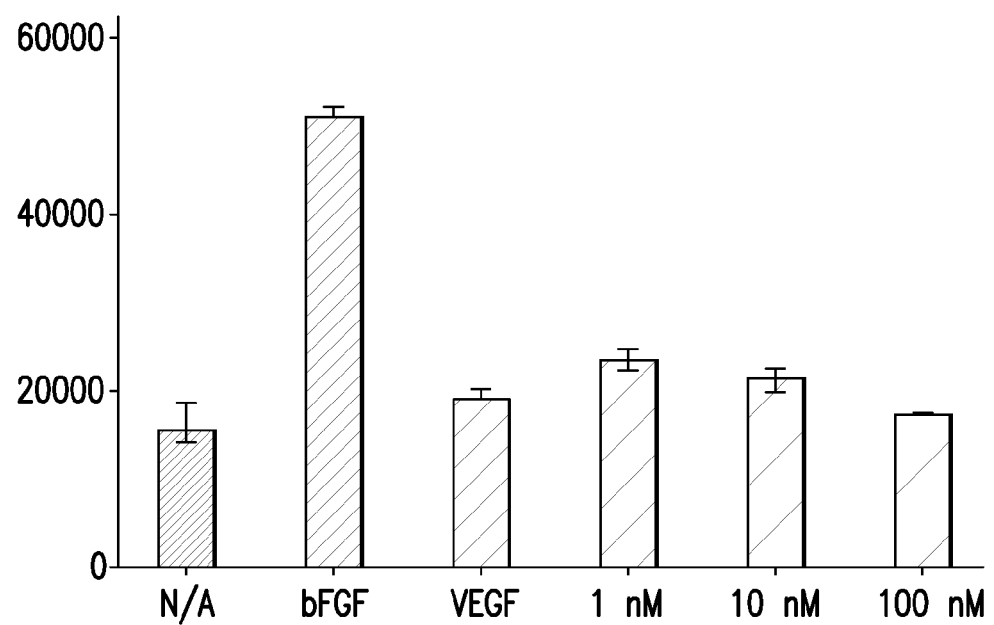
Figure 12C:
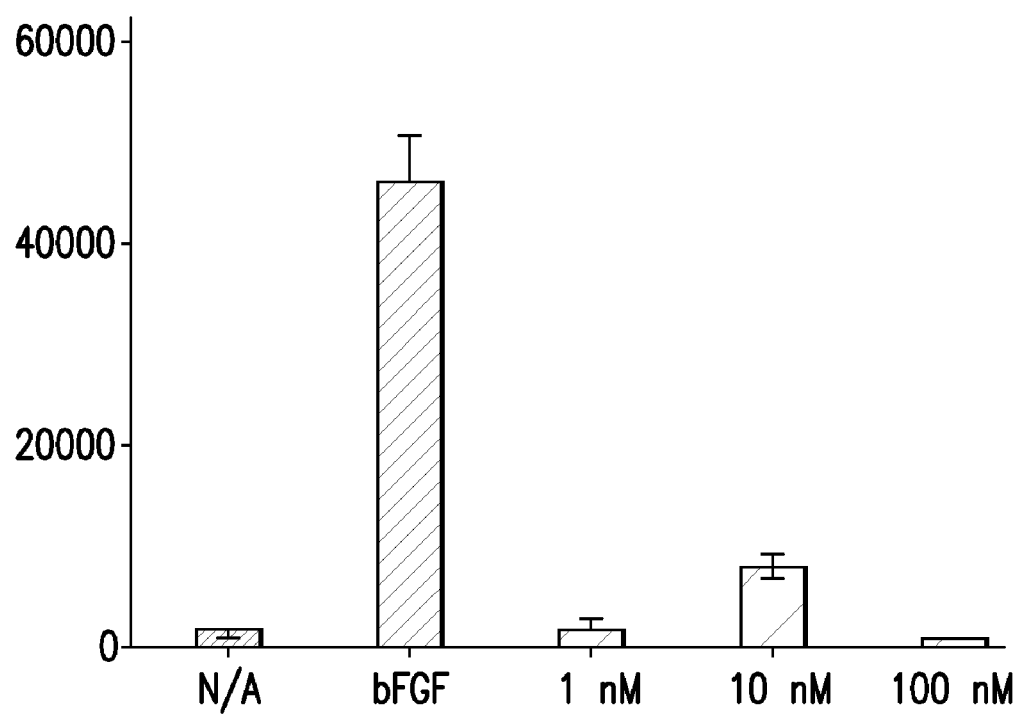
Figure 12D:
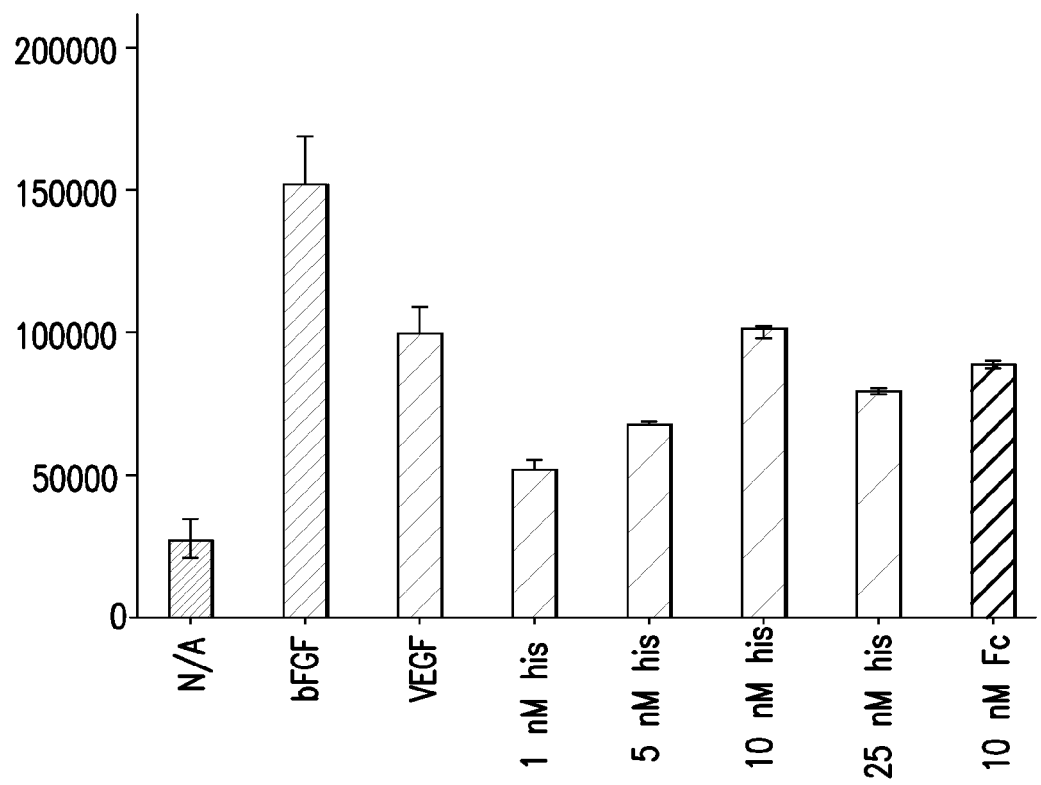
Figure 12E:
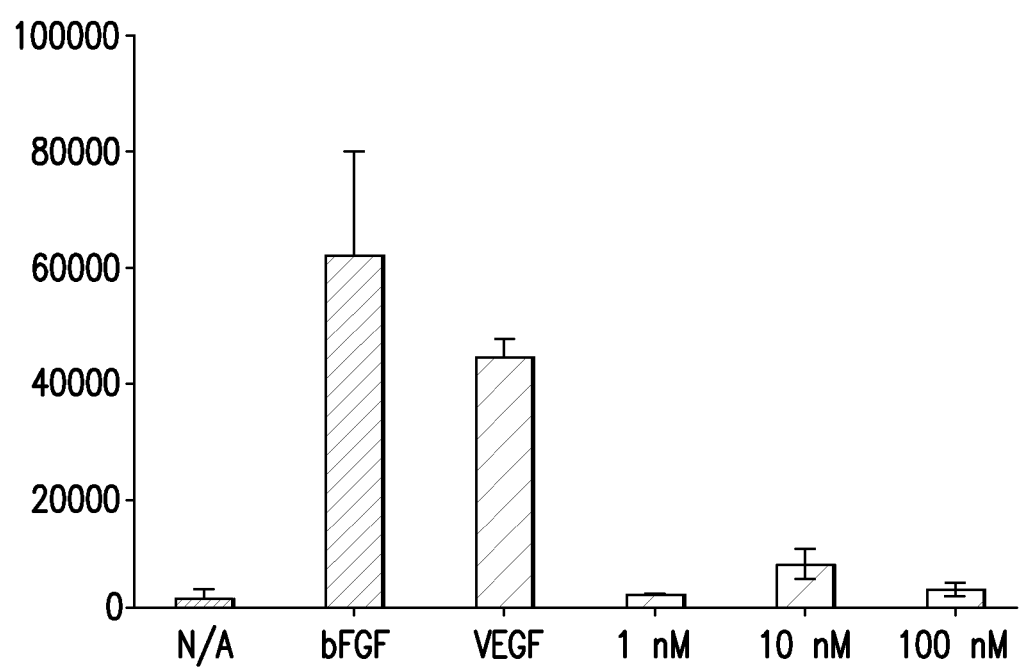

Several preliminary results are shown in FIG. 12A-E which indicate cells per well on the vertical axis. Each graph indicates relative proliferation of cells using either a control, bFGF, VEGF, or EG-VEGF in the concentration of 1 nM, 10 nM or 25 nM. FIG. 12A shows the results using pericytes. FIG. 12B shows the results using human aortic vascular smooth muscle cells (HA-VSMC). FIG. 12C shows the results using baby hamster kidney fibroblasts (BHK21). FIG. 12D shows the results using ACE. FIG. 12E shows the results using bovine brain capillary endothelial cells (BBC).

Similar results were obtained in the experiments the results of which are shown in FIG. 13. In these experiments, basal media served as a negative control (Ct) and bFGF (F) or VEGF (V) served as positive controls. EG-VEGF was tested at a range of concentrations. As illustrated in panel a, EG-VEGF stimulated proliferation of ACE cells with an $ED_{50}$ of 0.2 nM. A maximal effect was observed at approximately 2 nM. The fold increase in cell number was very similar to that induced by VEGF. The baculovirus-produced his- and Fc-tagged EG-VEGF proteins behaved very similarly in all experiments. Consistent with a mitogenic function, EG-VEGF induces in ACE cells a rapid and significant phosphorylation of the MAP kinases ERK1 and 2, as well as of other proliferation and survival signaling molecules. The mitogenic activity of EG-VEGF was not blocked by administration of a VEGF soluble receptor (mFlt-IgG) tested at a concentration range between 50 and 1000 ng/ml, indicating that such effect is not mediated by VEGF release. These findings clearly do not rule out the possibility of reciprocal inductive effects in more complex in vivo systems.

To determine the spectrum of cell types that proliferate in response to EG-VEGF, we tested a variety of other endothelial and non-endothelial cell types. The endothelial cell types tested include human umbilical vein (HUVEC), human dermal microvascular (HMVEC), bovine brain capillary (BBC), and adult bovine aortic (ABAE) endothelial cells.

As can be seen in FIG. 13, panel b, BBC cells showed only about 10% of the proliferative response seen with VEGF and the other endothelial cell types failed to show any effect following EG-VEGF administration, at all concentrations tested. Thus EG-VEGF is believed to be the first example of an endothelial cell mitogen that has such a restricted target cell specificity. Other endothelial cell mitogens such as VEGF and bFGF do not show any significant selectivity for various endothelial cell types [Leung et al., *Science,* 246:1306-1309 (1989)].

FIG. 13, panel c illustrates the finding that EG-VEGF did not elicit any proliferative response in cultures of vascular smooth muscle cells, pericytes, fibroblasts or keratinocytes. Thus, EG-VEGF is not only an endothelial-specific mitogen, but also one that acts selectively on a defined endothelial cell type.

In FIG. 13, panels b and c the proliferation index on the vertical axis is relative to the negative control, which is arbitrarily set at 1.

Example 15

Cell Migration (Chemotaxis) Assays

An essential aspect of the angiogenesis cascade is chemotaxis [Zetter, *Nature,* 285:41-43 (1980)]. VEGF or bFGF is able to act as a chemoattractant and stimulate endothelial cell migration. Assays for chemotactic activity (which will identify proteins that induce or prevent chemotaxis) have been previously described, see, for example, Current Protocols in Immunology, Ed by Coligan, Kruisbeek, Margulies, Shevach and Strober, Pub. Greene Publishing Associates and Wiley-Interscience, Chapter 6.12: 6.12.1-6.12:28; Taub et al., J. Clin. Invest. 95:1370-1376, 1995; Lind et al., APMIS 103: 140-146, 1995; Mueller et al., Eur. J. Immunol. 25:1744-1748; Gruber et al., J. Immunol. 152:5860-5867, 1994; Johnston et al., J. Immunol., 153:1762-1768, 1994. To define the biological activity of EG-VEGF, we assessed whether ACE cells and several other cell types display a chemotactic response to this molecule in a modified Boyden chamber assay.

Specifically, ACE cells, baboon adrenal endothelial cells (BAEC), MS-1 cells and HUVEC were used for migration assays. The MS-1 cell line was from the ATCC. Primary baboon endothelial cells were isolated from adrenal glands of premature or fetal baboons (gift of R. Clyman, UCSF). The tissue was dissociated essentially as described in Mesiano et al., J. Clin. Endocrinol. Metab. 76:968-976, 1993. Briefly, the capsule was removed and the remaining tissue was finely chopped into fragments of approximately 2 mm$^3$ in size with sterile razor blades. The fragments were subsequently incubated at 37° C. for 30-40 minutes in 0.1% collagenase (Sigma) in 50:50 Ham's F10:DMEM media, 10% FCS with the addition of DNase I (Life Technologies, Inc.). Single cell suspensions were washed, resuspended in PBS with 5% FCS, incubated with 1 µg of anti-KDR monoclonal antibody for $10^7$ cells, washed, and then incubated with goat anti-mouse antibody conjugated to fluoroscein isothiocyanate (Sigma). The KDR-positive versus negative populations were sorted using the EPICS ELITE cell sorter (Coulter Corporation). The endothelial cell population was maintained in CSC-medium containing 10% serum and growth factors (Cell Systems, Kirkland, Wash.). Falcon 8.0 µm filter inserts (Falcon 3097) were coated with 1% gelatin. Cells were cultured prior to assay as described above. Cells were trypsinized and transferred to EBM (Endothelial basal media, Clonetics) with 0.1% BSA for the assay. Cells were plated at $1-5 \times 10^4$ per upper chamber and growth factors were placed in the lower chamber. The assay was routinely a 16 hour assay at 37° C. At completion, cells were removed from the upper side of the membrane by scraping with a polyurethane swab and then the remaining cells on the bottom of the membrane were fixed with methanol. Cells were stained with propidium iodide and counted under low power using the Image-Pro program. The y-axis in FIGS. 14A, 14B and FIG. 13, panel d represents the migration index and is relative to the negative control, which is arbitrarily set at 1.

Figure 14A:
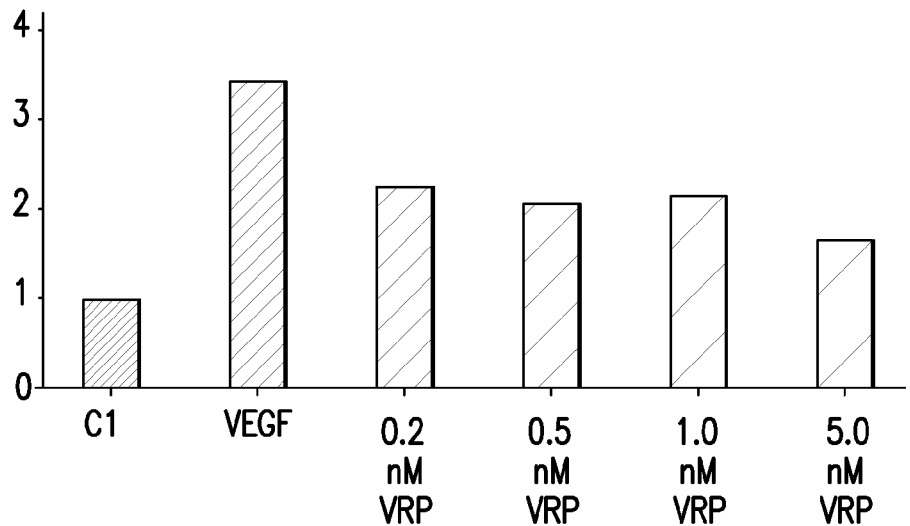
FIGS. 14A and 14B show relative endothelial cell migration in a control, with VEGF, or EG-VEGF in a concentration of 0.2 nM, 0.5 nM, 1 nM or 5 nM.
Figure 14B:
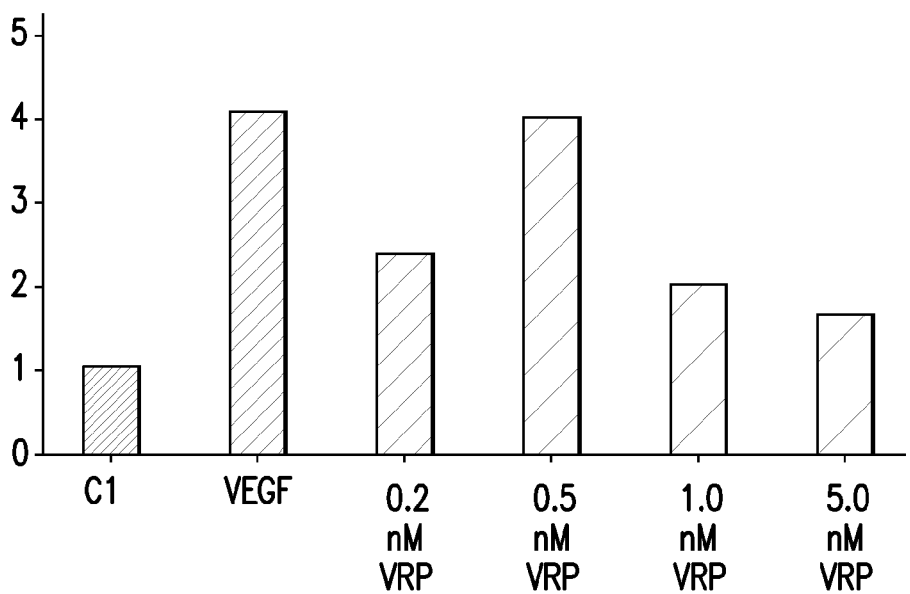

Preliminary results are shown in FIGS. 14A and 14B. Each graph shows relative endothelial cell migration in a control, in the presence of VEGF, or in the presence of EG-VEGF at a concentration of 0.2 nM, 0.5 nM, 1 nM or 5 nM. FIG. 14B shows the results using ACE.

These observations were reinforced by the results of further experiments shown in FIG. 13, panel d. A strong and reproducible chemotactic response was elicited in ACE cultures, with a peak response at 0.5 nM EG-VEGF. The magnitude of the effect was similar to that induced by VEGF. To extend our results to another primary cell type, we purified endothelial cells from baboon adrenal cortex (BAEC) by fluorescence-activated cell sorting, using a monoclonal antibody that recognizes the VEGF receptor-2, or KDR. In BAEC cultures, 0.5-5 nM EG-VEGF induced a chemotactic response of the same magnitude as that induced by VEGF. Furthermore, EG-VEGF induced migration in MS-1 endothelial cells to an even greater extent than VEGF. The MS-1 cell line, isolated from microvessels of murine endocrine pancreas, retains highly differentiated properties, such as VEGF receptor expression [Arbiser et al., *Proc. Natl. Acad. Sci. U.S.A.*, 94:861-866 (1997)]. However, no response was elicited from HUVEC, even though these cells displayed a strong response to the VEGF. Therefore, in addition to its mitogenic activity, EG-VEGF also acts as a chemoattractant, but only for a specific endothelial cell type.

These findings are in full agreement with the binding studies presented in Example 13, which revealed that iodinated EG-VEGF shows high-affinity, specific binding in ACE cells, that could be cross-linked to a membrane protein. However, no high affinity binding was detected in non-responsive cells such as HUVEC.

Example 16

Phosphorylation Analysis

Phosphorylation analysis was carried out according to methods known in the art. Briefly, adrenal cortex-derived capillary endothelial (ACE) cells were serum-deprived in 0.1% FCS for 14-16 hours, followed by an additional 90 minutes in 0.05% BSA. Cells were then treated with 2.5 mM VEGF (to induce maximal response) or 20 nM EG-VEGF and washed once in ice-cold PBS containing 0.1 mM sodium orthovanadate. Cells were lysed in 0.5 ml RIPA buffer containing 0.1 mM sodium orthovanadate, 5 mM para-nitrophenylphosphate, 10 mM sodium fluoride, 0.5 mM okadaic acid and a protease inhibitor cocktail (Roche MB 1836145). Anti-phospho ERK antiserum was purchased from Promega.

Figure 15:
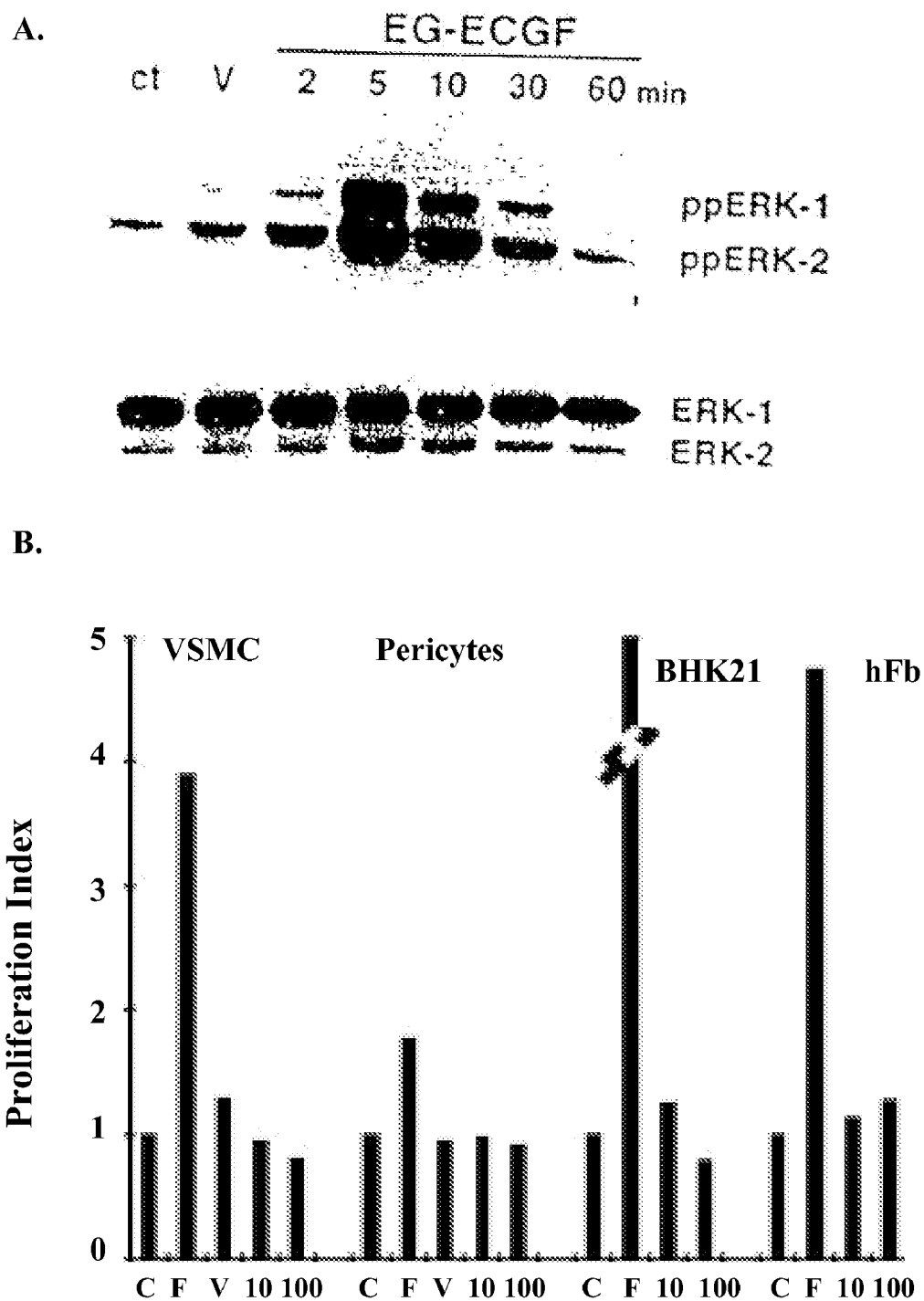
FIG. 15 shows the phosphorylation of the MAP kinases Erk1 and 2 after exposure to EG-VEGF.

Consistent with a mitogenic function, EG-VEGF induces in ACE cells a rapid and significant phosphorylation of the MAP kinases ERK1 and ERK2 (FIG. 15), as well as of other proliferation and survival signaling molecules (data not shown). Specifically, FIG. 15 shows that 20 nM EG-VEGF induced a significant and rapid phosphorylation of ERK1 and 2. No factor (ct) and VEGF (V) stimulation for 5 minutes served as controls and the time course for EG-VEGF stimulation is indicated above the lanes. Total ERK 1 and 2 levels are shown in the lower immunoblot. Further, the mitogenic activity of EG-VEGF was not blocked by administration of a VEGF soluble receptor (mFlt-IgG) tested at a concentration range between 50 and 1000 ng/ml, indicating that such effect is not mediated by VEGF release.

Example 17

Fenestration Assays

Endothelial cells within the adrenal cortex display a rather unique fenestrated phenotype found in restricted sites also including other endocrine glands, the choroid plexus, the gastrointestinal tract, and many tumors [Simionescu, supra]. Fenestrae are specialized plasma membrane microdomains or windows, approximately 60 nm in diameter, that are usually clustered [Palade et al., *Acta Physiol. Scand. Suppl.*, 463:11-32 (1979)]. The fenestrae are highly permeable to fluid and small solutes and are thought to facilitate large exchange of materials between interstitial fluid and plasma, such as that occurring in steroid-producing as well as other endocrine glands like pancreatic islets. We tested whether EG-VEGF could induce fenestrations in endothelial cells, alone or in combination with VEGF.

ECM was prepared according to a method known in the art, essentially as described in Gospodarowicz et al., J. Cell. Biol. 99:947-961, 1984. Briefly, corneal endothelial cells were isolated from steer eyes (Pel Freez, Ark.) and these were expanded in 50:50 Ham's F10:DMEM media supplemented with 15% FCS, penicillin/streptomycin, fungizone. To prepare the ECM-coated plates, $4 \times 10^4$ cells were plated per well in 6-well dishes and cultured for approximately 10 days in low glucose DMEM supplemented with 10% FCS, 2.5% dextran (Sigma 4133) and penicillin/streptomycin. At the end of 10 days, the cells were quickly lysed in 0.02 M $NH_4OH$ in water, rinsed several times with PBS and stored at 4° C. in PBS with antibiotics. ACE or MS-1 cells were plated at a density of $1\text{-}2 \times 10^5$ and grown to confluence. No addition, 2.5 nM VEGF, 10 nM EG-VEGF, or 2.5 nM VEGF plus 10 nM EG-VEGF were added to individual wells, in at least duplicate. The fenestration assays were replicated 3 times. Cells were rinsed with PBS and fixed for 2 hr in 2% formaldehyde, 2.5% glutaraldehyde in 0.1 M cacodylate buffer. After washing, the samples were post-fixed in aqueous 1% osmium for 2 hr, washed in water, dehydrated through graded ethanol and propylene oxide, and embedded in EPONATE 12 (Ted Pella, Inc., Redding Calif.). Ultrathin sections were cut on a Reichert Ultracut E microtome, counter-stained with uranyl acetate and lead citrate, examined in a Philips CM12 transmission electron microscope at 80 kV and images were captured with a GATAN Retractable Multiscan digital camera. At least 100 cell profiles were examined for each sample.

FIG. 13 shows representative electron micrographs from these experiments. Panel e shows untreated ACE cells. FIG. 13, panel f shows ACE cells treated with VEGF. FIG. 13, panel g shows ACE cells treated with EG-VEGF. Arrowheads indicate the location of fenestrae and magnification is indicated.

Notably, so far only VEGF has been reported to display the ability to induce fenestrations, in vivo and in vitro [Roberts and Palade, *Cancer Res.*, 57:765-772 (1997); Esser et al., *J. Cell. Biol.*, 140:947-959 (1998)] ACE or MS-1 cells were grown to confluence on extracellular matrix produced by bovine corneal endothelial cells and then treated with ligand for 24-72 hours. In agreement with previous studies [Esser et al., supra], VEGF induced fenestrations in 4.33±1.53% of ACE cell profiles (FIG. 13, panel f). The MS-1 cultures acquired a similar number of fenestrations in response to VEGF (not shown). The effect of EG-VEGF was very similar to that of VEGF, in both cell types (FIG. 13, panel g for ACE).

A combination of the two factors produced an additive or co-operative response, inducing fenestrae in 11±1% of the ACE cell profiles. No fenestrations were observed in the absence of VEGF or EG-VEGF. This finding supports the hypothesis that these factors may cooperate in vivo, in settings such as the adrenal cortex or the ovary, to induce the fenestrated phenotype of the resident endothelial cells.

Example 18

Hypoxic Regulation of EG-VEGF

A. Taqman Analysis of EG-VEGF Expression

Hypoxia is a key inducer of angiogenesis in both physiological and pathological conditions. By virtue of activating hypoxia-inducible factor (HIF)1, low oxygen tension is known to induce expression of VEGF, in addition to erythropoietin (Epo) and certain glycolytic enzymes, through cis-acting regulatory elements Semenza, *J. Appl. Physiol.* 88:1474-1480 (2000). Therefore, we sought to determine whether hypoxia regulates EG-VEGF mRNA expression in endothelial cells.

For expression analysis, RNA isolates from replicate, matched samples of normoxic-treated versus hypoxia-exposed SW13 and H295R cells (both from the ATCC) were prepared using the Rneasy kit (Qiagen) as described by the manufacturer. For real-time quantitative RT-PCR, 50 ng of total RNA was assayed in triplicate with the Perkin Elmer Taqman kit reagents and an ABI prism 7700 Sequence Detector. Oligos and probes used are as follows:

```
                                          (SEQ ID NO: 9)
forward EG-VEGF PCR primer
5'-CCGGCAGCCACAAGGTC-3'

(SEQ ID NO: 10)
reverse EG-VEGF PCR primer
5'-TGGGCAAGCAAGGACAGG-3'

(SEQ ID NO: 11)
EG-VEGF probe
5'-CCTTCTTCAGGAAACGCAAGCACCAC-3'

(SEQ ID NO: 12)
forward VEGF PCR primer
5'-AATGACGAGGGCCTGGAGT-3'

(SEQ ID NO: 13)
reverse VEGF PCR primer
5'-TTGATCCGcATAATCTGCATG-3'

(SEQ ID NO: 14)
VEGF probe
5'-TGTGCCCACTGAGGAGTCCAACATCA-3'
```

As a negative control, expression analysis of β-actin was similarly performed as described above with primers and probe supplied by the manufacturer (Perkin-Elmer).

FIG. 17A, panel a illustrates the finding that exposure of the human adrenal carcinoma cell lines SW13 and H295R to hypoxic conditions (~2% oxygen) resulted in a 275±15% and 210±12% increase in EG-VEGF mRNA levels above normoxia, respectively, while the VEGF mRNA increased 352±30% and 266±14%, respectively. A search of the EG-VEGF promoter sequence for the core HIF-1 binding site revealed a putative element within the first 2450 nucleotides of the transcription start site, based on a consensus sequence (5'TACGTGCGGC-3', bolded text represents invariable sequence).

B. HRE Luciferase Activity Analysis

To determine whether the hypoxic regulation of the EG-VEGF gene was mediated by HIF-1, expression of a luciferase reporter gene under the control of the putative EG-VEGF element was analyzed. The luciferase reporter constructs were generated by cloning compatible, annealed oligos into the BglII site of the pGL3-Promoter vector (Promega):

```
                                          (SEQ ID NO: 15)
HRE_consensus(Epo) sense
5'-AGGCCCTACGTGCGGCCTCACACAGCCTGTTCTGA-3'

(SEQ ID NO: 16)
HRE_mutant(Epo) sense
5'-AGGCCCTAATTGCGGCCTCACACAGCCTGTTCTGA-3'

(SEQ ID NO: 17)
HRE_EG-VEGF' sense
5'-GCTAAGGACGTGCTATTCATGGGGTGCAGGAAGAT-3'

(SEQ ID NO: 18)
HRE_EG-VEGF mutant sense
5'-GCTAAGGAATTGCTATTCATGGGGTGCAGGAAGAT-3'
```

Transient transfections of the luciferase reporter constructs into HeLa cells were performed in 6-well dishes using Effectene transfection reagent (Qiagen). For each well, 0.75 μg of reporter along with 0.25 μg of pRL-SV40 control vector was transfected. Triplicate, paired transfections were used in parallel normoxic versus hypoxic incubations, dishes being exposed to hypoxia for 18-24 hours commencing 24 hours after transfection. Cells were lysed and assayed using the dual-luciferase reporter assay system (Promega). Luciferase activity is normalized to control vector values, and a representative experiment is shown in FIG. 17B error bars representing standard deviation.

Figure 17:
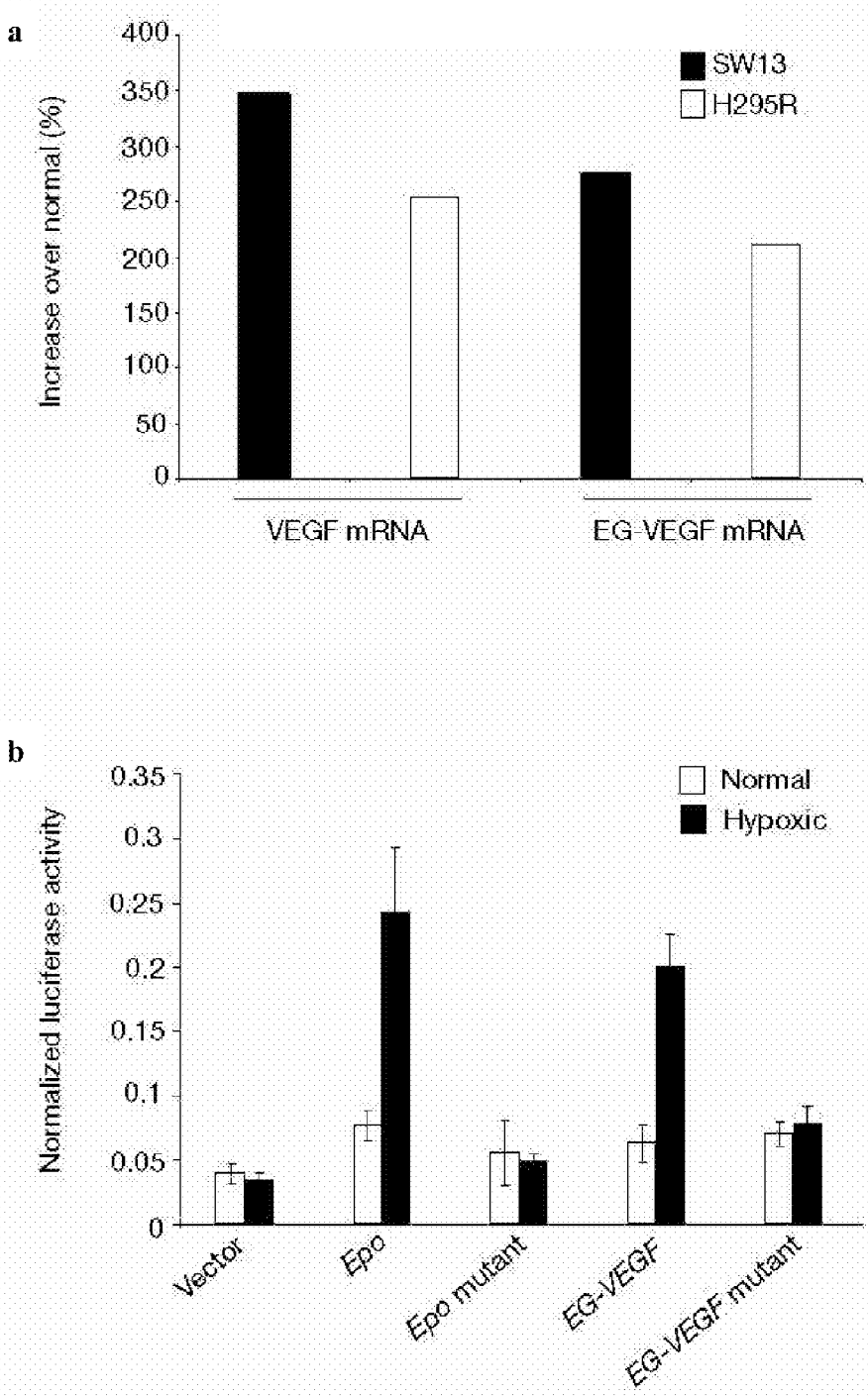
FIGS. 17A-B illustrate hypoxic-regulation of EG-VEGF.

Following an 18-24 hour incubation in hypoxic conditions, a luciferase reporter construct containing the putative EG-VEGF element conferred a 3.3±0.8-fold increase above normoxic conditions. This level is comparable to that conferred by the hypoxia-response element (HRE) Epo consensus, 3.4±1.2-fold (FIG. 17, panel b). Mutating the core sequence of either consensus or the putative EG-VEGF HRE abolished the response to hypoxia, verifying the specificity of the response. While we cannot rule out additional mechanisms, these findings indicate that in all likelihood HIF-1 is a key mediator of the hypoxic regulation of the EG-VEGF gene.

Thus, it is striking that in spite of the lack of sequence homology, the EG-VEGF and VEGF genes, not only have similar effects in responsive endothelial cells, for example hypoxia-inducible expression, but may also be regulated through common mechanisms.

Example 19

Heparin Binding Assay

Angiogenic factors, including bFGF and VEGF, interact with extracellular matrix components, such as heparin sulfate proteoglycans. The interaction between angiogenic factors with extracellular matrix components is suggested to regulate the bioavailability and activity of these molecules (Klagsburn, *Semin Cancer Biol.* 3:81-7 (1992)). Thus, we tested whether EG-VEGF binds to heparin.

15 μg of untagged protein was applied to a Hi-Trap heparin-sepharose column (Pharmacia) in 10 mM Tris, pH 7.4, 0.1 M NaCl. The column was eluted with a linear gradient of NaCl (0.1-2.0 M). Human VEGF$_{165}$ was used as a reference.

When applied to a heparin sepharose column, EG-VEGF eluted in the presence of ~0.5M NaCl, while VEGF$_{165}$ eluted at ~0.7 M NaCl under the same chromatographic conditions. This finding indicates that EG-VEGF is a heparin-binding growth factor which may be sequestered in the extracellular compartment in vivo.

Example 20

Selectivity of In Vivo Angiogenic Effects

A. Rat Corneal Pocket Angiogenesis Assay

The in vivo activity of EG-VEGF was examined an adult rat corneal pocket assay, as previously described (Gille et al., J. Biol. Chem. 276:3222-3230 (2001)). Hydron coated pellets containing, 200 ng VEGF$_{165}$ or 500 ng EG-VEGF, plus methylcellulose and aluminum sucralfate were inserted into the base of the cornea pocket (n=6). Control pellets contained 500 ng CD4-IgG. At day 6, animals were euthanized and injected with high molecular weight FITC-dextran to allow for visualization of the vasculature. Measurements of neovascular areas in corneal whole mounts were performed using computer-assisted image analysis (Image-Pro Plus).

Figure 19:
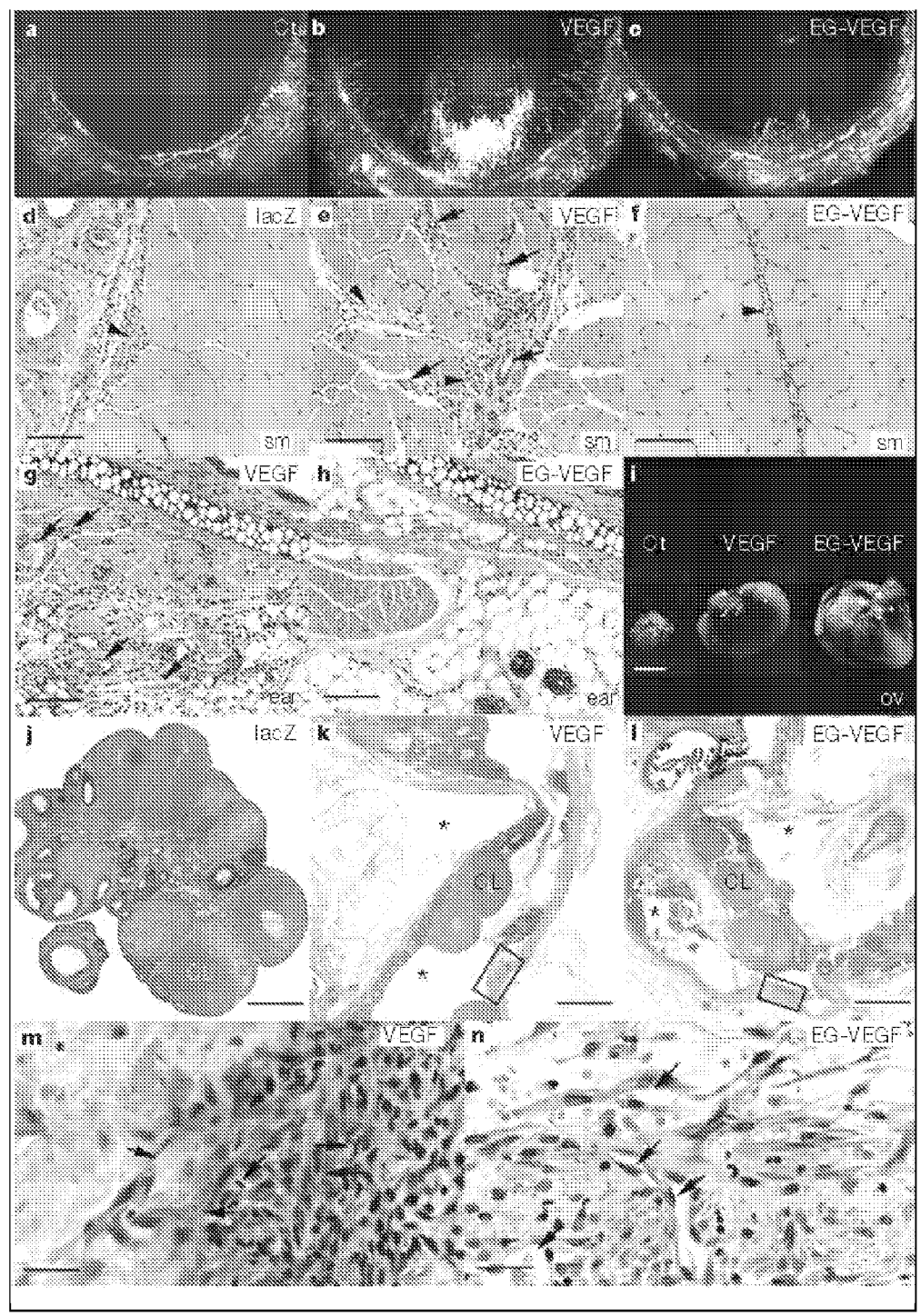
FIG. 19 illustrates the selectivity of in vivo angiogenic effects of EG-VEGF. Panels a-c show the results of a rat corneal pocket assay. Note the strong angiogenic response induced by VEGF protein, while EG-VEGF has essentially no effect. Panels d-f show the results obtained by injecting adCMV-lacZ, AdCMV-VEGF$_{164}$, or AdCMV-EG-VEGF ($5 \times 10^8$ pfu) in the skeletal muscle (sm) of nude rats. Arrowheads point to microspheres marking the injection site, arrows point to new blood vessels. Note the angiogenic response, with abundant new vessel formation, induced by VEGF, while both lacZ and EG-VEGF Av had no appreciable effects. Panels g-h show the results of VEGF and EG-VEGF Av injection in the mouse ear. Again, VEGF Av resulted in a strong angiogenic response, which was absent in the animals injected with EG-VEGF Av (scale bar in d-h=100 μm). Panel i shows the gross appearance of ovaries (ov) following injection of LacZ (ct) VEGF or EG-VEGF Av, after seven days (scale bar=0.5 cm). Note the much larger mass plus the presence superficial vessels and hemorrhagic areas in both VEGF and EG-VEGF groups. Panels j-n are micrographs of ovaries injected with Av vectors ($5 \times 10^8$ pfu), as indicated. Note the normal architecture and morphology of the lacZ ovary in j. Corpora lutea (CL) are indicated. In contrast, the VEGF (k) and EG-VEGF (l) groups revealed very similar changes, with large fluid-filled or hemorrhagic cystic areas (*) (scale bar in j-l=1 mm). Panels m-n are high power micrographs (scale bar=33 μm) of boxed areas in k and l, respectively. Areas of intense angiogenesis are evident at the periphery of cystic lesions. Arrows point toward blood vessels.

In the rat corneal assay, purified EG-VEGF failed to show a significant response in all eyes tested, whereas VEGF induced the expected angiogenic effects (FIG. 19, panels a-c). Similar results are observed with the rabbit cornea. Note the strong angiogenic response induced by VEGF protein, while EG-VEGF has essentially no effect.

B. Angiogenic Effects of Site-Directed Adenoviral Injections of EG-VEGF

To further study the in vivo activity of EG-VEGF, the effects of EG-VEGF delivery in a local and sustained fashion was examined. To achieve EG-VEGF delivery in a local and sustained fashion, adenovirus (Av) vectors were generated and injected into various sites in athymic nude rats or mice. Recombinant Av vectors expressing lacZ or VEGF served as controls.

Athymic nude rats were anesthetized using isofluorane, and a 2-2.5 cm incision was made on the left dorsal area. The ovary was lifted and secured using nontraumatic forceps. Doses of $10^8$ or $5 \times 10^8$ pfu in 5-10 μl of saline were injected via a gas-tight Hamilton syringe fitted with a 31 G needle (Hamilton). All work was performed in a biosafety cabinet with BSL2 practices in place. For skeletal muscle (left gastrocnemius) or subcutaneous ear injections, athymic nude mice or rats were anesthetized with isofluorane, the area was cleaned, and doses of $5 \times 10^8$ pfu of each virus preparation in a 50 μl volume was injected per site. Animals in all Av studies were euthanized one week after Av administration. At necropsy, tissues were dissected and frozen or fixed for histological analysis.

When injected in the skeletal muscle of nude rats, the effects of lacZ and EG-VEGF Av were essentially indistinguishable, with minimal inflammatory infiltrate and absence of angiogenesis, and with abundant mitotic endothelial cells, edema and granulation tissue (FIG. 19, panels d-f). Very similar results were obtained following injection of the same Av vectors in the mouse ear (FIG. 19, panels g and h). Again, VEGF Av resulted in a strong angiogenic response, which was absent in the animals injected with EG-VEGF Av. However, intra-ovarian delivery of either EG-VEGF or VEGF Av resulted within a week in a dramatic enlargement of the injected ovaries, with grossly visible blood vessels as well as hemorrhagic areas (FIG. 19, panel i) The ovarian wet weights in a representative experiment in nude rats were 33±3 mg in the LacZ group, 489±30 mg in the EG-VEGF group and 191±91 mg in the VEGF group (n=4). The weight of noninjected ovaries (37±7 mg) was not different from the LacZ group. Although there was a trend toward larger mass in the EG-VEGF, compared to the VEGF group, the histological picture was very similar. In both cases, large fluid- or blood-filled cystic areas that disrupted the ovarian architecture were present (FIG. 19, panels j-n). High power examination revealed intense angiogenesis at the periphery of the cysts (FIG. 19, panels m-n). The morphology of the LacZ ovaries was normal. Thus, VEGF and EG-VEGF are able to trigger the same chain of events in a responsive tissue, including the ability to induce fluid extravasation, in addition to angiogenesis.

Example 21

Anti-EG-VEGF Antibodies with Neutralizing Activity

Seven monoclonal antibodies were generated that recognize EG-VEGF. BALB/c mice were immunized by footpad injection with 3 μg of EG-VEGF conjugated to a his tag and emulsified in MPL/TDM/CWS adjuvant. Animals were boosted bi-weekly with the same amount of protein, for a total of 8 injections. Five days after the final boost, cells from popliteal nodes were fused with X63-Ag8-653 myeloma cells (American Type Culture Collection (ATCC)). Hybridoma supernatants were screened for anti-EG-VEGF activity by standard ELISA. Briefly, 96 well tissue culture plates (Nunc Maxisorb) were coated with antigen by adding 100 μl/well of a solution containing EG-VEGF-his antigen at 1 μg/ml in 50 mM carbonate buffer (A3004) and incubating overnight at 2-8° C. Wells were washed 3 times in wash buffer (PBS/ 0.05% T20/20× stock Hyclone SH3649-01) and blotted dry. Following the wash, wells were blocked with ELISA Assay Buffer, 200 μl/well, by shaking at room temperature for approximately 1 hour. Wells were washed again three times with wash buffer and blotted dry. Samples and controls were added to individual wells (100 μl/well) and incubated for approximately 1 hour at room temperature. Following a third wash, goat anti-mouse IgG (Fc Specific)/HRP (Sigma A0168) was added, 100 μ/well, and incubated for approximately 1 hour with shaking. After washing three times and blotting dry, 100 μl substrate (1 5 mg OPD tablet (Sigma P6912) dissolved in 12.5 ml $H_2O_2$) was added to each well. Reactions were stopped with the addition of 100 μl 2.5 $NH_2SO_4$. Plates were read using 405 nm (reference) and 490 nm (absorbance). Positive cell lines were further subcloned twice to ensure that single cell colonies were obtained.

Antibodies were isotyped using GibcoBRL Mouse Monoclonal Antibody Isotyping Kit (Dipstick Format) essentially according to manufacturers directions. All of the monoclonal antibodies were found to be IgG1.

The antibodies were further tested for their ability to neutralize EG-VEGF activity in cell-based proliferation assays. The proliferation assay were carried out essentially as described above. Briefly, approximately 6,000 adrenal cortical capillary endothelial (ACE) cells were plated in each well of 12-well plates. Cells incubated in basic media (low glucose DMEM supplemented with 10% FCS) were used as a negative control, while cells incubated with 5 ng/ml VEGF were used as a positive control for proliferation. 10 nM EG-VEGF was added to the remaining wells, either alone or in combination with 1, 10, 25 or 50 μg/ml of each of the seven antibodies. In addition, combinations of two of the antibodies were tested at a concentration of 25 μg/ml of each antibody. All experiments were performed in duplicate.

Figure 21:
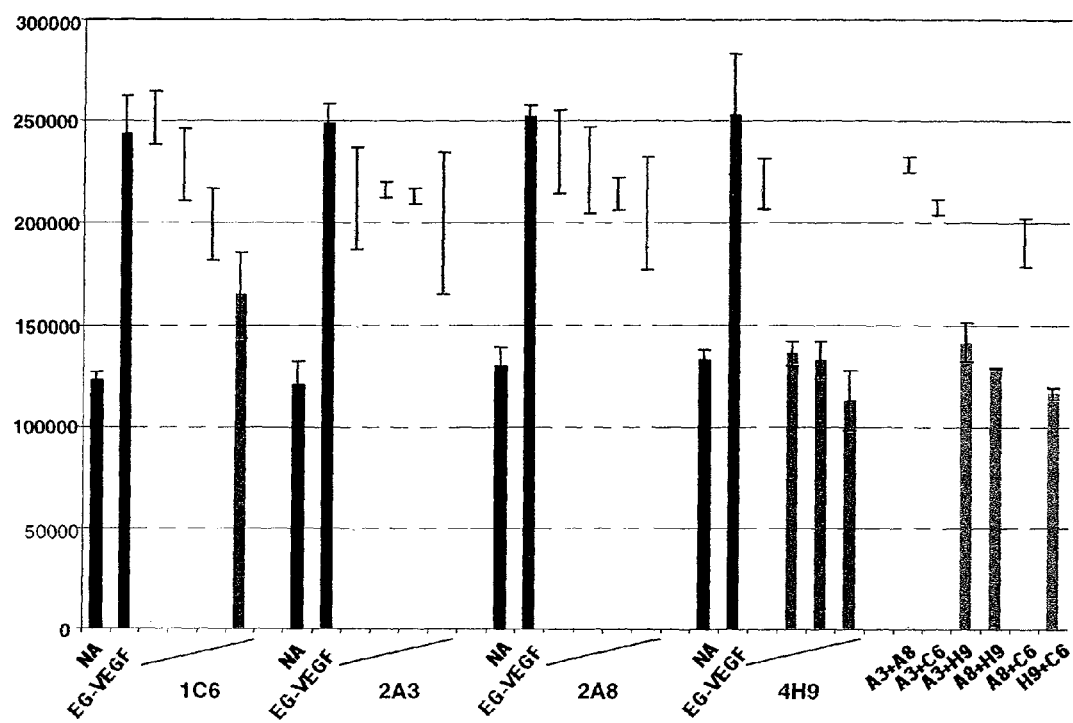
FIG. 21 shows the effect of increasing concentrations of monoclonal antibodies 1C6, 2A3, 2A8 and 4H9, as well as combinations of these antibodies, on the proliferative effect of EG-VEGF.

As shown in FIG. 21, four antibodies were found to neutralize EG-VEGF activity. These were antibodies 1C6, 2A3, 2A8 and 4H9. In particular, monoclonal antibody 4H9 was found to completely neutralize the activity of 10 nM EG-VEGF when added at a dose of 10 µg/ml or higher.

Example 22

EG-VEGF Induces P44/42 MAPK (ERK1/2) Phosphorylation

Figure 22:
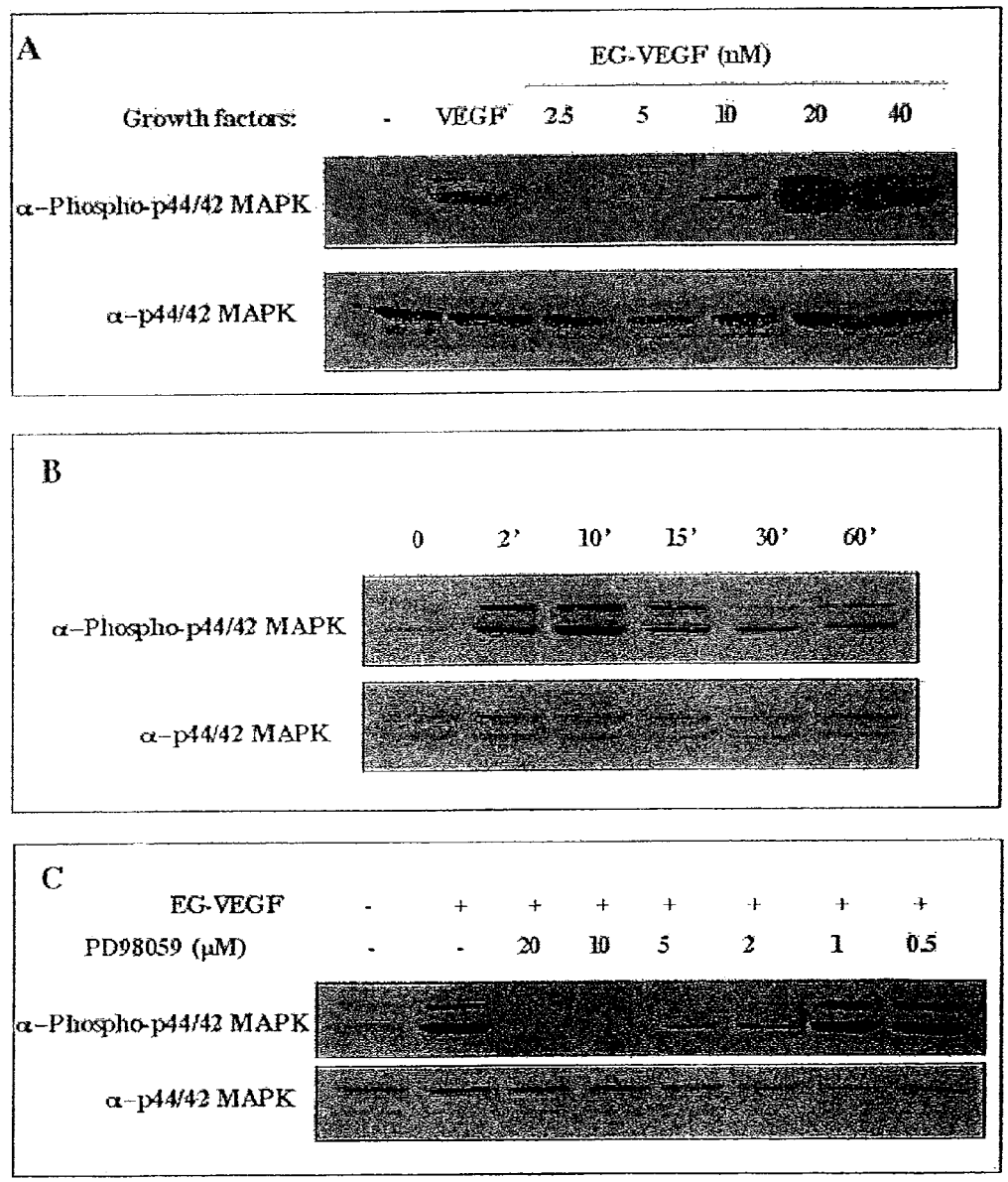
FIGS. 22A-C illustrate the activation of MAPK pathway in ACE cells by EG-VEGF.

The ability of EG-VEGF to stimulate p44/42 MAPK (ERK 1/2) phosphorylation was investigated. Briefly, after exposure to various concentrations of EG-VEGF for 10 minutes, cell lysates were electrophoresed on SDS polyacrylamide gels, transferred to PVDF membrane and blotted with phospho-p44/42 MAPK antibody (Cell Signaling, Inc.), which only detects p42 and p44 MAPK when catalytically activated by phosphorylation at Thr202/Tyr204 (FIG. 22A). A dose dependent phosphorylation of p44/42 MAPK was observed in response to EG-VEGF, with a maximal response at 20 nM EG-VEGF.

The time course of EG-VEGF stimulated p44/42 MAPK phosphorylation was also investigated (FIG. 22B). Rapid phosphorylation was found to begin 2 minutes after addition of EG-VEGF and peaked at 10 minutes. After 30 minutes the MAPK phosphorylation decreased to a slower, stable level, but remained above non-stimulated background phosphorylation.

The specificity of the MAPK pathway activated by EG-VEGF was investigated by observing the effect of the MEK1 specific inhibitor PD98059 (Biomol. Inc.) on EG-VEGF induced phosphorylation of p44/42 MAPK. Pre-treatment of ACE cells with PD98059 blocked EG-VEGF-induced phosphorylation in a dose dependent manner, as shown in FIG. 22C. Phosphorylation of p44/42 MAPK was completely inhibited at a PD98059 concentration of 10 µM.

Example 23

EG-VEGF-Induced Activation of MAPK does not Require VEGF

Figure 23:
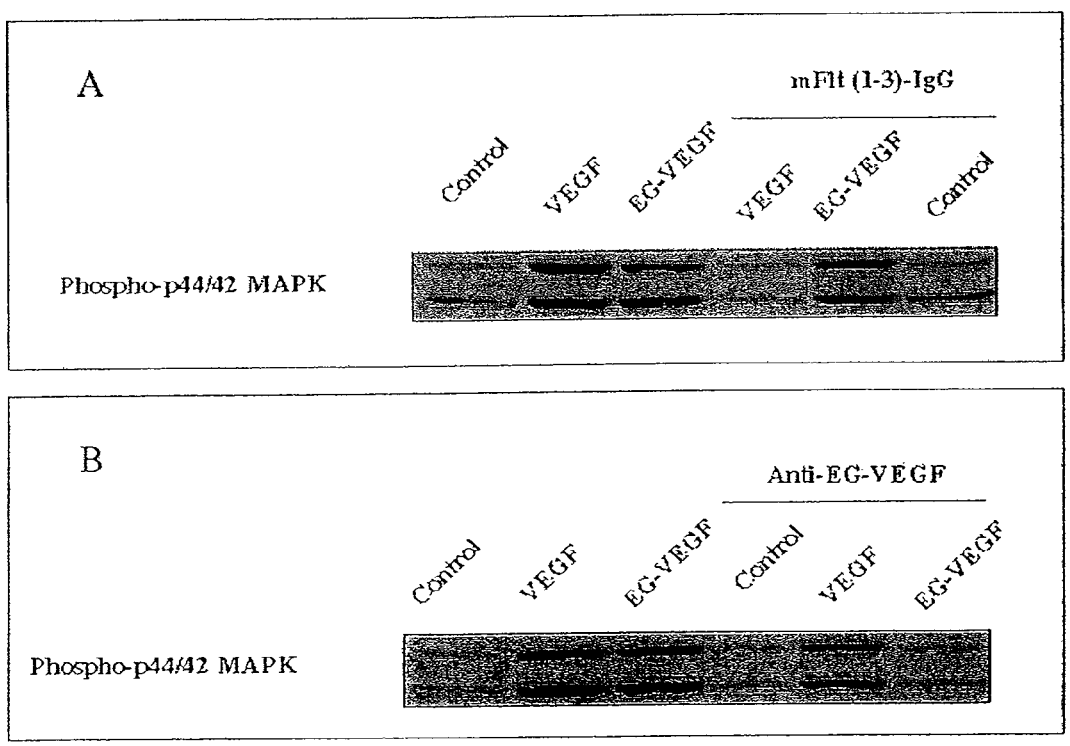
FIGS. 23A-B show that EG-VEGF-induced p44/42 MAPK activation is not dependent on VEGF. Subconfluent ACE cells were serum-starved overnight and pre-treated with 4 μg/ml (A) mFlt (1-3) IgG, or (B) monoclonal antibody against EG-VEGF (clone 4H9) for 2 hours, followed by stimulation with 0.5 nM VEGF or 20 nM EG-VEGF for 10 minutes. Cells were lysed and analyzed by western blot.

VEGF and EG-VEGF were found to have a similar ability to induce p44/42 MAPK phosphorylation. Thus the possibility that EG-VEGF downstream signaling is mediated by VEGF release was investigated. The effect of specific antibodies on p44/42 MAPK phosphorylation by VEGF and EG-VEGF was compared. As can be seen in FIG. 23A, a soluble VEGF receptor, mFlt (1-3) IgG, completely inhibited VEGF-induced p44/42 MAPK phosphorylation, while a neutralizing monoclonal antibody directed against EG-VEGF blocked EG-VEGF phosphorylation (FIG. 23B). However, mFlt (1-3) IgG had no effect on EG-VEGF-induced activation (FIG. 23A) and the anti-EG-VEGF antibody did not block VEGF-induced stimulation (FIG. 23B). Thus EG-VEGF and VEGF activate the p44/42 MAPK pathway independently.

Example 24

EG-VEGF-Induced Activation of MAPK is PTX-Sensitive

The effect of pertussis toxin (PTX; Biomol. Inc.) on EG-VEGF induced MAPK activation was investigated (FIG. 24A). PTX specifically modifies the heterotrimeric G protein Gαi, thus blocking the signaling pathways of G protein coupled receptors involving Gαi. Thus, the effect of PTX on lysophosphatic acid (LPA) stimulation was used as a positive control, as its receptor is coupled to Gαi. Pretreatment of ACE cells with 200 ng/ml PTX abolished LAP induced p42/44 MAPK phosphorylation (FIG. 24A). In contrast, PTX had essentially no effect on VEGF stimulated MAPK phosphorylation. However, PTX nearly abolished EG-VEGF-induced phosphorylation of MAPK, suggesting that the EG-VEGF receptor is a G-protein coupled receptor.

The tyrosine phosphorylation of ACE cell membrane proteins following stimulation with VEGF or EG-VEGF was also observed. Briefly, ACE cell lysates were incubated with 50 ml of wheat germ agglutinin beads (WGA; Pharmacia) for 2 hours at 4° C. The lectin complex was washed with lysis buffer three times and boiled with SDS sample buffer, followed by electrophoresis, transfer and blotting with phopho-tyrosine antibody 4G10 (Upstate Inc.). Phospho-tyrosine blots of WGA precipitates show that, while VEGF induced tyrosine phosphorylation of a 200 kD band, there was no evidence of tyrosine phosphorylation in response to EG-VEGF (FIG. 24B). Thus EG-VEGF and VEGF may utilize receptors with different mechanisms to activate downstream signaling.

Example 25

EG-VEGF Induces Akt Phosphorylation

Figure 25:
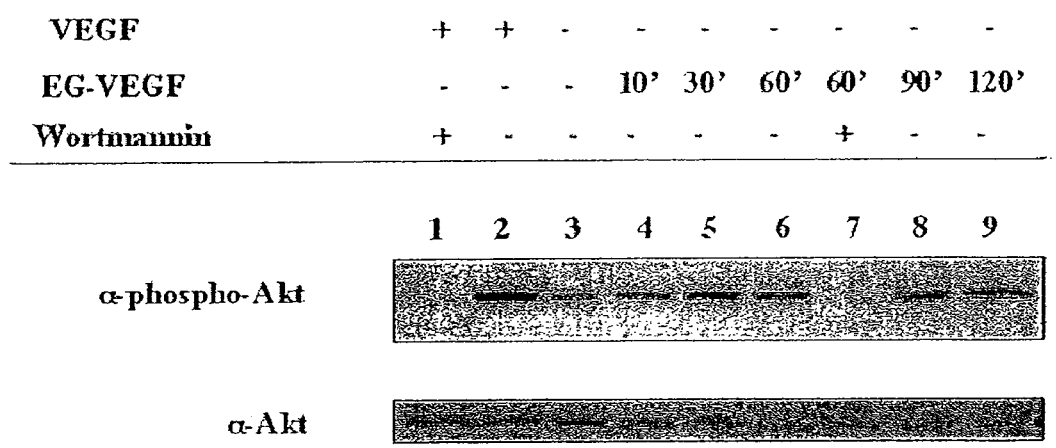
FIG. 25 demonstrates that EG-VEGF induces Akt phosphorylation in a PI 3-kinase dependent manner. Subconfluent ACE cells were serum starved overnight and pre-treated with 300 nM wortmannin for 30 minutes (lanes 1 and 7), followed by stimulation with VEGF (lanes 1 and 2) or EG-VEGF (lanes 4 and 9) for the indicated time. Cell lysates were electrophoresed, transferred and blotted with anti-phospho-Akt (upper panel) and anti-Akt (lower panel).

FIG. 25 shows a time course of EG-VEGF stimulated phosphorylation of Akt at Ser473. ACE cells were stimulated with EG-VEGF or VEGF for the indicated time, with or without pretreatment with 300 nM wortmannin (Calbiochem). Cell lysates were electrophoresed, transferred and blotted with an anti-phospho-Akt (Ser 473) antibody (Cell Signaling, Inc.). EG-VEGF induced a prolonged increase of phospho-Akt from 10 to 120 minutes. The activation peaked at 20 minutes and was sensitive to the PI 3-kinase inhibitor wortmannin, as can be seen in lane 7 of FIG. 25. In contrast, the effect of VEGF on Akt phosphorylation was acute, peaked at 10-30 minutes and subsided after 60 minutes (data not shown). Thus, EG-VEGF treatment produces PI 3-kinase dependent activation of Akt in ACE cells.

Example 26

EG-VEGF is a Potent Survival Factor for Epithelial Cells

Figure 26:
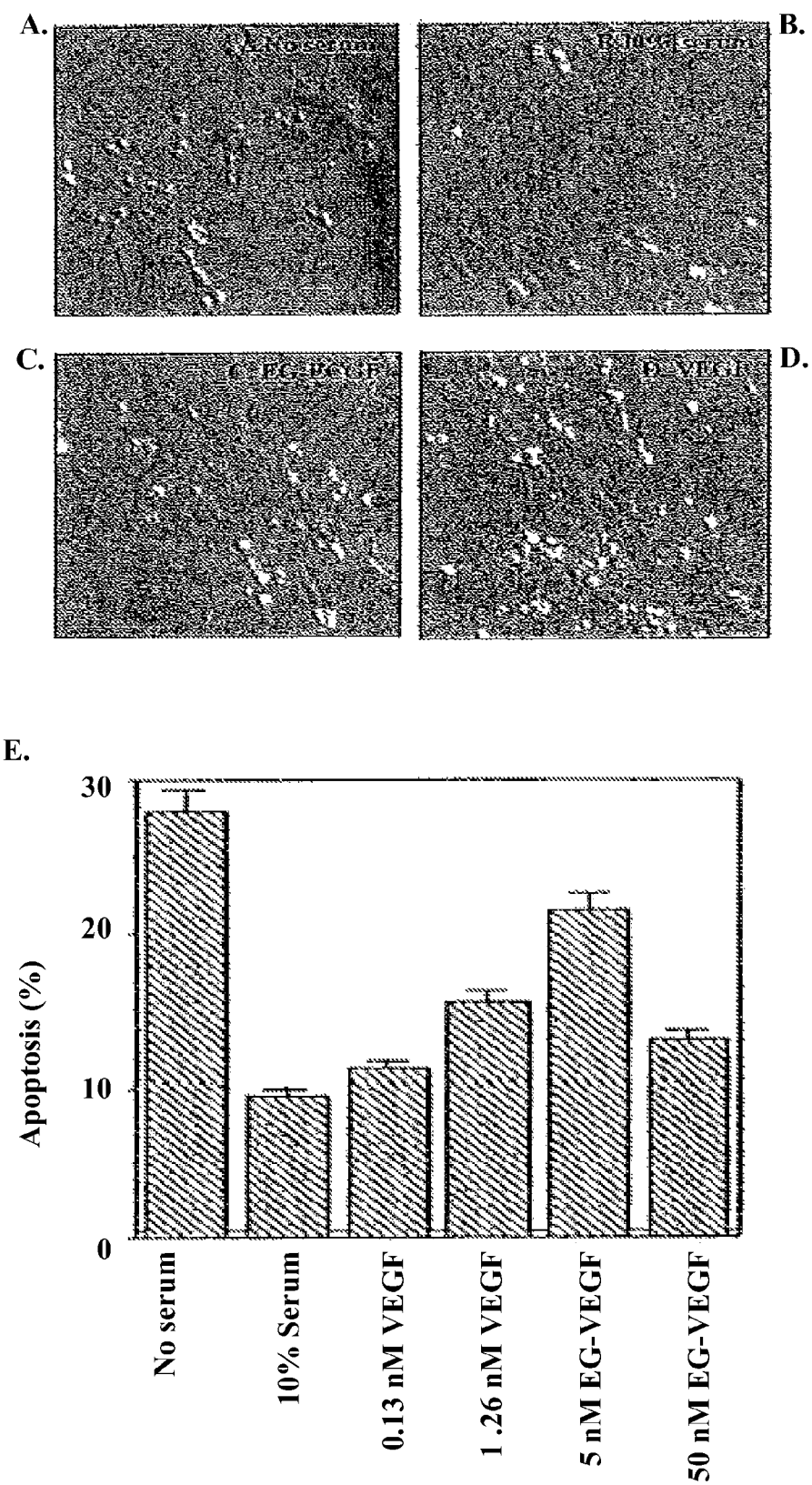
FIG. 26A-E illustrate that EG-VEGF protects ACE cells from serum starvation-induced apoptosis. Approximately $3 \times 10^5$ ACE cells were cultured in complete medium overnight, then switched to serum free medium for 24 hours in the presence or absence of VEGF or EG-VEGF. ACE cells were trypsinized and stained with propidium iodide and annexin-FITC. The apoptotic cells were quantitated by fluorescence-activated cell sorting (FACS) analysis. The morphology of ACE cells can be seen after serum starvation for 24 hours (A), in the presence of 10% calf serum (B), in the presence of 50 nM EG-VEGF and no serum (C), and in the presence of 1.25 nM VEGF but no serum (D). Quatitation of apoptotic cells by FACS analysis is presented in E.

As Akt activation has been implicated in cell survival, the ability of EG-VEGF to promote ACE cell survival in serum-starved conditions was evaluated (FIG. 26). Briefly, $3 \times 10^5$ ACE cells were cultured in 6 well plates in complete medium for 24 hours. Cells were washed twice with PBS and 2 ml of CS-C serum free medium (Cell System) was added, along with various concentrations of growth factor, and incubated for 24 hours. Cells were harvested by trypsinization, washed with $Ca^{2+}$ assay buffer (10 mM HEPES, 140 mM NaCl, 2.5 mM $CaCl_2$) and incubated with 300 ml $Ca^{2+}$ assay buffer containing 1 µg/ml Annexin-FITC (BioVision) and 1 µg/ml propidium iodide (Molecular Probes) for 10 minutes on ice. Cells were analyzed by fluorescence-activated cell sorting (FACS).

After 24-hour starvation, ACE cells typically show 30% apoptosis, as assessed by annexin and propidium iodide staining. As can be seen in FIG. 26, EG-VEGF was able to rescue ACE cells from apoptosis, indicating that EG-VEGF is not only a mitogen but also a potent survival factor for epithelial cells.

Example 27

EG-VEGF Promotes Phosphorylation of eNOS

Figure 27:
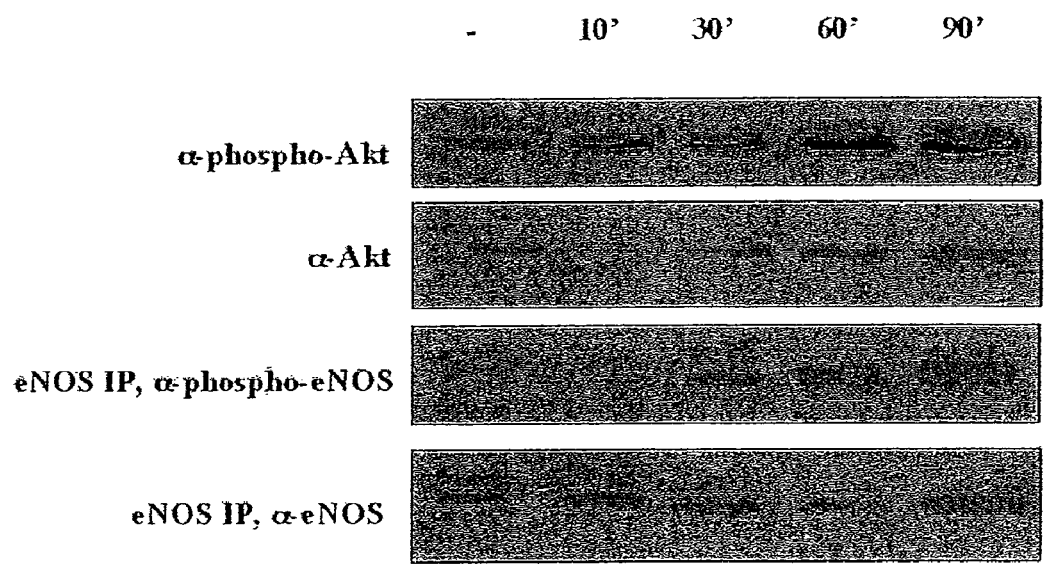
FIG. 27 shows that EG-VEGF stimulates eNOS phosphorylation. Subconfluent ACE cells were serum starved overnight, then stimulated with EG-VEGF for 10, 30, 60 and 90 minutes. Cells were extracted with lysis buffer. Part of the cell lysate was electrophoresed, transferred and blotted with an anti-phospho-Akt (upper panel) and anti-Akt (middle upper panel) antibody. The remainder of the lysate was immunoprecipitated with 1 µg anti-eNOS antibody and protein A/G beads. The immunocomplexes were electrophoresed, transferred and blotted with phopho-eNOS (middle lower panel) and eNOS (lower panel) antibodies.

Endothelial nitric oxidase (eNOS) is one of the downstream targets of Akt and is known to play a role in homeostasis of endothelial cells and angiogenesis. Phosphorylation of eNOS on Ser177 by Akt is crucial for its activation. Thus the ability of EG-VEGF to promote activation of eNOS was investigated. eNOS was immunoprecipitated from lysates of ACE cells that had been stimulated with EG-VEGF for 10 to 90 minutes. Briefly, cell lysates were immunoprecipitated for 4 hours with 1 μg anti-eNOS antibody (Biomol. Inc.) and 20 μl protein A/G beads (Pierce). The immunocomplex was washed three times with lysis buffer and boiled with SDS sample buffer. Samples were subjected to electrophoresis, transferred and blotted with anti-phospho-eNOS (Cell Signaling, Inc.) or eNOS antibody (Biomol.). As shown in FIG. 27, eNOS phosphorylation increased after a 30-minute exposure to EG-VEGF and lasted for the entire incubation period of 90 minutes. eNOS phosphorylation also correlated with Akt phosphorylation. However, the timing of eNOS phosphorylation was slightly delayed compared to Akt phosphorylation (FIG. 27).

Figure 28:
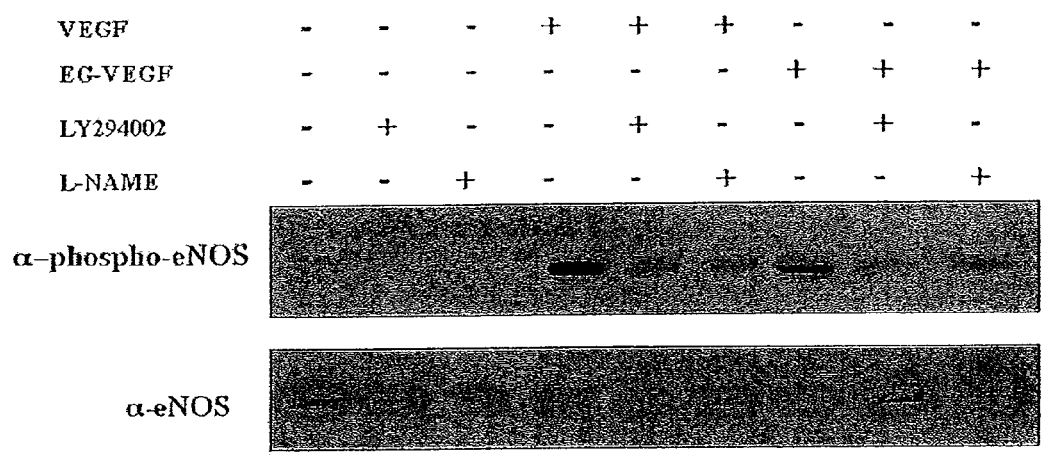
FIG. 28 illustrates that EG-VEGF induced phosphorylation of eNOS is PI 3-kinase dependent. Subconfluent ACE cells in 100 mm plates were serum starved overnight and pretreated with 20 µM LY 294002 or 4.5 nM L-NAME for 30 minutes. Cells were subsequently stimulated with 20 ng/ml VEGF for 10 minutes or with 20 nM EG-VEGF for 30 minutes. Cell lysates were immunoprecipitated with 1 µg/ml anti-eNOS and protein A/G beads. The immuno-complexes were electrophoresed, transferred and probed with an anti-phospho-eNOS antibody (upper panel) and eNOS antibody (lower panel).

The effect of 10 μM LY 294002 (Biomol. Inc.), a PI 3-kinase inhibitor, on the phosphorylation of eNOS was also examined (FIG. 28). L-NAME (5 mM; Biomol. Inc.), a competitive eNOS inhibitor was used as a control to block the phosphorylation of eNOS. Inhibition of eNOS phosphorylation by pretreatment with LY 294002 was observed, indicating that the phosphorylation of eNOS was PI 3-kinase dependent.

Example 28

Figure 29:
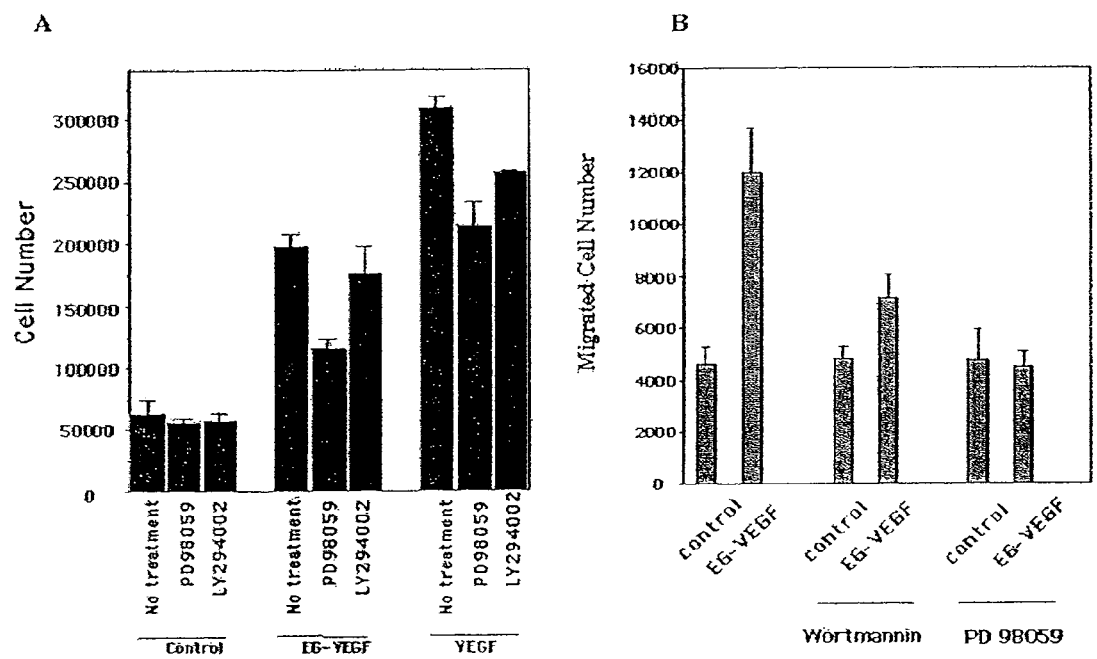
FIGS. 29A-B show that activation of MAPK is critical for EG-VEGF-induced proliferation and migration. (A) Approximately $6 \times 10^3$ ACE cells were plated in 12-well plates in complete medium overnight. Culture medium was changed to complete medium supplemented wth growth factor at the indicated concentration in the presence or absence of 20 µM PD98059 or 2 µM LY294002. After 5-7 days, cells were trypsinized and cell number was determined on a Coulter counter. (B) Approximately $2.5 \times 10^5$ ACE cells were added to the upper chamber of an EHT dual chamber system pretreated with 1% gelatin. 0.5 nM EG-VEGF was added to the lower gelatin coated chamber. Assays were carried out in the presence or absence of 200 nM wortmannin or 20 µM PD98059. The migration assays were conducted overnight and cells were counted using a Nikon fluorescence microscope. Each data point is the mean of quadruplicate determinations.

Activation of MAPK is Important for EG-VEGF-Induced Cell Proliferation and Migration The role of MAPK activation by EG-VEGF in cellular proliferation was examined in ACE cells. As can be seen in FIG. 29A, 10 μM PD98059 significantly inhibited the cellular proliferation of ACE cells stimulated by EG-VEGF (43%±6.5%) and VEGF (31%±9%) in a cell proliferation assay carried out essentially as described above. In contrast, 5 μM LY 294002, which effectively blocked Akt phosphorylation induced by EG-VEGF or VEGF, had a much smaller effect (11%±0.12% for EG-VEGF and 17%±0.8% for VEGF) in the proliferation assay. These results indicate that activation of the MAPK pathway by EG-VEGF is critical for its function as a mitogen for adrenal gland endothelial cells. Both PD98059 and wortmannin pre-treatment effectively blocked ACE cell migration stimulated by EG-VEGF (FIG. 29B), indicating that activation of both MAPK and PI 3-kinase pathways is crucial for the activity of EG-VEGF in ACE cells.

DEPOSIT OF MATERIAL

The following materials have been deposited with the American Type Culture Collection, 10801 University Blvd., Manassas, Va. 20110-2209, USA (ATCC):

| Material | ATCC Dep. No. | Deposit Date |
| --- | --- | --- |
| DNA60621-1516 1C6 2A3 2A8 4H9 | 203091 | Aug. 4, 1998 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC. 122 and the Commissioner's rules pursuant thereto (including 37 CFR. 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated polynucleotide encoding an isolated EG-VEGF polypeptide, wherein the EG-VEGF polypeptide comprises at least 95% amino acid sequence identity with residues 20-105 of SEQ ID NO:2, wherein the polypeptide promotes proliferation of adrenal cortex-derived capillary endothelial cells.

2. An isolated polynucleotide encoding an isolated EG-VEGF polypeptide, wherein the EG-VEGF polypeptide comprises at least 95% amino acid sequence identity with SEQ ID NO:2, wherein the polypeptide promotes proliferation of adrenal cortex-derived capillary endothelial cells.

3. The polynucleotide of claim 1 encoding a polypeptide comprising amino acid residues 20 to 105 of SEQ ID NO:2.

4. The polynucleotide of claim 1 or 2, comprising SEQ ID NO:1.

5. The polynucleotide of claim 1 or 2, comprising nucleotides 91 to 405 of SEQ ID NO:1.

6. The polynucleotide of claim 1 or 2, wherein the polynucleotide sequence is a native sequence.

7. The polynucleotide of claim 1 or 2, wherein the polynucleotide sequence is a human sequence.

8. An isolated polynucleotide encoding a fusion polypeptide comprising an EG-VEGF polypeptide, wherein the fusion polypeptide comprises a heterologous polypeptide.

9. The polynucleotide of claim 8, wherein the heterologous polypeptide is an Fc portion of an immunoglobulin or a HIS tag.

10. A vector comprising the polynucleotide of claim 1, 2 or 8.

11. The vector of claim 10 further comprising control sequences.

12. The vector of claim 11 wherein the control sequences are operably linked to the polynucleotide of claim 1.

13. A host cell comprising the vector of claim 10.

14. A composition comprising the polynucleotide of claim 1, 2 or 8; and a pharmaceutically acceptable carrier.

15. An article of manufacture, comprising:
(a) a container;
(b) a label on the container; and
(c) the composition of claim 14.

16. The polynucleotide of claim 2 encoding a polypeptide comprising SEQ ID NO:2.

17. The vector of claim 11 wherein the control sequences are operably linked to the polynucleotide of claim 2.

* * * * *

SEQUENCE LISTING

<160> NUMBER OF SEQ ID NOS: 18

<210> SEQ ID NO 1

```
<211> LENGTH: 1415
<212> TYPE: DNA
<213> ORGANISM: Homo sapiens

<400> SEQUENCE: 1
tggcctcccc agcttgccag gcacaaggct gagcgggagg aagcgagagg catctaagca    60
ggcagtgttt tgccttcacc ccaagtgacc atgagaggtg ccacgcgagt ctcaatcatg   120
ctcctcctag taactgtgtc tgactgtgct gtgatcacag gggcctgtga gcgggatgtc   180
cagtgtgggg caggcacctg ctgtgccatc agcctgtggc ttcgagggct gcggatgtgc   240
accccgctgg ggcgggaagg cgaggagtgc accccggca gccacaaggt ccccttcttc    300
aggaaacgca agcaccacac ctgtccttgc ttgcccaacc tgctgtgctc caggttcccg   360
gacggcaggt accgctgctc catggacttg aagaacatca ttttttaggc gcttgcctgg   420
tctcaggata cccaccatcc ttttcctgag cacagcctgg atttttatttt ctgccatgaa   480
acccagctcc catgactctc ccagtcccta cactgactac cctgatctct cttgtctagt   540
acgcacatat gcacacaggc agacatacct cccatcatga catggtcccc aggctggcct   600
gaggatgtca cagcttgagg ctgtggtgtg aaaggtggcc agcctggttc tcttccctgc   660
tcaggctgcc agagaggtgg taaatggcag aaaggacatt cccctcccc tccccaggtg    720
acctgctctc tttcctgggc cctgcccctc tccccacatg tatccctcgg tctgaattag   780
acattcctgg gcacaggctc ttgggtgcat tgctcagagt cccaggtcct ggcctgaccc   840
tcaggccctt cacgtgaggt ctgtgaggac caatttgtgg gtagttcatc ttccctcgat   900
tggttaactc cttagtttca gaccacagac tcaagattgg ctcttcccag agggcagcag   960
acagtcaccc caaggcaggt gtagggagcc cagggaggcc aatcagcccc ctgaagactc  1020
tggtcccagt cagcctgtgg cttgtggcct gtgacctgtg accttctgcc agaattgtca  1080
tgcctctgag gcccctcttt accacacttt accagttaac cactgaagcc cccaattccc  1140
acagcttttc cattaaaatg caaatggtgg tggttcaatc taatctgata ttgacatatt  1200
agaaggcaat tagggtgttt ccttaaacaa ctcctttcca aggatcagcc ctgagagcag  1260
gttggtgact ttgaggaggg cagtcctctg tccagattgg ggtgggagca agggacaggg  1320
agcagggcag gggctgaaag gggcactgat tcagaccagg gaggcaacta cacaccaaca  1380
tgctggcttt agaataaaag caccaactga aaaaa                             1415

<210> SEQ ID NO 2
<211> LENGTH: 105
<212> TYPE: PRT
<213> ORGANISM: Homo sapiens

<400> SEQUENCE: 2

Met Arg Gly Ala Thr Arg Val Ser Ile Met Leu Leu Leu Val Thr Val
1               5                   10                  15

Ser Asp Cys Ala Val Ile Thr Gly Ala Cys Glu Arg Asp Val Gln Cys
                20                  25                  30

Gly Ala Gly Thr Cys Cys Ala Ile Ser Leu Trp Leu Arg Gly Leu Arg
            35                  40                  45

Met Cys Thr Pro Leu Gly Arg Glu Gly Glu Glu Cys His Pro Gly Ser
        50                  55                  60

His Lys Val Pro Phe Phe Arg Lys Arg Lys His Thr Cys Pro Cys
65                  70                  75                  80

Leu Pro Asn Leu Leu Cys Ser Arg Phe Pro Asp Gly Arg Tyr Arg Cys
                85                  90                  95
```

```
Ser Met Asp Leu Lys Asn Ile Asn Phe
            100                 105

<210> SEQ ID NO 3
<211> LENGTH: 374
<212> TYPE: DNA
<213> ORGANISM: Homo sapiens
<220> FEATURE:
<221> NAME/KEY: unsure
<222> LOCATION: 48
<223> OTHER INFORMATION: n = A, T, C or G

<400> SEQUENCE: 3
tggctcccca gcttgccagg cacaaggctg agctggagga agcgagangc atctaagcag      60
gcagtgtttt gccttcaccc caagtgacca tgagaggtgc cacgcgagtc tcaatcatgc     120
tcctcctagt aactgtgtct gactgtgctg tgatcacagg ggcctgtgag cgggatgtcc     180
agtgtggggc aggcacctgc tgtgccatca gcctgtggct tcgagggctg cggatgtgca     240
ccccgctggg gcgggaaggc gaggagtgcc accccggcag ccacaaggtc cccttcttca     300
ggaaacgcaa gcaccacacc tgtcttgttg cccaacctgc tgtgctccag ttccggacgg     360
cagtacgctg ctca                                                      374

<210> SEQ ID NO 4
<211> LENGTH: 100
<212> TYPE: PRT
<213> ORGANISM: Homo sapiens

<400> SEQUENCE: 4

Met Leu Leu Leu Leu Leu Leu Pro Pro Leu Leu Pro Arg Ala
1               5                   10                  15

Gly Asp Ala Ala Val Ile Thr Gly Ala Cys Asp Lys Asp Ser Gln Cys
            20                  25                  30

Gly Gly Gly Met Cys Cys Ala Val Ser Ile Trp Val Lys Ser Ile Arg
        35                  40                  45

Ile Cys Thr Pro Met Gly Lys Leu Gly Asp Ser Cys His Pro Leu Thr
    50                  55                  60

Arg Lys Val Pro Phe Phe Gly Arg Arg Met His Thr Cys Pro Cys
65                  70                  75                  80

Leu Pro Gly Leu Ala Cys Leu Arg Thr Ser Phe Asn Arg Phe Ile Cys
                85                  90                  95

Leu Ala Gln Lys
            100

<210> SEQ ID NO 5
<211> LENGTH: 79
<212> TYPE: PRT
<213> ORGANISM: Snake

<400> SEQUENCE: 5

Ala Val Ile Thr Gly Ala Cys Glu Arg Asp Leu Gln Cys Gly Lys Gly
1               5                   10                  15

Thr Cys Cys Ala Val Ser Leu Trp Ile Lys Ser Val Arg Val Cys Thr
            20                  25                  30

Pro Val Gly Thr Ser Gly Glu Asp Cys His Pro Ala Ser His Lys Ile
        35                  40                  45

Pro Phe Ser Gly Gln Arg Met His His Thr Cys Pro Cys Ala Pro Asn
    50                  55                  60

Leu Ala Cys Val Gly Thr Pro Lys Phe Lys Cys Leu Ser Lys
65                  70                  75
```

<210> SEQ ID NO 6
<211> LENGTH: 83
<212> TYPE: PRT
<213> ORGANISM: Homo sapiens

<400> SEQUENCE: 6

Cys Asp Asn Gln Arg Asp Cys Gln Pro Gly Leu Cys Cys Ala Phe Gln
1               5                   10                  15

Arg Gly Leu Leu Phe Pro Val Cys Thr Pro Leu Pro Val Glu Gly Glu
            20                  25                  30

Leu Cys His Asp Pro Ala Ser Arg Leu Leu Asp Leu Ile Thr Trp Glu
        35                  40                  45

Leu Glu Pro Asp Gly Ala Leu Asp Arg Cys Pro Cys Ala Ser Gly Leu
    50                  55                  60

Leu Cys Gln Pro His Ser His Ser Leu Val Tyr Val Cys Lys Pro Thr
65                  70                  75                  80

Phe Val Gly

<210> SEQ ID NO 7
<211> LENGTH: 79
<212> TYPE: PRT
<213> ORGANISM: Xenopus

<400> SEQUENCE: 7

Cys Leu Arg Ser Thr Asp Cys Ala Pro Gly Leu Cys Cys Ala Arg His
1               5                   10                  15

Phe Trp Ser Lys Ile Cys Lys Pro Val Leu Asp Glu Gly Gln Val Cys
            20                  25                  30

Thr Lys His Arg Arg Lys Gly Ser His Gly Leu Glu Ile Phe Gln Arg
        35                  40                  45

Cys His Cys Gly Ala Gly Leu Ser Cys Arg Leu Gln Lys Gly Glu Phe
    50                  55                  60

Thr Thr Val Pro Lys Thr Ser Arg Leu His Thr Cys Gln Arg His
65                  70                  75

<210> SEQ ID NO 8
<211> LENGTH: 79
<212> TYPE: PRT
<213> ORGANISM: Porcine

<400> SEQUENCE: 8

Cys Leu Asn Ser Ala Gln Cys Lys Ser Asn Cys Cys Gln His Asp Thr
1               5                   10                  15

Ile Leu Ser Leu Ser Arg Cys Ala Leu Lys Ala Arg Glu Asn Ser Glu
            20                  25                  30

Cys Ser Ala Phe Thr Leu Tyr Gly Val Tyr Tyr Lys Cys Pro Cys Glu
        35                  40                  45

Arg Gly Leu Thr Cys Glu Gly Asp Lys Ser Leu Val Gly Ser Ile Thr
    50                  55                  60

Asn Thr Asn Phe Gly Ile Cys His Asp Val Gly Arg Ser Ser Asp
65                  70                  75

<210> SEQ ID NO 9
<211> LENGTH: 17
<212> TYPE: DNA
<213> ORGANISM: Artificial Sequence
<220> FEATURE:
<223> OTHER INFORMATION: synthetic oligonucleotide

```
<400> SEQUENCE: 9
ccggcagcca caaggtc                                                17

<210> SEQ ID NO 10
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 10
tgggcaagca aggacagg                                               18

<210> SEQ ID NO 11
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 11
ccttcttcag gaaacgcaag caccac                                      26

<210> SEQ ID NO 12
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 12
aatgacgagg gcctggagt                                              19

<210> SEQ ID NO 13
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 13
ttgatccgca taatctgcat g                                           21

<210> SEQ ID NO 14
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 14
tgtgcccact gaggagtcca acatca                                      26

<210> SEQ ID NO 15
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 15
aggccctacg tgcggcctca cacagcctgt tctga                            35

<210> SEQ ID NO 16
<211> LENGTH: 35
<212> TYPE: DNA
```

```
-continued

<213> ORGANISM: Artificial Sequence
<220> FEATURE:
<223> OTHER INFORMATION: synthetic oligonucleotide

<400> SEQUENCE: 16
aggccctaat tgcggcctca cacagcctgt tctga                            35

<210> SEQ ID NO 17
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 17
gctaaggacg tgctattcat ggggtgcagg aagat                            35

<210> SEQ ID NO 18
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 18
gctaaggaat tgctattcat ggggtgcagg aagat                            35
```